(12) United States Patent
Vincent et al.

(10) Patent No.: US 10,907,159 B2
(45) Date of Patent: Feb. 2, 2021

(54) METHODS OF TREATING CANCER BY INHIBITION OF DNA REPAIR PROTEINS USING ANTISENSE BASED THERAPIES

(71) Applicant: SARISSA INC., London (CA)

(72) Inventors: Mark D. Vincent, London (CA); Peter Ferguson, London (CA); D. James Koropatnick, London (CA); Mateusz Rytelewski, Mississauga (CA)

(73) Assignee: SARISSA INC.

( * ) Notice: Subject to any disclaimer, the term of this patent is extended or adjusted under 35 U.S.C. 154(b) by 0 days.

(21) Appl. No.: 16/065,641

(22) PCT Filed: Dec. 13, 2016

(86) PCT No.: PCT/CA2016/051464
§ 371 (c)(1),
(2) Date: Jun. 22, 2018

(87) PCT Pub. No.: WO2017/106964
PCT Pub. Date: Jun. 29, 2017

(65) Prior Publication Data
US 2019/0002884 A1     Jan. 3, 2019

Related U.S. Application Data

(60) Provisional application No. 62/270,634, filed on Dec. 22, 2015.

(51) Int. Cl.
| | | |
|---|---|---|
| *C12N 15/113* | (2010.01) | |
| *A61K 31/713* | (2006.01) | |
| *A61K 33/243* | (2019.01) | |
| *A61K 45/06* | (2006.01) | |
| *A61K 31/502* | (2006.01) | |
| *A61K 31/712* | (2006.01) | |
| *A61K 31/7125* | (2006.01) | |

(52) U.S. Cl.
CPC ........ *C12N 15/1135* (2013.01); *A61K 31/502* (2013.01); *A61K 31/712* (2013.01); *A61K 31/713* (2013.01); *A61K 31/7125* (2013.01); *A61K 33/243* (2019.01); *A61K 45/06* (2013.01); *C12N 15/113* (2013.01); *C12N 15/1137* (2013.01); *C12Y 201/01045* (2013.01); *C12N 2310/11* (2013.01); *C12N 2310/14* (2013.01); *C12N 2310/315* (2013.01); *C12N 2310/321* (2013.01); *C12N 2310/341* (2013.01); *C12N 2310/346* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 9,359,605 B2 * | 6/2016 | Vincent | ............. A61K 31/7088 |
| 2014/0113951 A1 * | 4/2014 | Vincent | ............. A61K 31/7088 |
| | | | 514/44 A |

* cited by examiner

*Primary Examiner* — Sean McGarry
(74) *Attorney, Agent, or Firm* — Adsero IP

(57) ABSTRACT

Methods of treating cancer using antisense based therapies including antisense oligonucleotides of si RNAs directed against DNA double-strand break repair proteins such as BRCA2 or RAD51 are provided. The antisense based therapies can be used alone, in tandem or in combination with other cancer therapies, in particular with therapies that lead to DNA damage, inhibition of DNA repair or inhibition of DNA synthesis, such as radiation, platinum drugs, alkylating agents, PARP inhibitors, or inhibitors of thymidylate synthase.

17 Claims, 49 Drawing Sheets
Specification includes a Sequence Listing.

SEQUENCE LISTING

```
<160> NUMBER OF SEQ ID NOS: 46

<210> SEQ ID NO 1
<211> LENGTH: 20
<212> TYPE: RNA
<213> ORGANISM: Artificial Sequence
<220> FEATURE:
<223> OTHER INFORMATION: BR1 gapmer
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA
<221> NAME/KEY: misc_RNA
<222> LOCATION: (15)...(20)
<223> OTHER INFORMATION: 2'-O-methyl RNA

<400> SEQUENCE: 1
guaucucttg acgtuccuua                                               20

<210> SEQ ID NO 2
<211> LENGTH: 20
<212> TYPE: RNA
<213> ORGANISM: Artificial Sequence
<220> FEATURE:
<223> OTHER INFORMATION: BR2 gapmer
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA
<221> NAME/KEY: misc_RNA
<222> LOCATION: (15)...(20)
<223> OTHER INFORMATION: 2'-O-methyl RNA

<400> SEQUENCE: 2
uaccagcgag caggccgagu                                               20

<210> SEQ ID NO 3
<211> LENGTH: 20
```

```
<212> TYPE: RNA
<213> ORGANISM: Artificial Sequence
<220> FEATURE:
<223> OTHER INFORMATION: BR3 gapmer
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA
<221> NAME/KEY: misc_RNA
<222> LOCATION: (15)...(20)
<223> OTHER INFORMATION: 2'-O-methyl RNA

<400> SEQUENCE: 3
ugcccgatac acaaacgcug                                              20

<210> SEQ ID NO 4
<211> LENGTH: 20
<212> TYPE: DNA
<213> ORGANISM: Artificial Sequence
<220> FEATURE:
<223> OTHER INFORMATION: antisense

<400> SEQUENCE: 4
cagcgtttgt gtatcgggca                                              20

<210> SEQ ID NO 5
<211> LENGTH: 17
<212> TYPE: DNA
<213> ORGANISM: Artificial Sequence
<220> FEATURE:
<223> OTHER INFORMATION: antisense

<400> SEQUENCE: 5
ttggatccaa taggcat                                                 17

<210> SEQ ID NO 6
<211> LENGTH: 21
<212> TYPE: DNA
<213> ORGANISM: Artificial Sequence
<220> FEATURE:
<223> OTHER INFORMATION: antisense

<400> SEQUENCE: 6
tacgtactcc agaacattta a                                            21

<210> SEQ ID NO 7
<211> LENGTH: 21
<212> TYPE: DNA
<213> ORGANISM: Artificial Sequence
<220> FEATURE:
<223> OTHER INFORMATION: antisense

<400> SEQUENCE: 7
ttggaggaat atcgtaggta a                                            21

<210> SEQ ID NO 8
<211> LENGTH: 21
<212> TYPE: DNA
<213> ORGANISM: Artificial Sequence
<220> FEATURE:
<223> OTHER INFORMATION: antisense

<400> SEQUENCE: 8
caggacacaa ttacaactaa a                                            21
```

```
<210> SEQ ID NO 9
<211> LENGTH: 19
<212> TYPE: RNA
<213> ORGANISM: Artificial Sequence
<220> FEATURE:
<223> OTHER INFORMATION: siRNA "A"

<400> SEQUENCE: 9
uaaauagcaa guccguuuc                                                    19

<210> SEQ ID NO 10
<211> LENGTH: 19
<212> TYPE: RNA
<213> ORGANISM: Artificial Sequence
<220> FEATURE:
<223> OTHER INFORMATION: siRNA "B"

<400> SEQUENCE: 10
uaaugaagca ucugauacc                                                    19

<210> SEQ ID NO 11
<211> LENGTH: 19
<212> TYPE: RNA
<213> ORGANISM: Artificial Sequence
<220> FEATURE:
<223> OTHER INFORMATION: siRNA "C"

<400> SEQUENCE: 11
uauuaaaccu gcauucuuc                                                    19

<210> SEQ ID NO 12
<211> LENGTH: 20
<212> TYPE: RNA
<213> ORGANISM: Artificial Sequence
<220> FEATURE:
<223> OTHER INFORMATION: siRNA "D"

<400> SEQUENCE: 12
guaucucuug acguuccuua                                                   20

<210> SEQ ID NO 13
<211> LENGTH: 20
<212> TYPE: DNA
<213> ORGANISM: Artificial Sequence
<220> FEATURE:
<223> OTHER INFORMATION: BR1 DNA

<400> SEQUENCE: 13
gtatctcttg acgttcctta                                                   20

<210> SEQ ID NO 14
<211> LENGTH: 20
<212> TYPE: DNA
<213> ORGANISM: Artificial Sequence
<220> FEATURE:
<223> OTHER INFORMATION: BR2 DNA

<400> SEQUENCE: 14
taccagcgag caggccgagt                                                   20

<210> SEQ ID NO 15
<211> LENGTH: 20
<212> TYPE: DNA
<213> ORGANISM: Artificial Sequence
<220> FEATURE:
<223> OTHER INFORMATION: BR3 DNA
```

```
<400> SEQUENCE: 15
tgcccgatac acaaacgctg                                               20

<210> SEQ ID NO 16
<211> LENGTH: 20
<212> TYPE: DNA
<213> ORGANISM: Artificial Sequence
<220> FEATURE:
<223> OTHER INFORMATION: ODN83

<400> SEQUENCE: 16
gccagtggca acatccttaa                                               20

<210> SEQ ID NO 17
<211> LENGTH: 20
<212> TYPE: RNA
<213> ORGANISM: Artificial Sequence
<220> FEATURE:
<223> OTHER INFORMATION: BR1 modified
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA
<221> NAME/KEY: misc_RNA
<222> LOCATION: (8)...(20)
<223> OTHER INFORMATION: 2'-O-methyl RNA

<400> SEQUENCE: 17
guaucucttg acgtuccuua                                               20

<210> SEQ ID NO 18
<211> LENGTH: 20
<212> TYPE: RNA
<213> ORGANISM: Artificial Sequence
<220> FEATURE:
<223> OTHER INFORMATION: BR1 target

<400> SEQUENCE: 18
uaaggaacgu caagagauac                                               20

<210> SEQ ID NO 19
<211> LENGTH: 20
<212> TYPE: RNA
<213> ORGANISM: Artificial Sequence
<220> FEATURE:
<223> OTHER INFORMATION: BR2 target

<400> SEQUENCE: 19
acucggccug cucgcuggua                                               20

<210> SEQ ID NO 20
<211> LENGTH: 20
<212> TYPE: RNA
<213> ORGANISM: Artificial Sequence
<220> FEATURE:
<223> OTHER INFORMATION: BR2 modified
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA
<221> NAME/KEY: misc_RNA
<222> LOCATION: (15)...(20)
<223> OTHER INFORMATION: 2'-O-methyl RNA

<400> SEQUENCE: 20
```
uaccagcgag caggccgagu                                              20

<210> SEQ ID NO 21
<211> LENGTH: 20
<212> TYPE: RNA
<213> ORGANISM: Artificial Sequence
<220> FEATURE:
<223> OTHER INFORMATION: BR3 target

<400> SEQUENCE: 21
cagcguuugu guaucgggca                                              20

<210> SEQ ID NO 22
<211> LENGTH: 20
<212> TYPE: RNA
<213> ORGANISM: Artificial Sequence
<220> FEATURE:
<223> OTHER INFORMATION: BR3 modified
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA
<221> NAME/KEY: misc_RNA
<222> LOCATION: (15)...(20)
<223> OTHER INFORMATION: 2'-O-methyl RNA

<400> SEQUENCE: 22
ugcccgatac acaaacgcug                                              20

<210> SEQ ID NO 23
<211> LENGTH: 20
<212> TYPE: RNA
<213> ORGANISM: Artificial Sequence
<220> FEATURE:
<223> OTHER INFORMATION: ODN 32 gapmer control
<221> NAME/KEY: misc_feature
<222> LOCATION: (7)...(14)
<223> OTHER INFORMATION: DNA

<400> SEQUENCE: 23
augcgccaac ggttccuaaa                                              20

<210> SEQ ID NO 24
<211> LENGTH: 20
<212> TYPE: RNA
<213> ORGANISM: Artificial Sequence
<220> FEATURE:
<223> OTHER INFORMATION: ODN491S (gapmer control)
<221> NAME/KEY: misc_feature
<222> LOCATION: (7)...(14)
<223> OTHER INFORMATION: DNA

<400> SEQUENCE: 24
ggagugcgtg agtcgaugua                                              20

<210> SEQ ID NO 25
<211> LENGTH: 20
<212> TYPE: RNA
<213> ORGANISM: Artificial Sequence
<220> FEATURE:
<223> OTHER INFORMATION: ODN83
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA

```
<221> NAME/KEY: misc_RNA
<222> LOCATION: (15)...(20)
<223> OTHER INFORMATION: 2'-O-methyl RNA

<400> SEQUENCE: 25
gccaguggca acatccuuaa                                               20

<210> SEQ ID NO 26
<211> LENGTH: 20
<212> TYPE: RNA
<213> ORGANISM: Artificial Sequence
<220> FEATURE:
<223> OTHER INFORMATION: prior art target

<400> SEQUENCE: 26
cugcaucugc auugccauua                                               20

<210> SEQ ID NO 27
<211> LENGTH: 15
<212> TYPE: RNA
<213> ORGANISM: Artificial Sequence
<220> FEATURE:
<223> OTHER INFORMATION: prior art target

<400> SEQUENCE: 27
ggcuucacua auucc                                                    15

<210> SEQ ID NO 28
<211> LENGTH: 19
<212> TYPE: RNA
<213> ORGANISM: Artificial Sequence
<220> FEATURE:
<223> OTHER INFORMATION: prior art target

<400> SEQUENCE: 28
guaauggcaa ugcagaugc                                                19

<210> SEQ ID NO 29
<211> LENGTH: 20
<212> TYPE: RNA
<213> ORGANISM: Artificial Sequence
<220> FEATURE:
<223> OTHER INFORMATION: RAD51 target

<400> SEQUENCE: 29
gaaugggucu gcacagauuc                                               20

<210> SEQ ID NO 30
<211> LENGTH: 20
<212> TYPE: RNA
<213> ORGANISM: Artificial Sequence
<220> FEATURE:
<223> OTHER INFORMATION: RAD51 antisense gapmer
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA
<221> NAME/KEY: misc_RNA
<222> LOCATION: (15)...(20)
<223> OTHER INFORMATION: 2'-O-methyl RNA

<400> SEQUENCE: 30
gaaucugtgc agacccauuc                                               20

<210> SEQ ID NO 31
```

<210> SEQ ID NO 31
<211> LENGTH: 20
<212> TYPE: DNA
<213> ORGANISM: Artificial Sequence
<220> FEATURE:
<223> OTHER INFORMATION: DNA-PK antisense

<400> SEQUENCE: 31
gcaagccagc tgagggcaca                                                  20

<210> SEQ ID NO 32
<211> LENGTH: 21
<212> TYPE: DNA
<213> ORGANISM: Artificial Sequence
<220> FEATURE:
<223> OTHER INFORMATION: DNA-PK antisense

<400> SEQUENCE: 32
gggcattcca aggcttcccc a                                                21

<210> SEQ ID NO 33
<211> LENGTH: 20
<212> TYPE: DNA
<213> ORGANISM: Artificial Sequence
<220> FEATURE:
<223> OTHER INFORMATION: DNA-PK antisense

<400> SEQUENCE: 33
gggctcccat ccttcccagg                                                  20

<210> SEQ ID NO 34
<211> LENGTH: 22
<212> TYPE: DNA
<213> ORGANISM: Artificial Sequence
<220> FEATURE:
<223> OTHER INFORMATION: DNA-PK antisense

<400> SEQUENCE: 34
aggggccttc tcatgaccca gg                                               22

<210> SEQ ID NO 35
<211> LENGTH: 21
<212> TYPE: DNA
<213> ORGANISM: Artificial Sequence
<220> FEATURE:
<223> OTHER INFORMATION: DNA-PK antisense

<400> SEQUENCE: 35
actgctggat tggcacctgc t                                                21

<210> SEQ ID NO 36
<211> LENGTH: 20
<212> TYPE: DNA
<213> ORGANISM: Artificial Sequence
<220> FEATURE:
<223> OTHER INFORMATION: DNA-PK antisense

<400> SEQUENCE: 36
tggggtctgt tgcctggtcc                                                  20

<210> SEQ ID NO 37
<211> LENGTH: 19
<212> TYPE: RNA
<213> ORGANISM: Artificial Sequence
<220> FEATURE:
<223> OTHER INFORMATION: siRNA against RAD51 "A"

<400> SEQUENCE: 37

-continued

```
aauuucuuca caucguugg                                         19

<210> SEQ ID NO 38
<211> LENGTH: 19
<212> TYPE: RNA
<213> ORGANISM: Artificial Sequence
<220> FEATURE:
<223> OTHER INFORMATION: siRNA against RAD51 "B"

<400> SEQUENCE: 38
uuauccagga caucacugc                                         19

<210> SEQ ID NO 39
<211> LENGTH: 19
<212> TYPE: RNA
<213> ORGANISM: Artificial Sequence
<220> FEATURE:
<223> OTHER INFORMATION: siRNA against RAD51 "C"

<400> SEQUENCE: 39
ugagcuacca ccugauuag                                         19

<210> SEQ ID NO 40
<211> LENGTH: 19
<212> TYPE: RNA
<213> ORGANISM: Artificial Sequence
<220> FEATURE:
<223> OTHER INFORMATION: siRNA against RAD51 "D"

<400> SEQUENCE: 40
ugaugcaugg gcgaugaua                                         19

<210> SEQ ID NO 41
<211> LENGTH: 20
<212> TYPE: RNA
<213> ORGANISM: Artificial Sequence
<220> FEATURE:
<223> OTHER INFORMATION: BR1 RNA

<400> SEQUENCE: 41
guaucucuug acguuccuua                                        20

<210> SEQ ID NO 42
<211> LENGTH: 20
<212> TYPE: RNA
<213> ORGANISM: Artificial Sequence
<220> FEATURE:
<223> OTHER INFORMATION: BR2 RNA

<400> SEQUENCE: 42
uaccagcgag caggccgagu                                        20

<210> SEQ ID NO 43
<211> LENGTH: 20
<212> TYPE: RNA
<213> ORGANISM: Artificial Sequence
<220> FEATURE:
<223> OTHER INFORMATION: BR3 RNA

<400> SEQUENCE: 43
ugcccgauac acaaacgcug                                        20

<210> SEQ ID NO 44
<211> LENGTH: 20
<212> TYPE: DNA
```

```
<213> ORGANISM: Artificial Sequence
<220> FEATURE:
<223> OTHER INFORMATION: RAD51 antisense

<400> SEQUENCE: 44
gaatctgtgc agacccattc                                                    20

<210> SEQ ID NO 45
<211> LENGTH: 20
<212> TYPE: RNA
<213> ORGANISM: Artificial Sequence
<220> FEATURE:
<223> OTHER INFORMATION: RAD51 gapmer
<221> NAME/KEY: misc_RNA
<222> LOCATION: (1)...(6)
<223> OTHER INFORMATION: 2'-O-methyl RNA
<221> NAME/KEY: misc_feature
<222> LOCATION: (7)...(14)
<223> OTHER INFORMATION: DNA
<221> NAME/KEY: misc_RNA
<222> LOCATION: (15)...(20)
<223> OTHER INFORMATION: 2'-O-methyl RNA

<400> SEQUENCE: 45
gaaucugtgc agacccauuc                                                    20

<210> SEQ ID NO 46
<211> LENGTH: 19
<212> TYPE: DNA
<213> ORGANISM: Artificial Sequence
<220> FEATURE:
<223> OTHER INFORMATION: BRCA2 target

<400> SEQUENCE: 46
ccgattacct gtgtaccct                                                     19
```

METHODS OF TREATING CANCER BY INHIBITION OF DNA REPAIR PROTEINS USING ANTISENSE BASED THERAPIES

CROSS-REFERENCE TO RELATED APPLICATION

This application claims priority to and is a 35 U.S.C. §371 national phase application of PCT/CA2016/051464 (WO2017/106964), filed on Dec. 13, 2016, entitled "METHODS OF TREATING CANCER BY INHIBITION OF DNA REPAIR PROTEINS USING ANTISENSE BASED THERAPIES", which application claims priority to and the benefit of U.S. Provisional patent application No. 62/270,634, filed Dec. 22, 2015; the disclosures of which are incorporated herein by reference in their entirety.

SEQUENCE STATEMENT

Incorporated by reference herein in its entirety is the Sequence Listing entitled "Sequence_Listing_0238_753_127US," created Apr. 23, 2019, size of 10 kilobytes.

FIELD OF THE INVENTION

The present invention relates to the field of cancer therapy and, in particular, to the use of antisense based therapies directed against DNA repair proteins involved in the repair of double strand DNA breaks in the treatment of cancer.

BACKGROUND OF THE INVENTION

Cancer is characterized by genetic instability both at the chromosomal level and at the nucleotide level. The acquisition of certain mutations confers a selective advantage to the cancer cells and is critical in cancer progression. A diverse array of defects in both DNA polymerases and DNA repair enzymes appears to contribute to the increased genetic instability observed in cancer cells (Hanahan et al, 2011, Cell, 144: 646-674). Although necessary to confer a selective advantage to cancer cells, excessive instability in the cancer cell genome is suggested to be incompatible with cell viability. Treatment of cancer by increasing the genetic instability of cancer cells beyond the threshold over which the cancer cells are no longer viable has been proposed as an alternative therapeutic approach (Loeb, 2011, Nature Reviews Cancer 11, 450-457).

A variety of anticancer drugs, including platinum drugs, alkylating agents, and anthracyclines, share DNA as a common target of biological activity. Covalent binding of drugs to DNA or other interactions that interfere with transcription and/or replication initiates a series of events that, although intended to rescue the cell for further proliferation, may eventually lead to cell death. This depends on various factors, including the degree of drug binding, the activity of the DNA repair systems, and the balance between pro- and anti-apoptotic mechanisms in the cell. The cytotoxic effect, and therefore the clinical effectiveness, of these classes of drugs can potentially be reduced by the action of DNA repair enzymes and damage-signal molecules. In contrast, if DNA repair is deficient, a phenotype which may contribute to malignant progression (mutator phenotype), the resulting tumour may be more susceptible to DNA-damaging agents (1). One deficiency that contributes to oncogenesis but leaves the tumour vulnerable to targeted treatment directed against other genes or gene products capable of compensating for the original deficiency is referred to as "synthetic lethality."

Synthetic lethality (also known as Synthetic Sickness/Lethality or "SSL") can be described as follows: "Two genes have a SSL relationship when inhibition or mutation of either gene alone does not cause loss of viability/sickness, but simultaneous inhibition of both genes results in reduced cell viability or an impairment of cellular health/fitness." (Brough et al, 2011, Curr Op in Gen and Dev., 21: 34-41). Brough et al. also describe how SSL relationship can be used to identify therapeutic options in that if one gene in an SSL relationship is a tumour suppressor gene, then its synthetic lethal partner becomes a candidate therapeutic target for tumours with a defined tumour suppressor gene dysfunction. SSL can occur between genes acting in the same biochemical pathway or in distinct but compensatory pathways, and components of the same pathway often share the same SSL partners. Synthetic lethality can be mimicked by targeted therapies (Chan et al, Nat. Rev. Drug. Discov., 10: 351-364).

Two DNA repair-associated proteins that are known to be deficient in several forms of inherited cancer susceptibility are BRCA1 and BRCA2. These proteins are intimately involved with proteins such as PALB2 and RAD51 in mediating homologous recombination (HR)-dependent DNA (HR-DD) repair, the most precise of several repair pathways (8-10). BRCA2 mediates binding of RAD51 to short, single-stranded DNA as part of the recognition of DNA strand breaks and initiation of DNA repair (8, 9). BRCA1 is then involved in processing of the free end of a DNA strand break, whereas BRCA2 is essential to a strand-exchange step of HR (9). The repair complex includes direct physical interactions between BRCA1, BRCA2, PALB2, BARD1 and RAD51, not only at sites of DNA damage but also at chromosomal foci in mitotic cells (8).

Another important protein in mediating base-excision DNA repair (single strand DNA break repair) is the enzyme PARP1 (poly[adenosine diphosphate (ADP)-ribose] polymerase) (8). PARP regulates transcription of genes involved in other repair mechanisms, including BRCA2 (11). However, PARP is also involved in repair pathways that are independent of BRCA1 and BRCA2 pathways and that tend to be more error-prone (8). If cells are deficient in BRCA1 or BRCA2, and thus HR-DD repair, the cells become dependent upon PARP-dependent repair pathways (8). In this case, repair is very sensitive to inhibitors of PARP, and cells tend to accumulate replication-generated errors that would normally be repaired immediately, leading eventually to cell cycle arrest and cell death (8).

Clinical examples of drug-hypersensitivity of DNA-repair-deficient tumours have been described. Familial carcinomas of breast, ovary and prostate with a deficiency of BRCA1 or BRCA2 are more sensitive to olaparib (4-[(3-{[4-cyclopropylcarbonyl)piperazin-1-yl]carbonyl}-4-fluorophenyl)methyl]phthalazin-1(2H)-one; also known as AZD2281). Treatment of BRCA1- or BRCA2-deficient tumours with olaparib has resulted in good clinical responses (2).

As a method to study the function of specific gene products in cellular processes, researchers have utilized the ability of nucleic acid that is complementary to mRNA to initiate degradation of that mRNA specifically. This phenomenon, which exists in cells as part of a stringent mechanism of control of mRNA levels as well as an antiviral defence, makes use of nucleic acids that are referred to as "antisense". Specific down-regulation of intracellular proteins can be accomplished with the use of such antisense nucleic acids that bind specifically, based on sequence matching and Watson-Crick base-pairing, to a selected mRNA target. By recruitment of intracellular endonucleases, the target mRNA is destroyed, and the protein usually generated from it disappears with normal turnover. Full-length antisense mRNA expression vectors are currently not of potential clinical use. However, shorter antisense nucleic acids have clinical potential, and one format has already been used in clinical trials. Several different chemistries of antisense molecules have been used in experimental systems to specifically down-regulate an mRNA of interest. Oligonucleotides (OLIGOs) consist of a single-stranded molecule that is introduced into cultured cells using a cationic liposomal transfecting agent in order to permeate the cell membrane, although there is some indication that carriers in the blood are able to facilitate entry of OLIGOs into cells in vivo.

It has been reported that down-regulation of BRCA2 using an antisense OLIGO targeted against the region of the translational start site increased the sensitivity of tumour cells to mitoxantrone in vitro (6). The authors concluded that these effects could be applied to a BRCA2 genetic screening method as a predictor of response to a specific therapeutic approach. It has also been reported that cells treated with a pool of 4 siRNAs targeting BRCA1 or BRCA2 (Dharmacon, Thermo Fisher, Lafayette, Colo., USA) were more sensitive than control siRNA-treated counterparts to cytotoxic activity of a PARP inhibitor (7). In this study, the authors concluded that their synthetic lethal siRNA screen with chemical inhibitors could be used to define new determinants of sensitivity and potential therapeutic targets. Both of these two studies focussed on the use of BRCA2 inhibition in screening methods; neither suggested that inhibition of BRCA2 may have therapeutic potential.

U.S. Pat. No. 5,837,492 describes materials and methods used to isolate and detect a human breast cancer predisposing gene (BRCA2) and describes generally polynucleotides comprising all or a part of a BRCA2 locus, including antisense oligonucleotides.

United States Patent Publication No. 2004/0097442 describes compounds, compositions and methods for modulating the expression of BRCA2 region transcription unit CG005, which is a region of the BRCA2 locus that is outside the BRCA2 gene itself. The compositions comprise oligonucleotides targeted to nucleic acid encoding BRCA2 region transcription unit CG005, i.e. oligonucleotides targeted to mRNA encoding part of the BRCA2 locus other than the BRCA2 gene. Methods of using these compounds for the diagnosis and treatment of disease associated with expression of BRCA2 region transcription unit CG005 are also generally described. United States Patent Publication No. 2004/0097442 does not describe antisense oligonucleotides directed to the mRNA encoding BRCA2.

United States Patent Publication No. 2005/0227919 describes methods and means relating to the treatment of cancers which are deficient in HR-dependent DNA DSB repair using inhibitors which target base excision repair components such as poly (ADP-ribose) polymerase (PARP).

International Patent Application No. PCT/EP2007/008852 (Publication No. WO 2008/043561) describes pharmaceutical compositions comprising modulators of kinases, kinase-binding polypeptides and/or an inhibitor for influenza virus replication for the prevention and/or treatment of influenza. This application also describes genome-wide screening to identify human genes that are relevant for replication of influenza viruses. Several thousand genes were identified, including BRCA2, and target sequences for "knocking down" each gene using siRNA technology were also identified. Four target sequences within BRCA2 were identified.

United States Patent Publication No. 2011/0230433 describes methods and composition for treatment of cancer by increasing the mutation rate of cancer cells beyond an error threshold over which the cancer cells are no longer viable.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide methods of treating cancer by inhibition of DNA repair proteins using antisense based therapies. In accordance with one aspect of the present invention, there is provided a method of treating cancer in a subject comprising administering to the subject an effective amount of an antisense oligonucleotide of between 7 and 100 nucleotides in length comprising a sequence complementary to an mRNA encoding a DNA double strand break repair protein.

In accordance with another aspect of the present invention, there is provided a method of treating cancer in a subject comprising administering to the subject an effective amount of one or more siRNA comprising a sequence complementary to an mRNA encoding a DNA double strand break repair protein.

In accordance with another aspect of the present invention, there is provided an antisense oligonucleotide of between 7 and 100 nucleotides in length comprising at least 7 consecutive nucleotides of the sequence as set forth in any one of SEQ ID NOs: 1, 2, 3, 13, 14, 15, 30, 31, 32, 33, 34, 35 or 36.

In accordance with another aspect of the present invention, there is provided a pharmaceutical composition comprising one or more antisense oligonucleotides of between 7 and 100 nucleotides in length comprising at least 7 consecutive nucleotides of the sequence as set forth in any one of SEQ ID NOs: 2, 3, 14, 15, 30, 31, 32, 33, 34, 35 or 36.

In accordance with another aspect of the present invention, there is provided a method of treating cancer in a subject comprising administering to the subject an effective amount one or more anti-BRCA2 siRNA. In one embodiment, the method comprising administering a chemotherapeutic.

In accordance with another aspect of the present invention, there is provided a method of treating cancer in a subject comprising administering to the subject an effective amount an anti-thymidylate synthase antisense and an anti-BRCA2 antisense in combination with a platinum-based chemotherapeutic and a small molecule inhibitor of thymidylate synthase

BRIEF DESCRIPTION OF THE DRAWINGS

These and other features of the invention will become more apparent in the following detailed description in which reference is made to the appended drawings.

D: MDA-MB-231 breast cancer cells were transfected with control or BRCA2 ASO, treated with olaparib, and proliferation determined as described above.

E: SKOV-3 cells were transfected with control or BRCA2 ASO and then treated with olaparib 24 hours post transfection. Ninety-six hours post transfection, cells were counted, plated, and re-transfected with control ASO or BRCA2 ASO and re-treated with olaparib. Cell counts were performed 96 hours post transfection (*p<0.05). Means±SD from representative experiments are shown. All experiments were repeated at least once.

Figure 25:
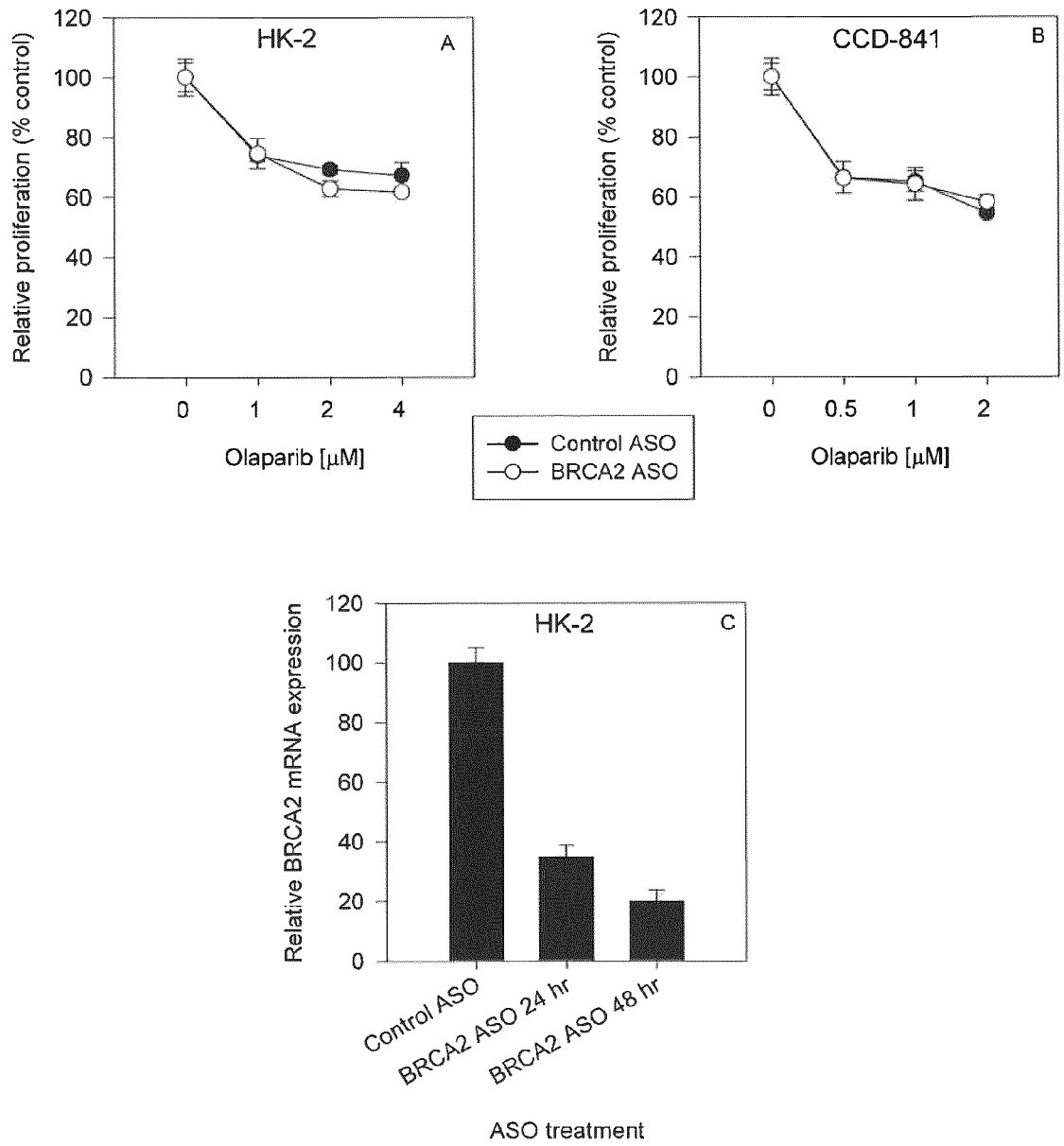

FIG. 25 illustrates that non-cancerous kidney and colon cell lines are not sensitized to olaparib by BRCA2 down-regulation. Non-tumor HK-2 kidney proximal tubule epithelial cells (A) and CCD-841 fetal colon epithelial cells (B) were transfected with control or BRCA2 ASO and then treated with three different concentrations of olaparib. Proliferation was determined by cell counting 96 hours post-transfection (*p<0.05).

C: BRCA2 mRNA levels in HK-2 cells were measured by qPCR following transfection of BRCA2 ASO. Means±SD from representative experiments are shown. All experiments were repeated at least once.

Figure 26:
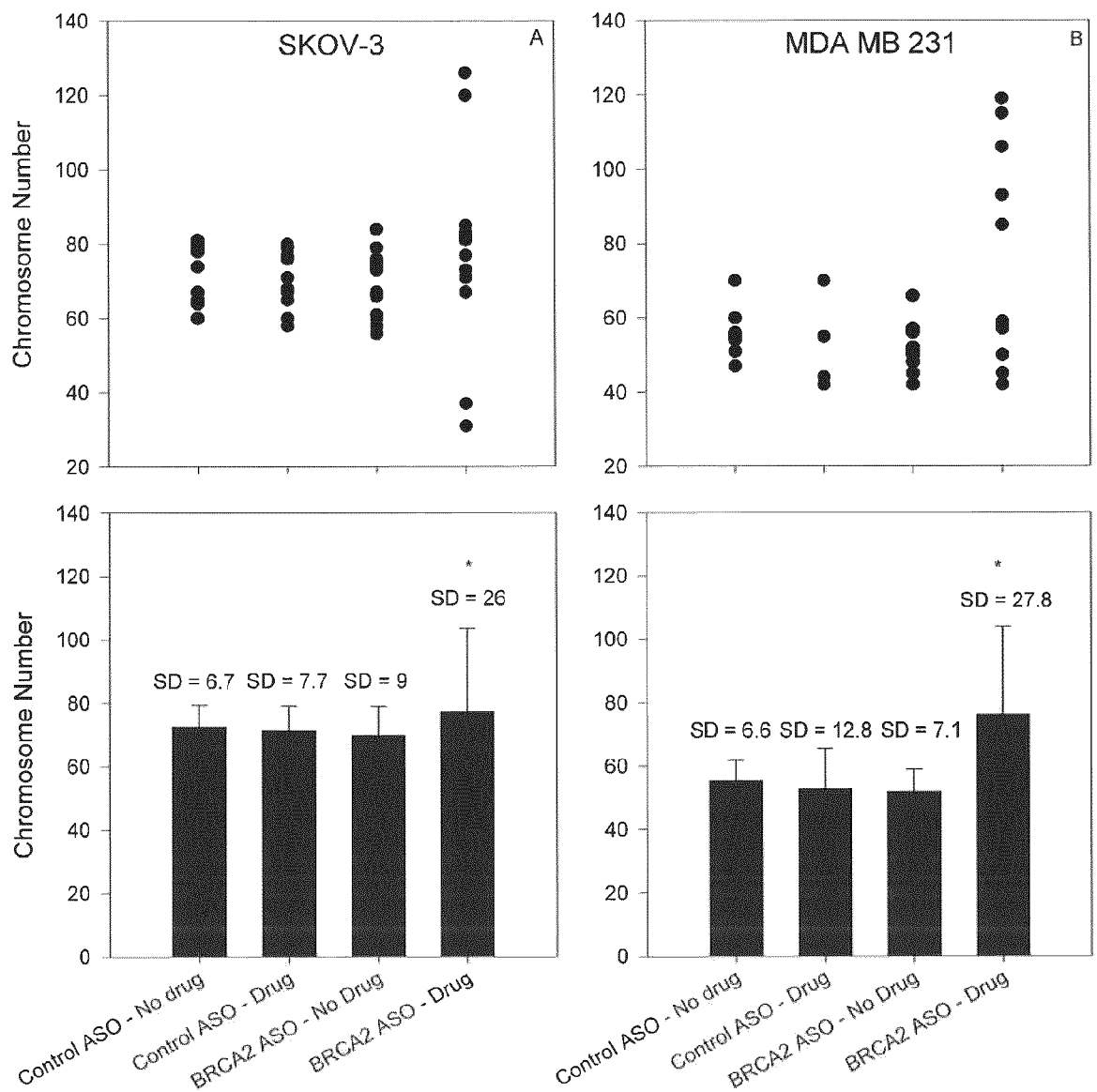
Figure 26:
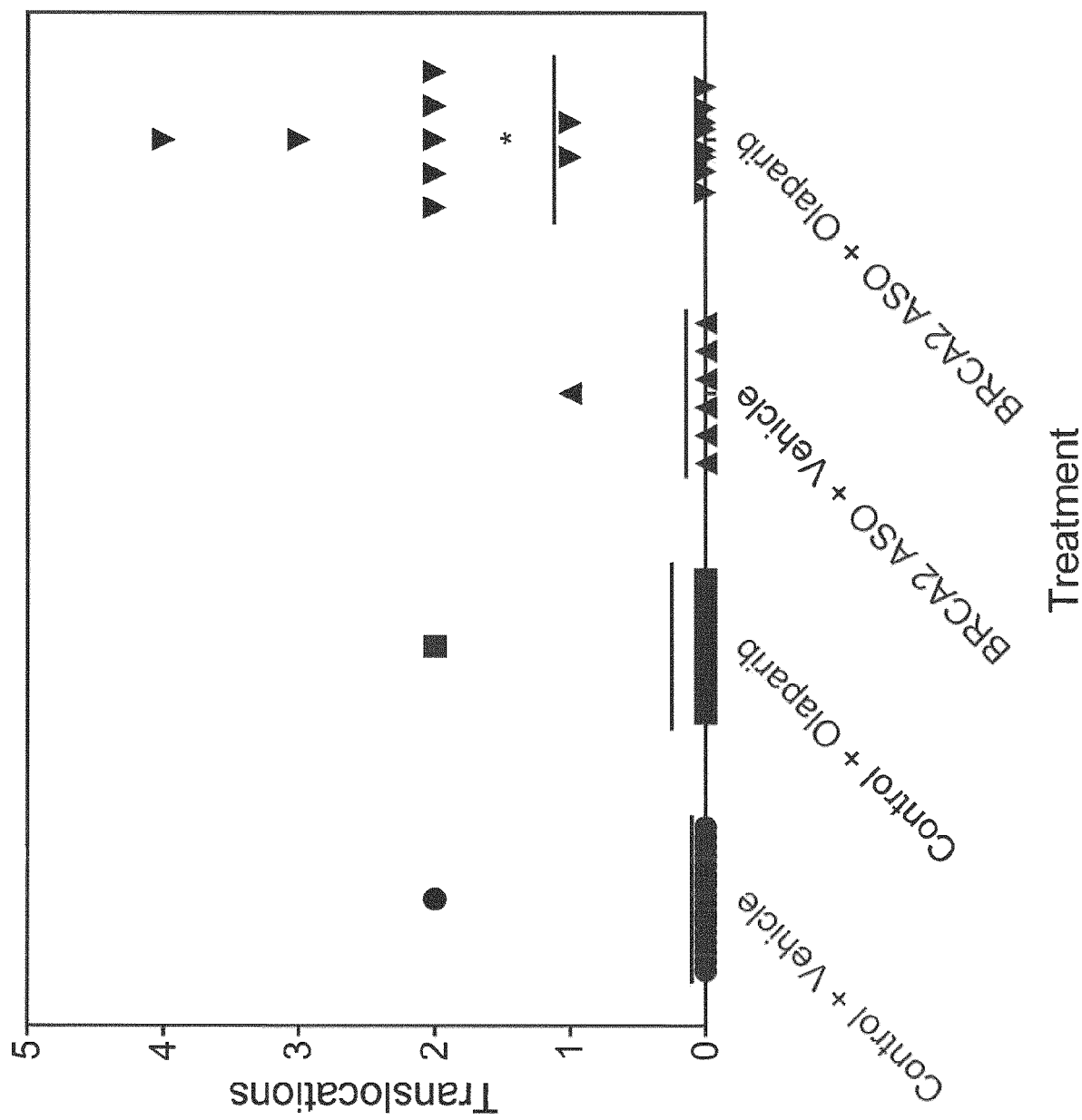

FIG. 26 illustrates that combined BRCA2 ASO and olaparib treatment increases the variability in chromosome number and increases translocation frequency in ovarian and breast cancer cells. SKOV-3 (A) and MDA-MB-231 (B) cells were treated with control ASO or BRCA2 ASO in the presence or absence of olaparib. Forty-eight hours following olaparib treatment, cells were fixed and processed to yield metaphase spreads. The number of chromosomes in individual metaphase cells is shown (•).

A', B': Mean chromosome number±SD after each treatment, calculated from the data shown in panels A and B (*Difference in SD, p<0.05, Bartlett's Test).

C: SKOV-3 cells were transfected with control ASO alone or with olaparib or BRCA2 ASO alone or with olaparib. Forty-eight hours post-olaparib, cells were processed to yield metaphase spreads. FISH was performed for chromosomes X, 3, and 16. The number of translocation events in these chromosomes was counted and graphed. Mean numbers of translocations for each treatment are shown as bars (-).*Mean number of translocations were significantly different (p<0.05, Welch's t-test). Data from representative experiments are shown. All experiments were repeated at least once.

Figure 27:
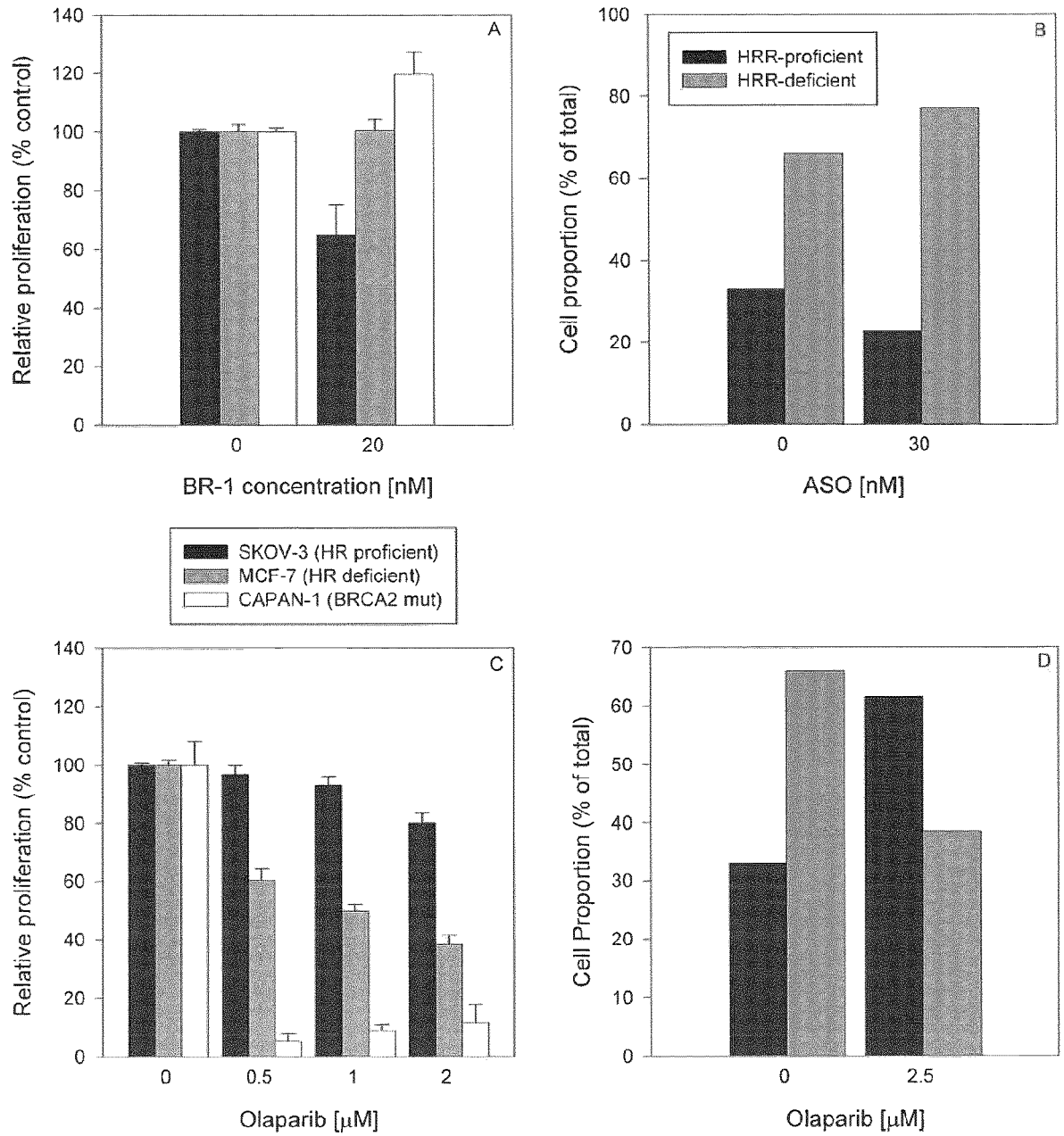

FIG. 27 illustrates that single treatment with BRCA2 ASO or olaparib has the potential to select for HRR-deficient or HRR-proficient cells, respectively.

A: BRCA2-wild type SKOV-3 cells (black bars), HRR-deficient MCF-7 cells (white bars), and BRCA2-mutated CAPAN-1 cells (grey bars) were treated simultaneously but separately with BRCA2 ASO (20 nM). Due to differing growth medium requirements and to avoid fluorescent label-induced changes in drug sensitivity, cells were not co-cultured. They were treated independently, at the same time with the same materials. Ninety-six hours post-transfection, cells were counted and proliferation determined (% of proliferation after control ASO treatment).

B: The theoretical proportions of a mixed cell population (HRR-proficient SKOV-3+MCF-7, and HRR-deficient CAPAN-1) following BRCA2 ASO treatment were calculated using the experimental data shown in panel A.

C: SKOV-3, MCF-7 and CAPAN-1 cells were treated with two different concentrations of olaparib for 96 hours. After drug treatment they were counted and proliferation was determined as a percent of that of vehicle-treated cells.

D: The theoretical proportions of a mixed cell population (HRR-proficient SKOV-3+MCF-7, and HRR-deficient CAPAN-1) following BRCA2 ASO treatment were calculated based on the experimental data shown in panel C.

Data from representative experiments are shown. All experiments were repeated at least once.

Figure 28:
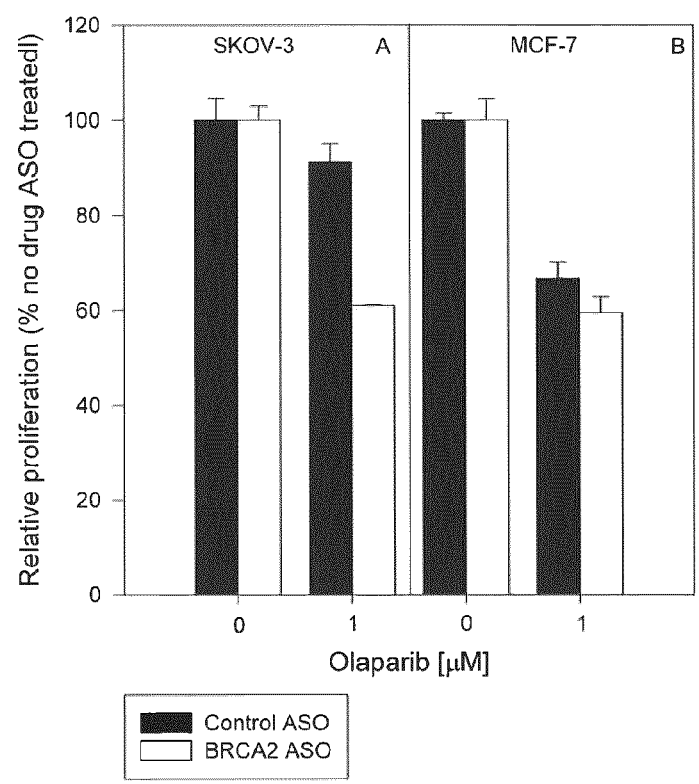

FIG. 28 illustrates combined BRCA2 ASO and olaparib treatment decreases the proliferation of both HRR-deficient and HRR-proficient cells. BRCA2-wild type SKOV-3 cells (A) and HRR-deficient MCF-7 cells (B) were transfected with control ASO (black bars) or BRCA2 ASO (white bars) and treated with vehicle or olaparib (1 µM). Proliferation was determined using cell counting 96 hours post-transfection.

Data from representative experiments are shown. All experiments were repeated at least once.

Figure 29:
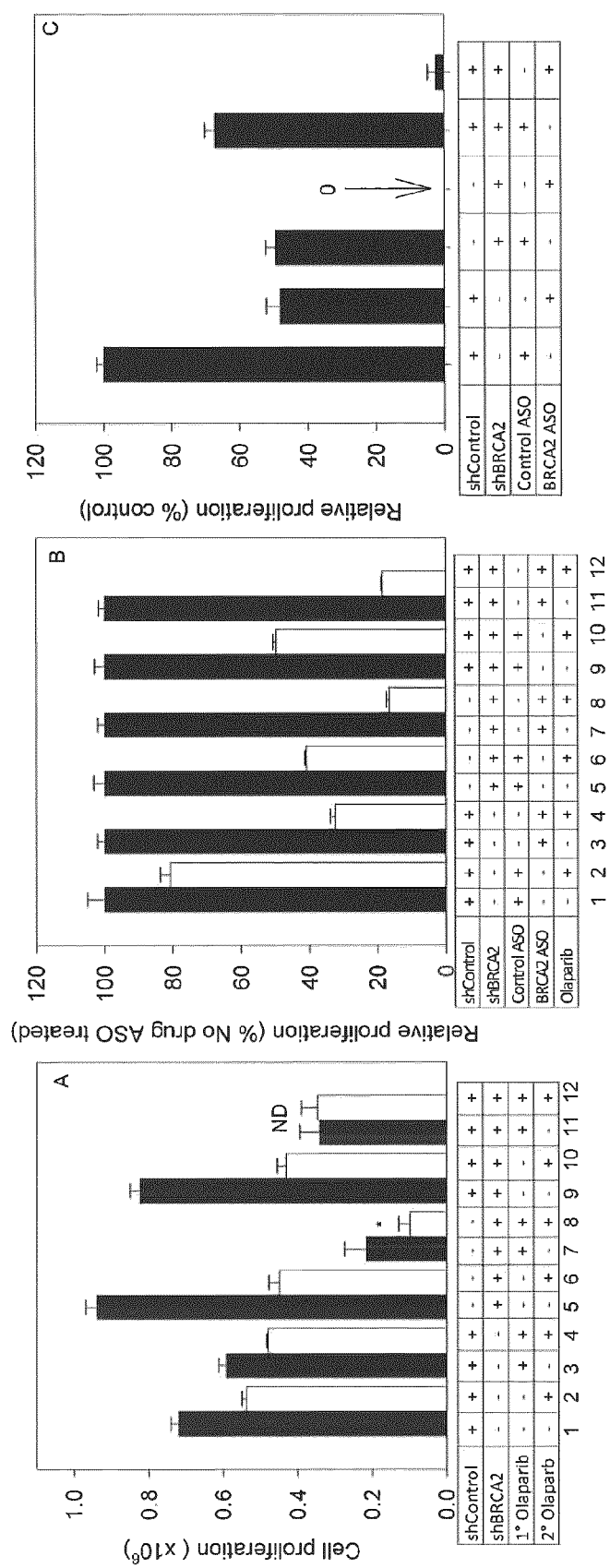

FIG. 29 illustrates combined BRCA2 ASO and olaparib treatment prevents outgrowth of resistant cells in a tumor cell population heterogeneous for HRR-proficiency.

A: SKOV-3$^{shBRCA2}$ cells (low BRCA2) were mixed with SKOV-3$^{shControl}$ cells (high BRCA2) at a 3:1 ratio, resulting in a primarily HRR-deficient mixed cell population. Parental and mixed populations were treated for the first time with olaparib (1° olaparib, 2.5 µM) or vehicle. Cells were re-plated at equal density 96 hours post-treatment. Parental and mixed populations were then treated a second time with olaparib (2° olaparib, 2.5 µM) or control vehicle. Ninety-six hours post-treatment, proliferation for all groups was determined based on cell counts and seeding density following 1° olaparib or vehicle treatment. White bars: 2° olaparib. Black bars: no 2° olaparib.

B: SKOV-3$^{shBRCA2}$ cells (low BRCA2), SKOV-3$^{shControl}$ cells (high BRCA2), and a mixed cell population (3:1, low BRCA2:high BRCA2) were transfected with control ASO or BRCA2 ASO followed by treatment with vehicle or olaparib (2.5 µM). Proliferation (percent of control ASO-treated cells) was determined 96 hours post-transfection. White bars: 2° olaparib. Black bars: no 2° olaparib.

C: SKOV-3$^{shBRCA2}$ cells (low BRCA2), SKOV-3$^{shControl}$ cells (high BRCA2), and a mixed cell population (3:1, low BRCA2:high BRCA2) previously treated with ASO (control or BRCA2) and olaparib (2.5 µM) were re-plated at the same density and allowed to proliferate without further treatment. Data from representative experiments are shown. All experiments were repeated at least once.

Figure 30:
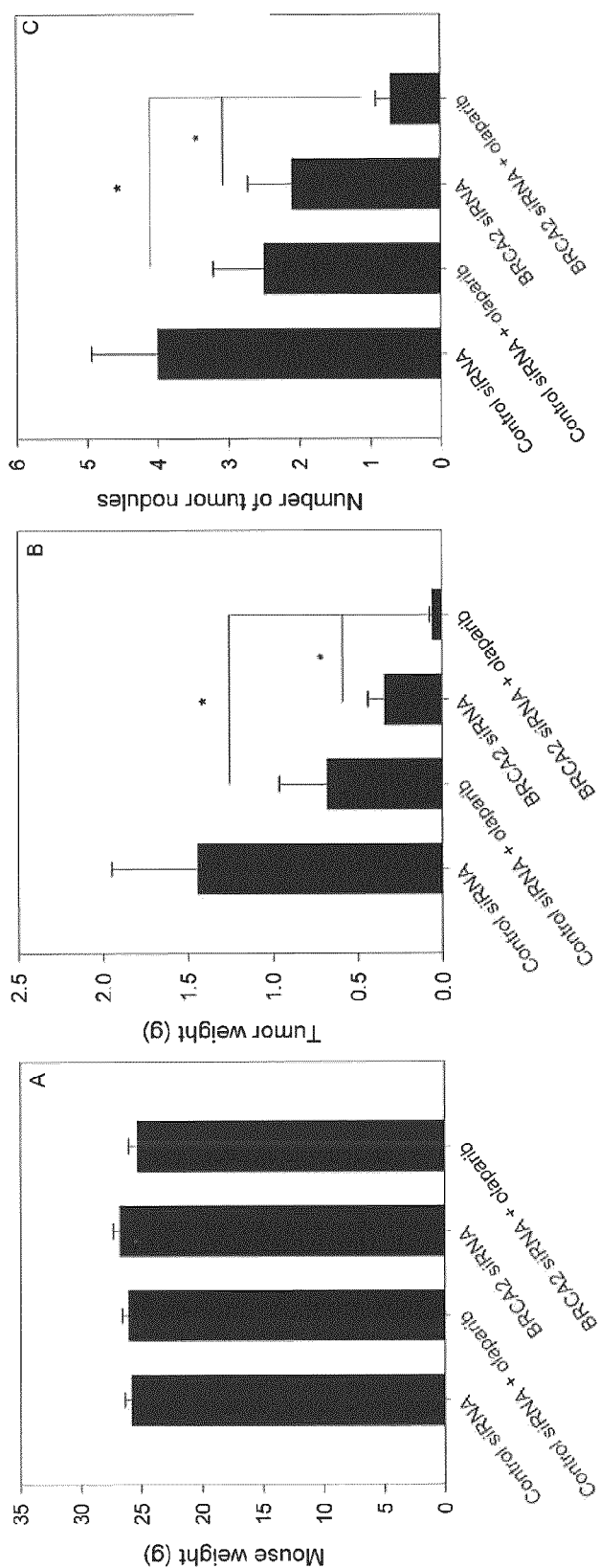

FIG. 30 illustrates that BRCA2 inhibition sensitizes ovarian cancer tumours to olaparib treatment in vivo. Female athymic nude mice were injected with $1.0 \times 10^6$ SKOV3-IP1 cells i.p. Mice were treated 7 days later with olaparib (5 mg/kg 5 days a week i.p.) and either control or BRCA2 siRNA twice per week encapsulated in DOPC-liposomes (150 µg/kg) (N=40, 10 animals per group). Once the mice in any group were moribund, the animals were weighed (A) and euthanized. The tumour weight (B) and number of tumour nodules (C) were determined (p*<0.05, Student's t-test).

Figure 31:
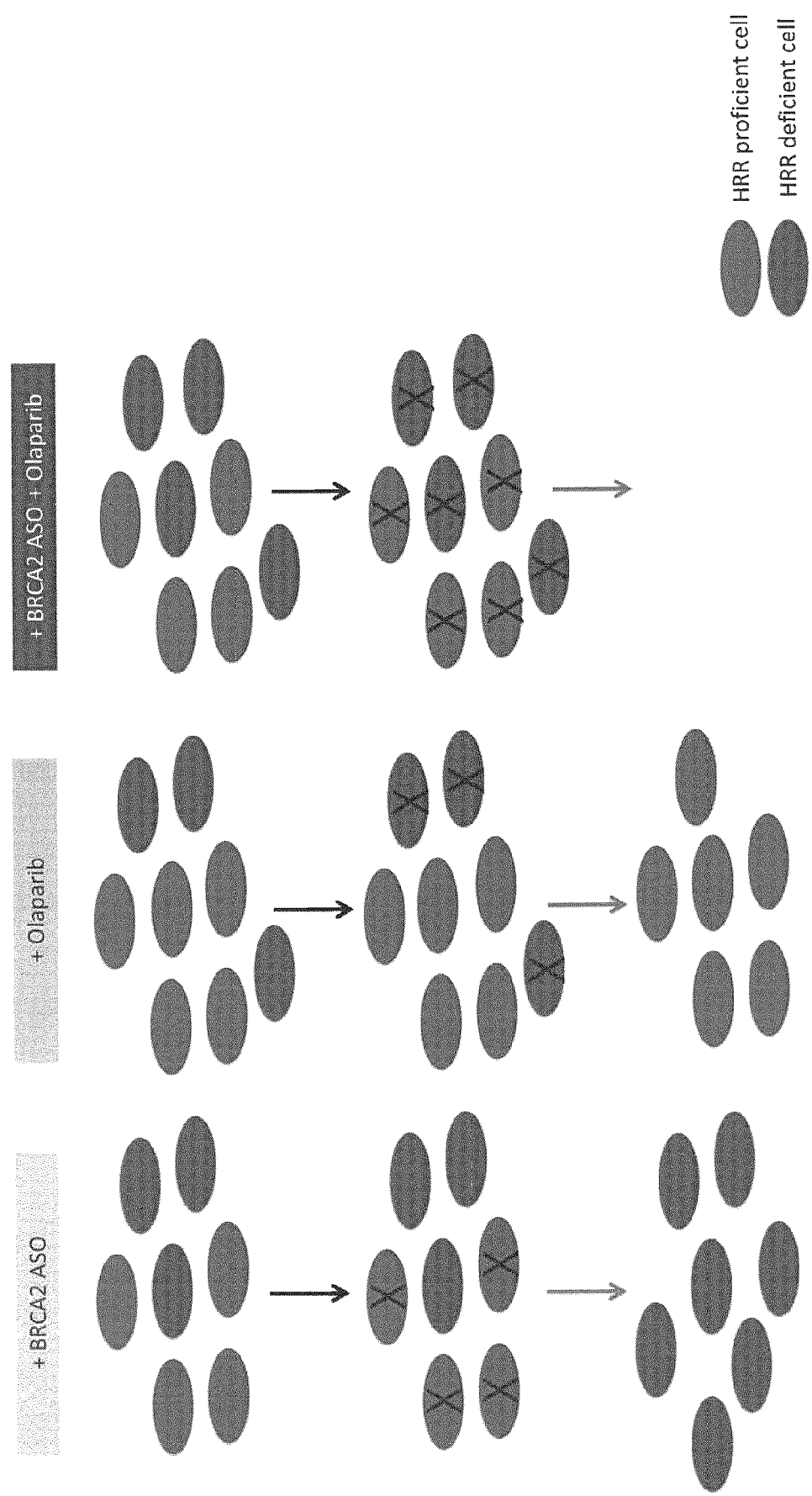

FIG. 31 illustrates reciprocal positive selection for weakness. In a population heterogeneous for HRR-proficiency, BRCA2 ASO treatment will impair the growth of HRR-proficient cells and select for HRR-deficient cells. Olaparib treatment will accomplish the reciprocal of that by impairing the growth of HRR-deficient cells while selecting for HRR-proficient cells. Therefore, each treatment selects for cells that are susceptible to the other treatment. When BRCA2 ASO and olaparib treatment is combined, both HRR-proficient and HRR-deficient cells are affected, nullifying selection based on HRR-proficiency.

Figure 32:
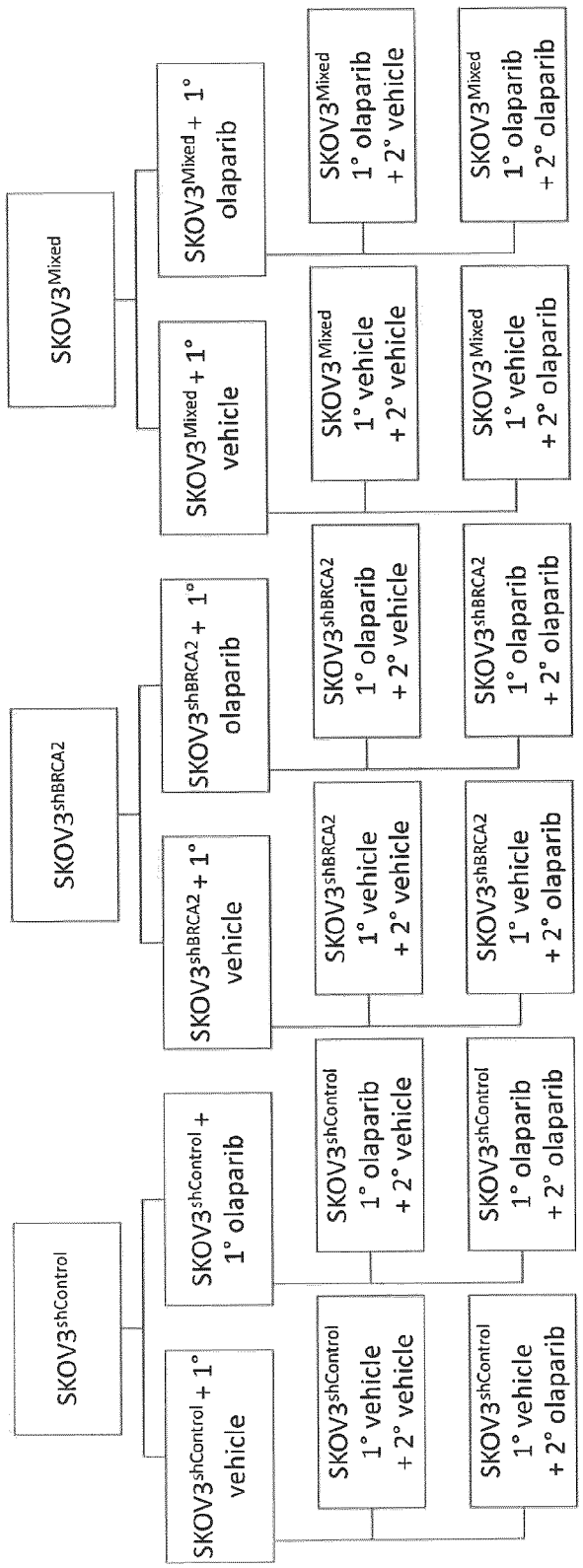

FIG. 32 is a schematic for mixed cell experiments. The mixed cell population, as well as the unmixed populations were treated according to the experimental schematic. The experiment was conducted in a serial and continuous fashion, such that all treatment groups and cell populations were in culture for the same amount of time, and all controls were exposed to the same conditions.

Figure 33:
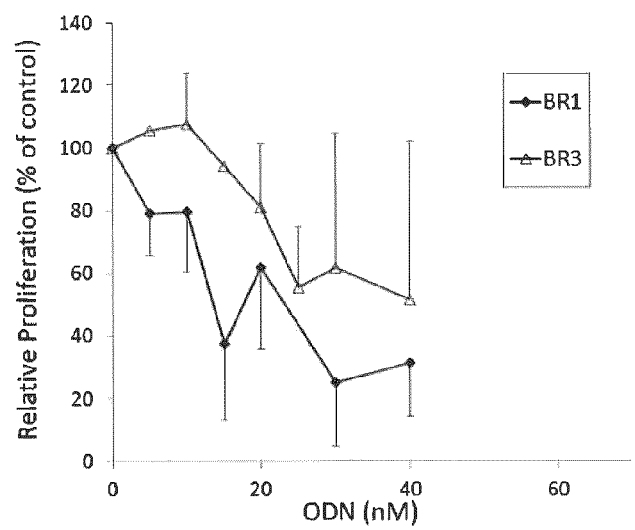

FIG. 33 illustrates that BR1 ASO and BR3 ASO are antiproliferative on their own, as single agents, in A549 NSCLC cells: Anti-BRCA2 ASOs targeting the mRNA coding region (BR1) and 3'-UTR (BR3) inhibit proliferation of human non-small cell lung cancer A549 cells in a concentration-dependent manner.

Figure 34:
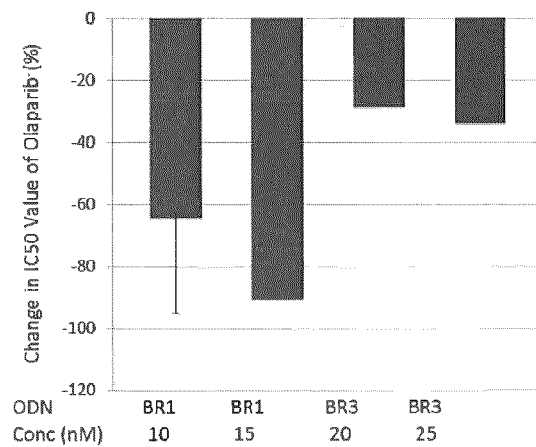

FIG. 34 illustrates that BR1 and BR3 ASOs enhance olaparib in A549 NSCLC cells. Anti-BRCA2 antisense ASOs BR1 and BR3 enhanced inhibition of proliferation of human non-small cell lung cancer A549 cells by olaparib by up to 95%. A549 cells were treated with ASO for 4 h, followed by addition of one volume of medium. After 20 h, medium was replaced with fresh medium±cisplatin and without ASO. Cells were then incubated for 4 d. Cell number was determined using a particle counter, and proliferation was calculated as a percent of ASO-treated, non-drug-treated control. The enhancement of drug toxicity caused by pre-incubation with ASO was determined by calculating the % decrease in the IC$_{50}$ value.

Figure 35:
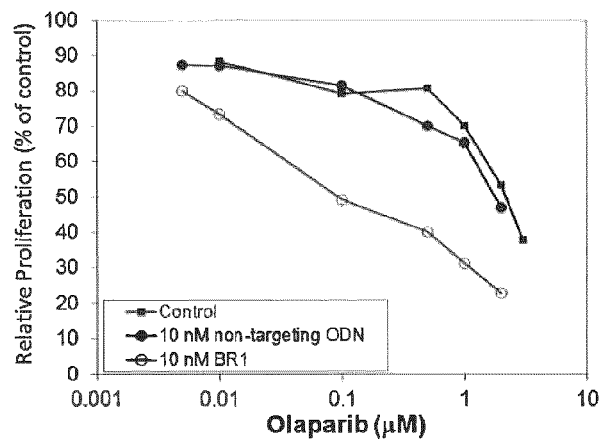

FIG. 35 illustrates that BR1 ASO enhances olaparib in A549 NSCLC cells. Anti-BRCA2 antisense ASO BR1 enhanced inhibition of proliferation of human non-small cell lung cancer A549 cells by olaparib by up to 95%. Cells were treated with ASO for 4 h followed by addition of one volume of medium. After 20 h, medium was replaced with fresh medium±cisplatin and without ASO. Cells were then incubated for 4 d. Cell number was determined using a particle counter and proliferation was calculated as a percent of ASO-treated, non-drug-treated control. The enhancement of drug toxicity caused by pre-incubation with ASO was determined by calculating the % decrease in the IC$_{50}$ value.

Figure 36:
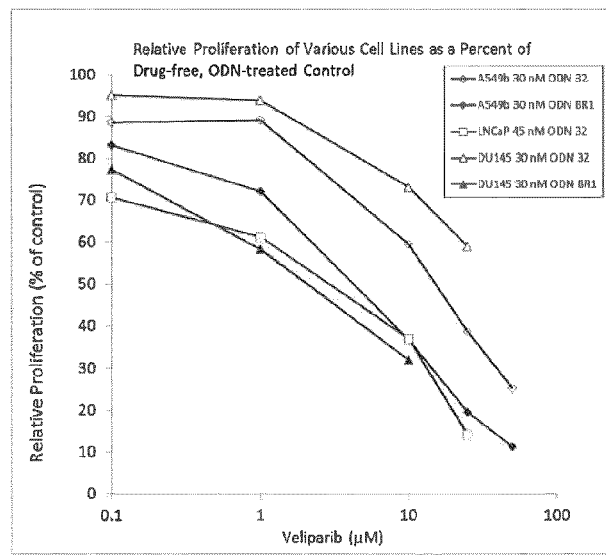

FIG. 36 illustrates that BR1 ASO enhances veliparib in A549 NSCLC cells: Cells were treated for 4 hours with BR1 ASO (ODN BR1) or non-targeting control ASO (ODN 32), after which one volume of medium was added and cells incubated for an additional 20 hours. ASO-containing medium was removed and replaced with fresh medium. Cells were then incubated for 4 days and cell numbers assessed. Proliferation in cells treated with BR1 was calculated as a percent of non-targeting ASO-treated controls. Initial cell density varied among cell lines. "A549b"="A549.

Figure 37:
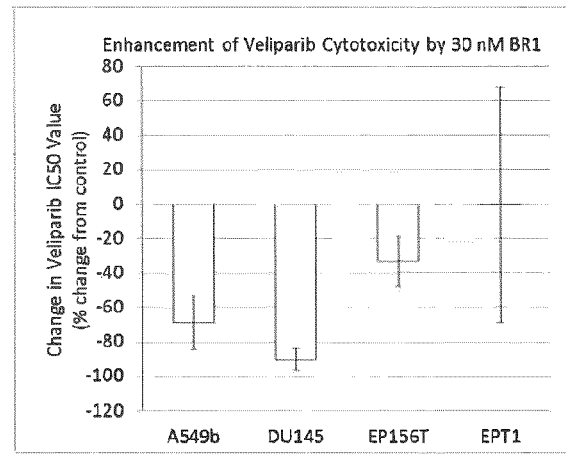

FIG. 37 illustrates that BR1 enhances veliparib in A549 human NSCLC cells and DU145 human prostate cancer cells, but little or not at all in EP156T primary prostate epithelial cells (non-tumorigenic) and EPT1 prostate epithelial cells (EP156T cells that had undergone epithelial to mesenchymal transition but were not able to sustain growth in soft agar: i.e., prostate epithelial cells that had undergone some aspects of malignant transformation but had not undergone the critical changes to full malignant transformation).

Figure 38:
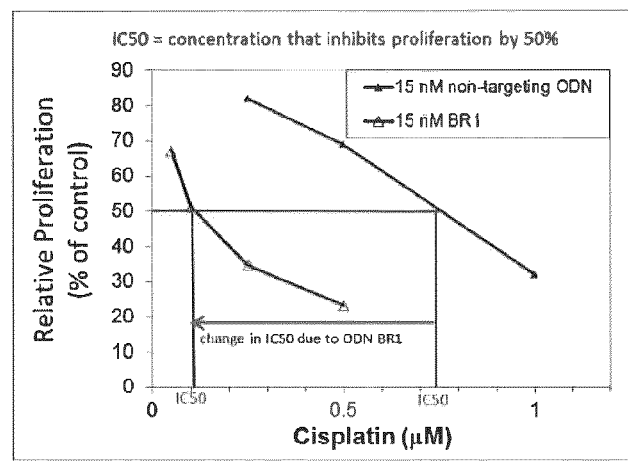

FIG. 38 illustrates that BR1 ASO enhances cisplatin in A549 NSCLC cells. The concentration of drug that inhibited proliferation by 50% (the $IC_{50}$) was used as the benchmark for comparison between treatments. Non-small cell lung cancer cell line A549 cells were treated with ASO for 4 h, followed by addition of one volume of medium. After 20 h, medium was replaced with fresh medium±cisplatin or olaparib, without ASO. Cells were then incubated for 4 d. Cell number was determined using a particle counter and proliferation in cells treated with BR1 was calculated as a percent of ASO-treated, non-drug-treated control. The enhancement of drug toxicity caused by pre-incubation with ASO was determined by calculating the % decrease in the $IC_{50}$ value.

Figure 39:
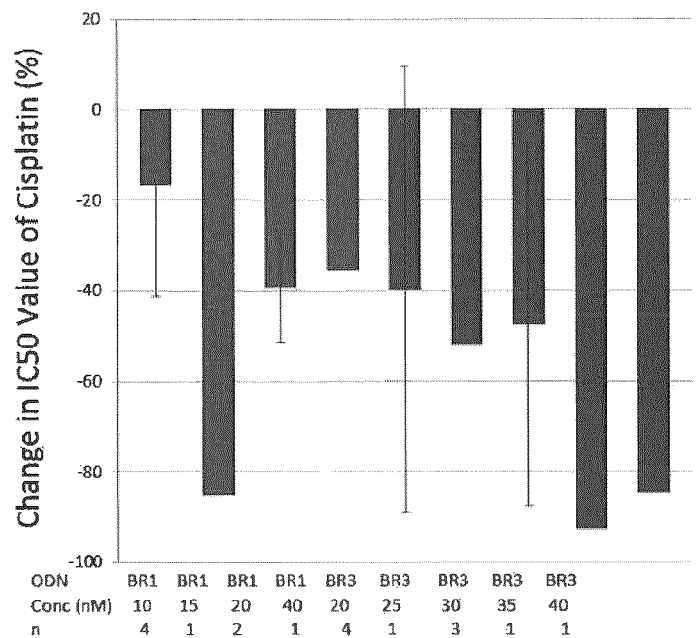

FIG. 39 illustrates that BR1 and BR3, as single agents, enhance cisplatin in A549 NSCLC cells. Anti-BRCA2 antisense ASOs BR1 and BR3 enhanced inhibition of proliferation of A549 cells by cisplatin by up to 85%. All bars are normalized to the inhibition of proliferation caused by the ASOs alone, which varied from 20-75%. Non-small cell lung cancer cell line A549 cells were treated with ASO for 4 h, followed by addition of one volume of medium. After 20 h, medium was replaced with fresh medium±cisplatin, without ASO. Cells were then incubated for 4 d. Cell number was determined using a particle counter and proliferation of cells treated with BR1 or BR3 was calculated as a percent of ASO-treated, non-drug-treated control. The enhancement of drug toxicity caused by pre-treatment with ASO was determined by calculating the % decrease in the $IC_{50}$ value.

Figure 40:
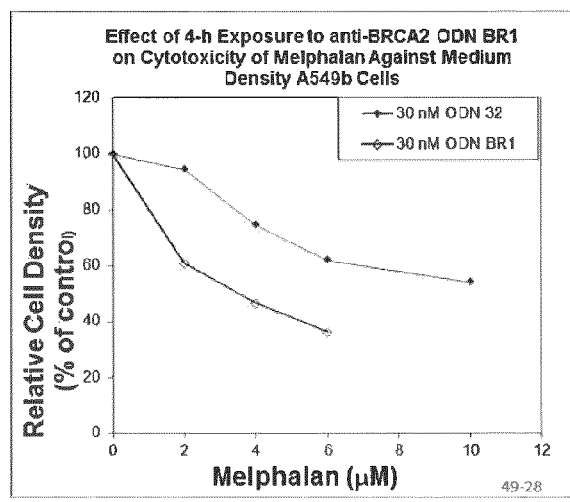

FIG. 40 illustrates that BR1 ASO enhances melphalan in A549 NSCLC cells. BR1 ASO (30 nM) enhanced cytotoxicity of melphalan in A549 cells. ODN 32 is a non-targeting control ASO. Cells were treated for 4 hours with ASO, after which one volume of medium was added and cells were incubated for an additional 20 hours. ASO-containing medium was removed and replaced with fresh medium. Drug was added to the final concentration indicated. Cells were then incubated for 4 days and cell numbers assessed. Proliferation in cells treated with BR1 was calculated as a percent of proliferation in non-drug-treated controls.

Figure 41:
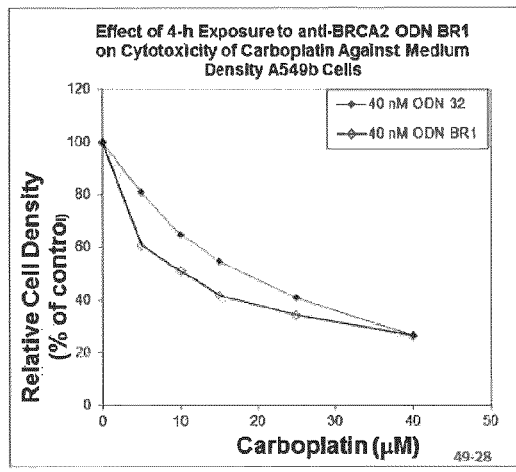

FIG. 41 illustrates that BR1 ASO enhances carboplatin in A549 NSCLC cells. BR1 ASO (40 nM) enhanced cytotoxicity of carboplatin in A549 cells. ODN 32 is a non-targeting control ASO. Cells were treated for 4 hours with ASO, after which one volume of medium was added, and cells were further incubated for 20 hours. ASO-containing medium was removed and replaced with fresh medium. Drug was added to the final concentration indicated. Cells were then incubated for 4 days and cell numbers assessed. Proliferation in BR1-treated cells was calculated as a percent of proliferation of non-drug-treated controls.

Figure 42:
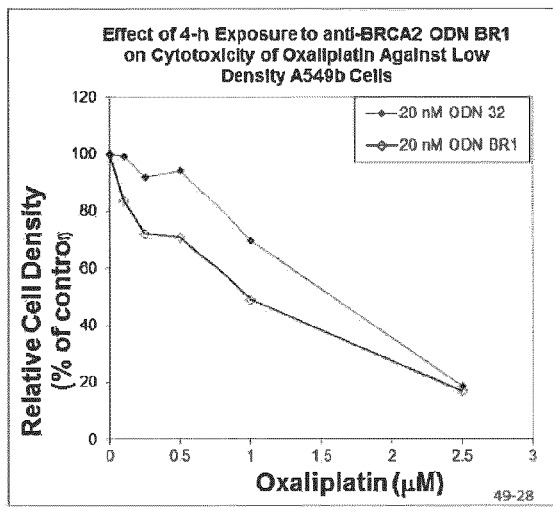

FIG. 42 illustrates that BR1 ASO enhances oxaliplatin in A549 NSCLC cells. BR1 ASO (20 nM) enhanced cytotoxicity of oxaliplatin in A549 cells. ODN 32 is a non-targeting control ASO. Cells were treated for 4 hours with ASO, after which one volume of medium was added and cells were incubated for a further 20 hours. ASO-containing medium was removed and replaced with fresh medium. Drug was added to the final concentration indicated. Cells were then incubated for 4 days and cell numbers assessed. Proliferation of BR1-treated cells was calculated as a percent of proliferation of non-drug-treated controls.

Figure 43:
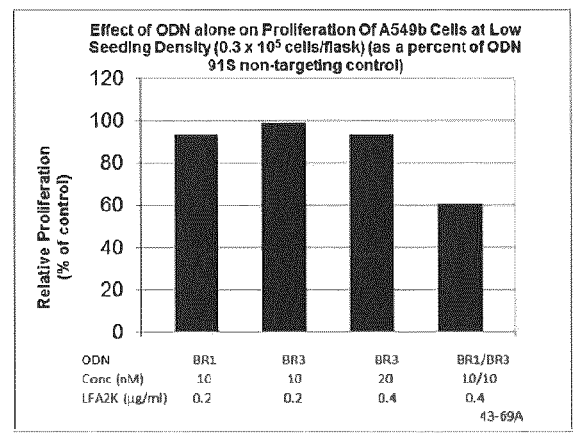

FIG. 43 illustrates that BR1 ASO is synergistic with BR3 in A549 NSCLC cells. Cells were treated for 4 hours with ASO, after which one volume of medium was added and cells were incubated for a further 20 hours. ASO-containing medium was removed and replaced with fresh medium. Cells were then incubated for 4 days and cell numbers assessed. Proliferation of BR1-treated cells was calculated as a percent of proliferation of non-targeting ASO-treated controls. LFA2K is the liposomal agent used to transfect ASOs into recipient cells.

Figure 44:
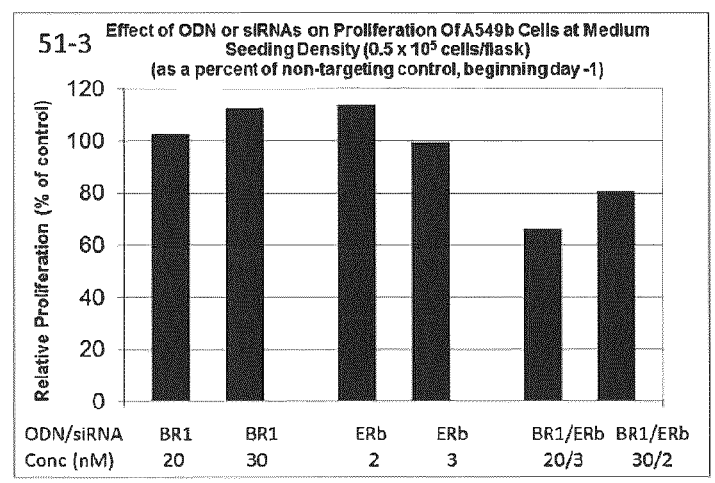

FIG. 44 illustrates BR1 ASO is synergistic with antisense siRNA targeting ERCC1 mRNA in A549 NSCLC cells. "ERb" is an siRNA directed against ERCC1 mRNA. ERCC1 participates in nucleotide excision repair, one of multiple DNA repair pathways. ERb siRNA was combined with BR1 ASO and compared with appropriate combination controls of ASO and siRNA.

Figure 45:
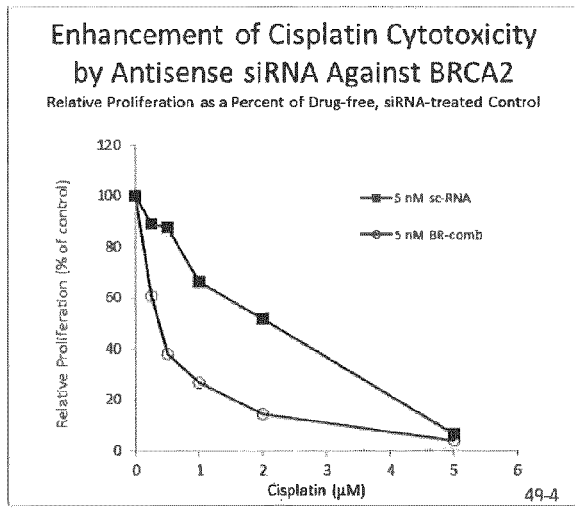

FIG. 45 illustrates that BRCA2 siRNA enhances cisplatin in A549 NSCLC cells: A combination of 4 anti-BRCA2 siRNAs (BR-comb, 5 nM total) enhanced cytotoxicity of cisplatin in A549 cells compared to the effect of control, non-targeting siRNA (sc-RNA, 5 nM). Cells were treated for 4 hours with siRNA, after which one volume of medium was added and cells were incubated for a further 20 hours. siRNA-containing medium was removed and replaced with fresh medium. Drug was added to the final concentration indicated. Cells were then incubated for 4 days and cell numbers assessed. Proliferation of BR1-treated cells was calculated as a percent of proliferation of non-drug-treated controls.

Figure 46:
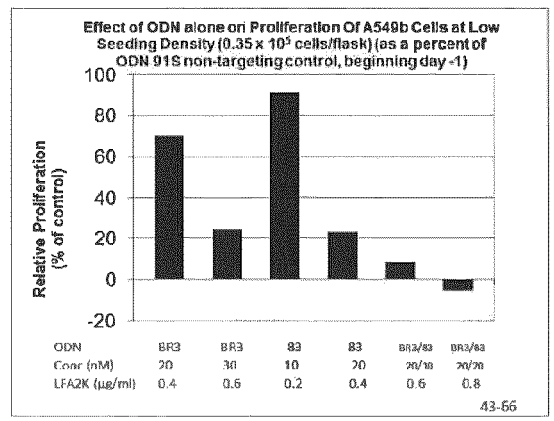

FIG. 46 illustrates that BR3 is antiproliferative on its own and synergistic with SARI-083 in A549 NSCLC cells: Combinations of BR3 ASO and anti-thymidylate synthase SARI-083 ASO caused greater-than-additive inhibition of proliferation compared to the effect of each ASO alone. Cells were treated for 4 hours with ASO after which one volume of medium was added and cells incubated for a further 20 hours. ASO-containing medium was removed and replaced with fresh medium. Cells were then incubated for 4 days and cell numbers assessed. Proliferation of BR3-treated cells was calculated as a percent of proliferation of non-targeting ASO-treated controls.

Figure 47:
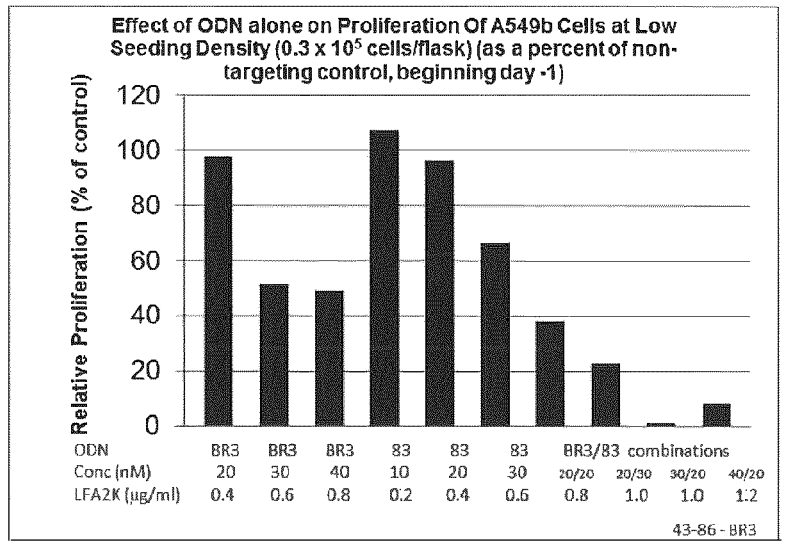

FIG. 47 illustrates that BR3 ASO is antiproliferative on its own and synergistic with SARI-083 in A549 NSCLC cells. Combinations of ASO BR3 and SARI-083 induced greater-than-additive inhibition of proliferation compared to inhibition of proliferation by each ASO alone. Cells were treated for 4 hours with ASO after which one volume of medium was added and cells incubated for a further 20 hours. ASO-containing medium was removed and replaced with fresh medium. Cells were then incubated for 4 days and cell numbers assessed. Proliferation of BR3-treated cells was calculated as a percent of proliferation of non-targeting ASO-treated controls.

Figure 48:
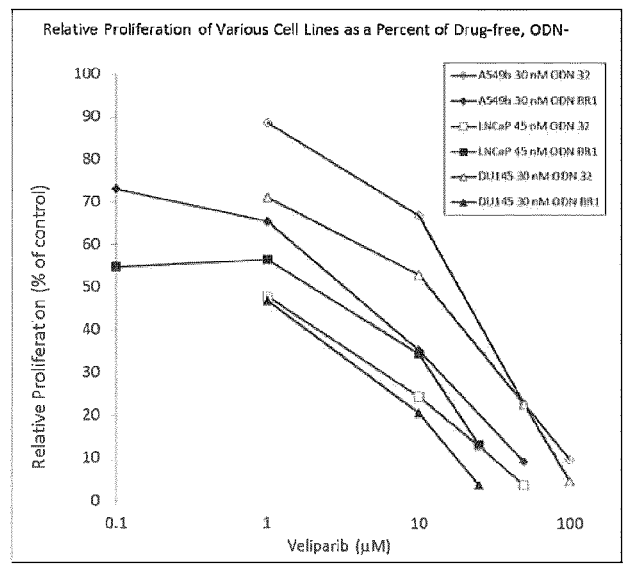

FIG. 48 illustrates that BR1 ASO enhances veliparib in DU145 human prostate cancer cells (but not LNCaP human prostate cancer cells). Cells were treated for 4 hours with ASO, after which one volume of medium was added and cells were incubated for a further 20 hours. ASO-containing medium was removed and replaced with fresh medium. Cells were then incubated for 4 days and cell numbers assessed. Proliferation of BR1-treated cells was calculated as a percent of proliferation of non-targeting ASO-treated control cells. Initial cell density varied among cell lines. BR1, at the concentrations used in this experiment, enhanced cytotoxicity of veliparib by 5- to 10-fold against A549b and DU145, but enhanced it very little against LNCAP.

Figure 49:
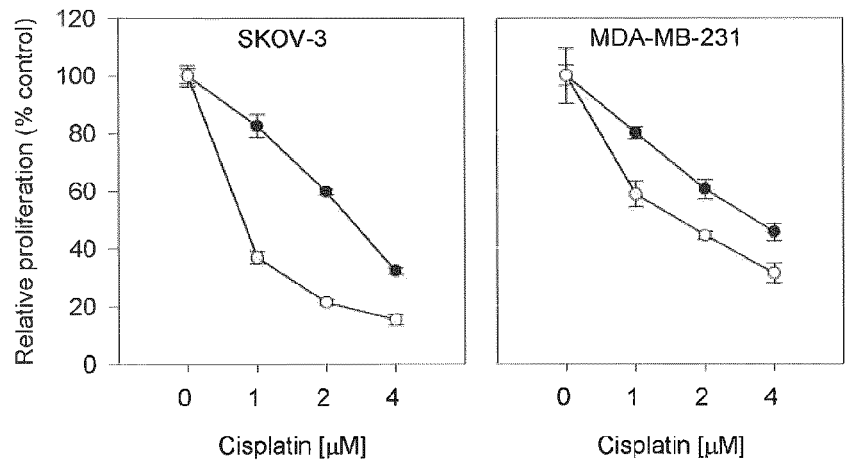

FIG. 49 illustrates that BR-1 (BRCA2 ASO) enhances the antiproliferative activity of cisplatin in SKOV-3 human ovarian cancer cells and MDA-MB-231 human breast cancer cells.

Figure 50:
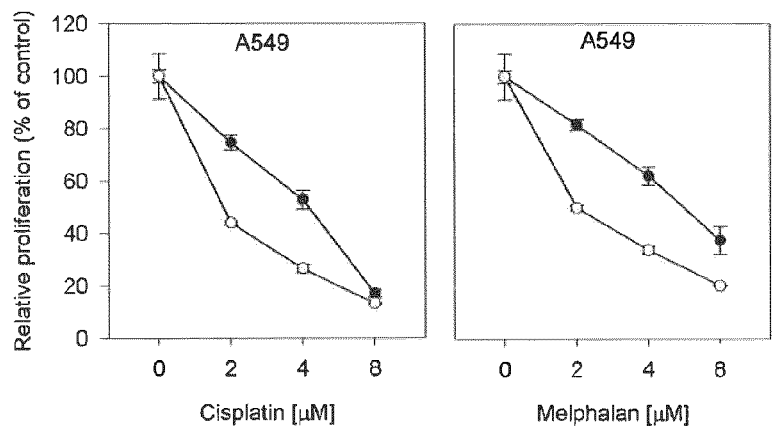

FIG. 50 illustrates that BR-1 (BRCA2 ASO) enhances the antiproliferative activity of cisplatin or melphalan in A549 human non-small cell lung cancer cells.

Figure 51:
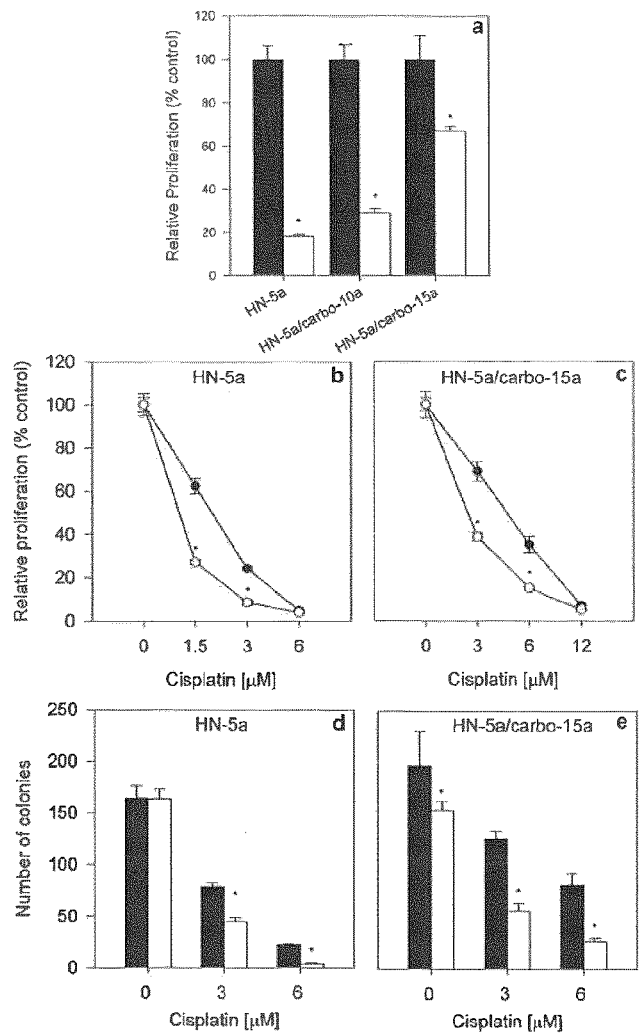

FIG. 51: BR-1 (BRCA2 ASO) reverses acquired cisplatin resistance in human head and neck cancer cells. HN-5a cells are parental, cisplatin-sensitive human head and neck squamous carcinoma cells, and HN-5a/carbo-10a and HN-5a/carbo-15a cells are cisplatin-resistant lines derived from HN-5a cells (Ferguson et al., Drug Metab. Dispos. 27:1399-1405, 1999). Cells were exposed to cisplatin and effects on proliferation were assessed 72 h after drug treatment. HN-5a cells (b) and HN-5a/carbo-15a cells (c) were transfected with control (black circles) or BRCA2 (white circles) ASO, treated with varying concentrations of cisplatin and then counted 96 h post-transfection. HN-5a cells (d) and HN-15a cells (e) were transfected with control or BRCA2 ASO, treated with different concentrations of cisplatin for 6 h, and then re-plated at a density of 500 cells per well to determine colony forming ability. *Different from cells treated with control ASO using a Student's t-test ($p<0.05$).

Figure 52:
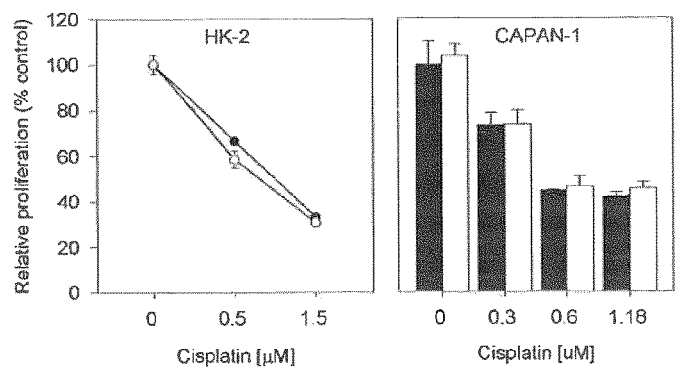

FIG. 52 illustrates that BR-1 (BRCA2 ASO) has no effect on the antiproliferative activity of cisplatin in non-tumor, immortalized human kidney proximal tubule-derived HK-2 cells or human pancreatic cancer CAPAN-1 cells with mutated, non-functional BRCA2

DETAILED DESCRIPTION OF THE INVENTION

The present invention provides for methods of treating cancer using antisense based therapies targeted against nucleic acids that encode proteins involved in the repair of double-stranded DNA breaks (DSBs), such as BRCA2, BRCA1, RAD51, PALB2 and DNA-PK. The antisense based therapies include but are not limited to including RNAi therapies, siRNA therapies and traditional antisense oligonucleotide therapies.

The antisense based therapies can be used in the treatment of cancer as single agents (including the use of combinations of the antisense oligonucleotides or siRNAs) or they may be used in combination with other cancer therapies.

As is known in the art, a number of cancer therapies act by damaging DNA and/or impairing DNA repair or synthesis. Resistance to such therapies may arise due to the ability of the cells to repair the DNA damage via various DNA repair pathways and/or DNA synthesis. One embodiment of the present invention, therefore, provides for the use of the antisense based therapies in combination with a cancer therapy that damages DNA and/or inhibits DNA repair or synthesis. Without being limited by any particular theory, the efficacy of such combinations may be due to the fact that cancer cells in general appear to have an inherently higher mutation rate than normal cells and are thus more dependent on DNA repair than normal cells. Many types of cancer cells also have defects in their mechanisms for repairing DNA damage. As such, cancer cells are likely to be more vulnerable than normal cells both to DNA damaging agents and to inhibitors of those remaining DNA repair or synthesis pathways which are still functional. Accordingly, treatment of cancer patients with antisense based therapies including antisense oligonucleotides and siRNA that target proteins involved in repairing double-strand DNA breaks can result inhibition of cancer cell growth and/or proliferation and also in enhanced cytotoxicity of therapies that induce DNA damage in cancer cells or that inhibit alternative DNA repair pathways or DNA synthesis pathways. Normal, non-cancerous cells, however, should be able to repair the DNA damage and thus survive treatment. Furthermore, enhancement of the anti-cancer activity of cancer therapies such as DNA-damaging agents could lead to the use of lower concentrations of the agents to achieve the same results, which in turn would decrease common toxicities related to the use of these agents.

In accordance with one embodiment of the invention, antisense based therapies targeted to a nucleic acid encoding a DNA DSB repair protein are used to induce a decrease in expression in the targeted protein thereby increasing the genetic instability in the cancer cell beyond a threshold over which the cancer cells are no longer viable. Accordingly, the methods provided by the present invention are applicable to a wide variety of cancers.

In accordance with one embodiment of the invention, antisense based therapies targeted to a nucleic acid encoding a DNA DSB repair protein are used to induce a decrease in expression in the targeted protein in a patient allowing the patient to obtain greater benefit from treatment with a DNA damaging agent and/or an inhibitor of DNA repair or synthesis. Accordingly, the methods provided by the present invention are applicable to a wide variety of cancers.

In accordance with one embodiment of the invention, antisense based therapies are therapies used to induce a synthetic lethality in cancer cells.

In accordance with one embodiment of the invention, antisense based therapies are used to sensitize cancer cells to chemotherapeutics that target the synthetic lethal partner of the antisense based therapy target. In one embodiment, the antisense based therapy targets BRCA2 while the chemotherapeutic targets PARP1.

In accordance with one embodiment of the invention, antisense oligonucleotides targeted to a nucleic acid encoding a DNA DSB repair protein are used to induce a decrease in expression in the targeted protein in a patient, thus creating or mimicking a "synthetic lethal" situation and allowing the patient to obtain greater benefit from treatment with a DNA damaging agent and/or an inhibitor of DNA repair or synthesis.

In accordance with one embodiment, siRNA targeted to a nucleic acid encoding a DNA DSB repair protein are used to induce a decrease in expression in the targeted protein in a patient, thus creating or mimicking a "synthetic lethal" situation and allowing the patient to obtain greater benefit from treatment with a DNA damaging agent and/or an inhibitor of DNA repair or synthesis.

In certain embodiments, the invention encompasses the use of the antisense based therapies including antisense oligonucleotides and siRNA targeted to a nucleic acid encoding a DNA DSB repair protein in the treatment of cancers in which there is already a DNA repair defect. In these embodiments, the antisense oligonucleotide may target a DNA DSB repair protein in which there is already a partial defect, or it may target a DNA DSB repair protein belonging to the same or an alternative DNA repair pathway.

As an example, antisense oligonucleotides or siRNAs targeted to a nucleic acid encoding a BRCA2 protein are capable of inhibiting cancer cell growth and/or proliferation and of potentiating the anti-proliferative effects of drugs such as the PARP inhibitor, olaparib, and the platinum drug, cisplatin, as well as compounds (such as small molecules or antisense oligonucleotides) that inhibit thymidylate synthase (TS). Thus, in one embodiment of the invention, antisense oligonucleotides targeted to a nucleic acid encoding a DNA DSB repair protein are used in the treatment of cancer in combination with cancer therapies that result in DNA damage (such as platinum drugs, alkylating agents, and radiation), or that target a range of DNA repair pathways (such as PARP inhibitors). In another embodiment, antisense oligonucleotides targeted to a nucleic acid that encodes a DNA DSB repair protein are used in the treatment of cancer in combination with cancer therapies that impact DNA synthesis, for example anti-cancer agents that inhibit thymidylate synthase (TS). In another embodiment, antisense oligonucleotides targeted to a nucleic acid encoding a DNA DSB repair protein are used as single agents in the treatment of cancer.

Definitions

Unless defined otherwise, all technical and scientific terms used herein have the same meaning as commonly understood by one of ordinary skill in the art to which this invention belongs.

The term "antisense based therapies" as used herein, refers to a therapy comprising a sequence that is complementary to the mRNA transcribed from a target gene and can include antisense oligonucleotides, iRNA, and siRNA. In the context of the present invention, the target gene is the gene encoding a DNA DSB repair protein such as, for example, BRCA2 or RAD51.

The term "anti-proliferative" or "anti-proliferative activity", as used herein, means a reduction in total cell number in treated versus control. Antisense based therapies that have an anti-proliferative activity include those therapies that are cytotoxic, induce apoptosis, arrest or delay the cell cycle, alter cell size, or are a combination thereof.

The term "oligonucleotide," as used herein, means a polymeric form of nucleotides of at least 7 nucleotides in length comprising either ribonucleotides or deoxynucleotides or modified forms of either type of nucleotide. The term includes single and double stranded forms of DNA or RNA. In general, oligonucleotides are between about 7 and about 100 nucleotides in length. Oligonucleotide may also refer to gapmers or modified oligonucleotides. In some embodiments, the oligonucleotide is an antisense LNA™ Gapmer.

"Relative cell density" refers to the relative density of live cells at the end of an assay.

The term "selectively hybridize" as used herein refers to the ability of a nucleic acid molecule to bind detectably and specifically to a second nucleic acid molecule. Oligonucleotides selectively hybridize to target nucleic acid strands under hybridization and wash conditions that minimise appreciable amounts of detectable binding to non-specific nucleic acid molecules. High stringency conditions can be used to achieve selective hybridization conditions as known in the art and discussed herein.

Typically, hybridization and washing conditions are performed at high stringency according to conventional hybridization procedures. Washing conditions are typically 1-3× SSC, 0.1-1% SDS, 50-70° C. with a change of wash solution after about 5-30 minutes.

The term "corresponds to" as used herein with reference to nucleic acid sequences means a polynucleotide sequence that is identical to all or a portion of a reference polynucleotide sequence. In contradistinction, the term "complementary to" is used herein to mean that the polynucleotide sequence is identical to all or a portion of the complement of a reference polynucleotide sequence. For illustration, the nucleotide sequence "TATAC" corresponds to a reference sequence "TATAC" and is complementary to a reference sequence "GTATA".

The following terms are used herein to describe the sequence relationships between two or more polynucleotides: "reference sequence," "window of comparison," "sequence identity," "percent (%) sequence identity" and "substantial identity." A "reference sequence" is a defined sequence used as a basis for a sequence comparison; a reference sequence may be a subset of a larger sequence, for example, as a segment of a full-length cDNA, mRNA or gene sequence, or may comprise a complete cDNA, mRNA or gene sequence. Generally, a reference polynucleotide sequence is at least 20 nucleotides in length, and often at least 50 nucleotides in length.

A "window of comparison", as used herein, refers to a conceptual segment of the reference sequence of at least 15 contiguous nucleotide positions over which a candidate sequence may be compared to the reference sequence and wherein the portion of the candidate sequence in the window of comparison may comprise additions or deletions (i.e. gaps) of 20 percent or less as compared to the reference sequence (which does not comprise additions or deletions) for optimal alignment of the two sequences. The present invention contemplates various lengths for the window of comparison, up to and including the full length of either the reference or candidate sequence. In one embodiment, the window of comparison is the full length of the candidate sequence. Optimal alignment of sequences for aligning a comparison window may be conducted using the local homology algorithm of Smith and Waterman (*Adv. Appl. Math.* (1981) 2:482), the homology alignment algorithm of Needleman and Wunsch (*J. Mol. Biol.* (1970) 48:443), the search for similarity method of Pearson and Lipman (*Proc. Natl. Acad. Sci.* (U.S.A.) (1988) 85:2444), using computerised implementations of these algorithms (such as GAP, BESTFIT, FASTA, and TFASTA in the Wisconsin Genetics Software Package Release 7.0, Genetics Computer Group, 573 Science Dr., Madison, Wis.), using publicly available computer software such as ALIGN or Megalign (DNAS-TAR), or by inspection. The best alignment (i.e. resulting in the highest percentage of identity over the comparison window) is then selected.

The term "sequence identity" means that two polynucleotide sequences are identical (i.e. on a nucleotide-by-nucleotide basis) over the window of comparison.

The term "percent (%) sequence identity," as used herein with respect to a reference sequence is defined as the percentage of nucleotide residues in a candidate sequence that are identical with the residues in the reference polynucleotide sequence over the window of comparison after optimal alignment of the sequences and introducing gaps, if necessary, to achieve the maximum percent sequence identity, without considering any conservative substitutions as part of the sequence identity.

The term "substantial identity" as used herein denotes a characteristic of a polynucleotide sequence, wherein the polynucleotide comprises a sequence that has at least 50% sequence identity as compared to a reference sequence over the window of comparison. In various embodiments of the invention, polynucleotide sequences having at least 60% sequence identity, at least 70% sequence identity, at least 80% sequence identity, at least 90% sequence identity and at least 95% sequence identity as compared to a reference sequence over the window of comparison are considered to have substantial identity with the reference sequence.

The term "treatment," as used herein, refers to an intervention performed with the intention of improving a recipient's status. The improvement can be subjective or objective and is related to the amelioration of the symptoms associated with, preventing the development of, or altering the pathology of a disease, disorder or condition being treated. Thus, the terms therapy and treatment are used in the broadest sense, and include the prevention (prophylaxis), moderation, reduction, and curing of a disease, disorder or condition at various stages. Prevention of deterioration of a recipient's status is also encompassed by the term. Those in need of therapy/treatment include those already having the disease, disorder or condition as well as those prone to, or at risk of developing, the disease, disorder or condition and those in whom the disease, disorder or condition is to be prevented.

The term "ameliorate" or "amelioration" includes the arrest, prevention, decrease, or improvement in one or more the symptoms, signs, and features of the disease being treated, both temporary and long-term.

The term "subject" or "patient" as used herein refers to a mammal in need of treatment.

Administration of the compounds of the invention "in combination with" one or more further therapeutic agents, is intended to include simultaneous (concurrent) administration and consecutive administration. Consecutive administration is intended to encompass administration of the therapeutic agent(s) and the compound(s) of the invention to the subject in various orders and via various routes.

As used herein, the term "about" refers to an approximately +/−10% variation from a given value. It is to be understood that such a variation is always included in any given value provided herein, whether or not it is specifically referred to.

Target Proteins

Cells comprise distinct pathways for mediating the repair of different types of DNA damage. Such pathways include base excision repair, homologous recombination-dependent DNA double strand break (HR-DD) repair, non-homologous end-joining (NHEJ), nucleotide excision repair, and mismatch repair. HR-DD repair and NHEJ pathways are responsible for the repair of double strand DNA breaks (DSBs). Antisense based therapies according to the present invention target nucleic acids that encode proteins in the HR-DD or NHEJ pathways, both of which are involved in DNA DSB repair.

As used herein, the term "DNA DSB repair protein" refers to a protein involved in either the HR-DD pathway or the NHEJ pathway for repairing DNA DS breaks.

In one embodiment, antisense based therapies for use in accordance with the present invention are designed to target a nucleic acid encoding a DNA DSB repair protein, wherein the DNA DSB protein is involved in the HR-DD repair pathway. Non-limiting examples of key proteins that are involved in this pathway include, for example, BRCA1, BRCA2, PALB2 and RAD51. In one embodiment, antisense oligonucleotides or siRNAs for use in accordance with the present invention are designed to target a nucleic acid encoding the BRCA2 protein or the RAD51 protein.

In one embodiment, antisense based therapies for use in accordance with the present invention are designed to target a nucleic acid encoding a DNA DSB repair protein, wherein the DNA DSB protein is involved in the NHEJ repair pathway. One of the key proteins in this pathway is DNA-dependent protein kinase (DNA-PK), which includes a catalytic subunit, DNA-$PK_{CS}$, and a DNA-end binding heterodimer, Ku.

In one embodiment, antisense based therapies targeting BRCA2 are used to reverse resistance to chemotherapies acquired from BRCA reversion mutations in BRCA2 mutant cancers. In some embodiments, the site targeted by the antisense therapies is not the site of reversion, optionally pools of siRNA and/or antisense oligonucleotides are used.

In some embodiments, the antisense based therapies targets is designed to target BRCA2 reversion mutants that splice out mutation in exon 11 (for example positions 6174-6176).

In one embodiment, antisense based therapies targeting BRCA1 are used to reverse resistance to chemotherapies acquired from BRCA revision mutations in BRCA2 mutant cancers, optionally pools of siRNA and/or antisense oligonucleotides are used.

In one embodiment, antisense based therapies targeting BRCA2 are used to reverse resistance to chemotherapies acquired from BRCA revision mutations in BRCA1 mutant cancers, optionally pools of siRNA and/or antisense oligonucleotides are used.

Antisense Based Therapies
Selection and Characteristics

Antisense based therapies for use in accordance with the present invention are designed to target a nucleic acid encoding a DNA DSB repair protein. The sequences of the genes of various DNA DSB repair proteins involved in the HR-DD or NHEJ repair pathways are known in the art. For example, the sequence of the BRCA2 mRNA is available under GenBank™ Accession No. NM_000059.3 and the sequence of the BRCA2 gene is available under GenBank™ Accession No. NG_012772.1. Likewise, the sequences of the RAD51 mRNA (GenBank™ Accession No. NM_001164269.1), RAD51 gene (GenBank™ Accession No. NG_012120.1), BRCA1 mRNA (GenBank™ Accession No. NM_007294), BRCA1 gene (GenBank™ Accession No. NG_005905.2), PALB2 mRNA (GenBank™ Accession No. NM_024675.3), PALB2 gene, (GenBank™ Accession No. NG_007406.1), DNA-PK mRNA (GenBank™ Accession No. NM_001081640.1), and DNA-PK gene (GenBank™ Accession No. NG_023435.1) are also publicly available.

In targeting the antisense based therapies to the selected gene, a determination is made of a site or sites within this gene or its mRNA for the antisense interaction to occur such that the desired effect, for example, modulation of expression of the protein encoded by the gene and/or inhibition of cancer cell growth or proliferation, will result. Once the target site or sites have been identified, oligonucleotides are chosen that are sufficiently complementary (i.e. hybridize with sufficient strength and specificity) to the target to give the desired result.

Generally, antisense oligonucleotides can be targeted to the 5' untranslated region (5'-UTR), the translation initiation or start codon region, the coding sequence (or open reading frame (ORF)), the translation termination or stop codon region, or the 3' untranslated region (3'-UTR) of a gene. One embodiment of the present invention provides for antisense oligonucleotides targeted to the coding region or the 3'-UTR of the target mRNA.

The antisense oligonucleotides in accordance with the present invention are selected such that the antisense sequence exhibits the least likelihood of forming duplexes, hairpins or dimers, and contains minimal or no homooligomer/sequence repeats. The oligonucleotide may further contain a GC clamp. One skilled in the art will appreciate that these properties can be determined qualitatively using various computer modelling programs, for example, the program OLIGO® Primer Analysis Software, Version 5.0 (distributed by National Biosciences, Inc., Plymouth, Minn.).

In order to be effective, conventional antisense oligonucleotides are typically less than about 100 nucleotides in length, for example, between 7 and 100 nucleotides in length. In one embodiment of the present invention, the antisense oligonucleotides are less than about 50 nucleotides in length, for example between about 7 and about 50 nucleotides in length. In another embodiment, the antisense oligonucleotides are between about 10 and about 50 nucleotides in length. In a further embodiment, the antisense oligonucleotides are between about 12 and about 50 nucleotides in length. In other embodiments, the antisense oligonucleotides are less than about 35 nucleotides in length, for example between about 7 and about 35 nucleotides in length, between about 10 and about 35 nucleotides, between about 12 and about 35 nucleotides, or between about 15 and 35 nucleotides. In other embodiments, the antisense oligonucleotides are less than about 30 nucleotides in length, for example between about 15 and 30 nucleotides, or between about 12 and 30 nucleotides. In other embodiments, the antisense oligonucleotides are less than about 25 nucleotides in length, for example, between about 15 and 25 nucleotides, and between about 12 and about 25 nucleotides in length.

In one embodiment of the present invention, the antisense oligonucleotides are complementary to a portion of the mRNA transcribed from the BRCA2 gene. In another embodiment of the present invention, the antisense oligonucleotides are complementary to a portion of the coding region or the 3'-UTR of the BRCA2 mRNA.

In some embodiments, the antisense based therapy is small interfering RNA ("siRNA") (also referred to in the art as "short interfering RNAs"). Generally the siRNA is double stranded of about 10-50 nucleotides in length (the term "nucleotides" including nucleotide analogs), preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof). The smaller RNA segments then mediate the degradation of the target mRNA. Kits for synthesis of RNAi are commercially available from, e.g. New England Biolabsor Ambion. In one embodiment one or more of the chemistries described above for use in antisense RNA can be employed in molecules that mediate RNAi.

Examples of suitable target sequences within the BRCA2 gene or mRNA for the design of antisense oligonucleotides or siRNA are known in the art and additional examples are provided herein. For example, Dharmacon Inc. (Lafayette, Colo.) provides a number of siRNA sequences targeted to BRCA2 gene that could also serve as the basis for the design of antisense oligonucleotides. Examples of antisense oligonucleotide and siRNA sequences known in the art are provided in Table 1 below.

TABLE 1

Antisense Oligonucleotides and siRNA Sequences Targeted to BRCA2

| SEQ ID NO | Sequence | Origin |
|---|---|---|
| 4 | 5'-CAGCGTTTGTG TATCGGGCA-3' | International Patent Application Publication No. WO2008/043561 |
| 5 | 5'-TTGGATCCAAT AGGCAT-3' | J. Natl. Cancer Inst., 1998, Vol. 90, pp. 978-985 |
| 6 | 5'-TACGTACTCCA GAACATTTAA-3' | International Patent Application Publication No. WO2008/043561 |
| 7 | 5'-TTGGAGGAATA TCGTAGGTAA-3' | International Patent Application Publication No. WO2008/043561 |
| 8 | 5'-CAGGACACAAT TACAACTAAA-3' | International Patent Application Publication No. WO2008/043561 |
| 9 | 5'-UAAAUAGCAAG UCCGUUUC-3' | Dharmacon Inc. |
| 10 | 5'-UAAUGAAGCAU CUGAUACC-3' | Dharmacon Inc. |
| 11 | 5'-UAUUAAACCUG CAUUCUUC-3' | Dharmacon Inc. |
| 12 | 5'-GUAUCUCUUGA CGUUCCUUA-3' | Dharmacon Inc. |

In some embodiments, the antisense therapy targets:

| 5'-CCGATTACCTGTGTACCCT-3' | Sigma Aldrich |
|---|---|

In some embodiments, the antisense therapy is a siRNA comprising:

Sense Sequence:           CCGAUUACCUGUGUACCCUdTdT

Antisense Sequence        AGGGUACACAGGUAAUCGGdTdT

In some embodiments, the antisense therapy targets:
nucleotides 4284-4302 in coding sequence of cDNA of BRCA2 message, including 5'-UTR and 3'-UTR;
nucleotides 6188-6206 in coding sequence cDNA of BRCA2 message, including 5'-UTR and 3'-UTR;
nucleotides 1949-1967 in coding sequence of cDNA of BRCA2 message, including 5'-UTR and 3'-UTR;
nucleotides 7241-7259 in coding sequence cDNA of BRCA2 message, including 5'-UTR and 3'-UTR;
nucleotides 7211-7230 in coding sequence cDNA of BRCA2 message, including 5'-UTR and 3'-UTR.
nucleotides 7241-7259 in coding sequence cDNA of BRCA2 message, including 5'-UTR and 3'-UTR;
nucleotides 8574-8593 in coding sequence cDNA of BRCA2 message, including 5'-UTR and 3'-UTR;

fully within 3'-UTR bases 10615-10634, 131 bases downstream of the translation stop site.

In one embodiment, the antisense therapy targets the BRCA2 mRNA optionally the target sequence is bases 7212 to 7230 of GenBank Sequence ID: refNM_000059.3.

In one embodiment, the antisense based technologies including antisense oligonucleotides and siRNA for use in accordance with the present invention comprise a sequence that is complementary to a portion of the BRCA2 mRNA. In one embodiment, the antisense technologies for use in accordance with the present invention comprise a sequence that is identical or substantially identical to one of the sequences identified in Table 1 above. In one embodiment, the antisense technologies comprise a sequence that is complementary to a portion of the coding sequence of the BRCA2 mRNA. In another embodiment, the antisense technologies comprise a sequence that is complementary to a portion of the 3'-UTR of the BRCA2 mRNA. In one embodiment, the antisense oligonucleotide against BRCA2 is other than 5'-CAGCGTTTGTGTATCGGGCA-3' (SEQ ID NO:4). In another embodiment, the antisense oligonucleotide against BRCA2 is other than 5'-TTGGATCCAATAGGCAT-3' (SEQ ID NO:5).

Additional examples of suitable antisense oligonucleotides targeted to the BRCA2 mRNA include the following (see Example 1 provided herein):

```
                              (SEQ ID NO: 1)
5'-GUAUCUCUUGACGUUCCUUA-3'

(SEQ ID NO: 2)
5'-UACCAGCGAGCAGGCCGAGU-3'

(SEQ ID NO: 3)
5'-UGCCCGAUACACAAACGCUG-3'

(SEQ ID NO: 13)
5'-GTATCTCTTGACGTTCCTTA-3'

(SEQ ID NO: 14)
5'-TACCAGCGAGCAGGCCGAGT-3'

(SEQ ID NO: 15)
5'-TGCCCGATACACAAACGCTG-3'

(SEQ ID NO: 41)
5'- GUAUCUCUUGACGUUCCUUA-3'

(SEQ ID NO: 43)
5'-UGCCCGAUACACAAACGCUG-3'
```

In one embodiment of the present invention, the antisense oligonucleotide comprises at least 7 consecutive nucleotides of any one of the sequences set forth in SEQ ID NOs: 1, 2, 3, 13, 14 or 15. In another embodiment, the antisense oligonucleotide comprises at least 7 and no more than 19 consecutive nucleotides of the antisense oligonucleotide sequence set forth in SEQ ID NO:4.

In one embodiment of the present invention, the antisense oligonucleotides comprise a sequence that is complementary to a portion of the mRNA transcribed from the RAD51 gene. In one embodiment, the antisense oligonucleotides comprise a sequence that is complementary to a portion of the coding sequence of the RAD51 mRNA. In another embodiment, the antisense oligonucleotides comprise a sequence that is complementary to a portion of the 3'-UTR of the RAD51 mRNA. Examples of suitable target sequences within the RAD51 mRNA for the design of antisense oligonucleotides are known in the art and include those shown below.

```
                              [SEQ ID NO: 26]
5'-CUGCAUCUGCAUUGCCAUUA-3' (Sak et al. 2005, Br J

Cancer 92: 1089-1097)

[SEQ ID NO: 27]
5'-GGCUUCACUAAUUCC-3' (Raderschall et al. 2002, J

Cell Sci 115: 153-164)

[SEQ ID NO: 28]
5'-GUAAUGGCAAUGCAGAUGC-3' (Raderschall et al.

ibid.)
```

An additional example of a suitable antisense oligonucleotide targeted to RAD51 would be an antisense oligonucleotide targeted to all or a portion (for example, at least 7, 8, 9 or 10 consecutive nucleotides) of the following target sequence in the 3'-UTR:

```
                                      [SEQ ID NO: 29]
    1734 5'-GAAUGGGUCUGCACAGAUUC-3' 1753
```

An example of such an antisense oligonucleotide is:

```
                              [SEQ ID NO: 44]
        5'-GAATCTGTGCAGACCCATTC-3'
```

In one embodiment of the present invention, the antisense oligonucleotides comprise a sequence that is complementary to a portion of the mRNA transcribed from the DNA-PK gene. In one embodiment, the antisense oligonucleotides comprise a sequence that is complementary to a portion of the coding sequence of the DNA-PK mRNA. In another embodiment, the antisense oligonucleotides comprise a sequence that is complementary to a portion of the 3'-UTR of the DNA-PK mRNA. Examples of antisense oligonucleotide sequences that are targeted to sequences within the DNA-PK mRNA are provided below.

5'-GCAAGCCAGCTGAGGGCACA-3' [SEQ ID NO:31], which is targeted to part of the protein-coding region (positions 874 to 855) of the DNA-PK mRNA.

5'-GGGCATTCCAAGGCTTCCCCA-3' [SEQ ID NO:32], which is targeted to part of the 3'-UTR (positions 12719 to 12699) of the DNA-PK mRNA.

5'-GGGCTCCCATCCTTCCCAGG-3' [SEQ ID NO:33], which is targeted to part of the 3'-UTR (positions 12342 to 12323) of the DNA-PK mRNA.

5'-AGGGGCCTTCTCATGACCCAGG-3' [SEQ ID NO:34], which is targeted to part of the 3'-UTR (positions 12159 to 12180) of the DNA-PK mRNA.

5'-ACTGCTGGATTGGCACCTGCT-3' [SEQ ID NO:35], which is targeted to part of the 3'-UTR (positions 12117 to 12137) of the DNA-PK mRNA.

5'-TGGGGTCTGTTGCCTGGTCC-3' [SEQ ID NO:36], which is targeted to part of the 3'-UTR (positions 12307 to 12288) of the DNA-PK mRNA.

It is understood in the art that an antisense technologies including antisense oligonucleotide or siRNA need not have 100% identity with the complement of its target sequence. The antisense oligonucleotides in accordance with the present invention have a sequence that is at least about 75% identical to the complement of their target sequence. In one embodiment of the present invention, the antisense oligonucleotides have a sequence that is at least about 90% identical to the complement of the target sequence. In another embodiment, they have a sequence that is at least about 95% identical to the complement of target sequence, allowing for gaps or mismatches of several bases. In a further embodiment, they are at least about 98% identical to the complement of the target sequence. Identity can be determined, for example, by using the BLASTN program of the University of Wisconsin Computer Group (GCG) software or provided on the NCBI website.

In one embodiment, the antisense technologies including antisense oligonucleotides and siRNA are capable of decreasing or ablating the expression of the DNA DSB repair gene to which it is targeted. Methods of determining the ability of antisense technologies to decrease expression of a target gene are well-known in the art and may determine the decrease in expression at the nucleic acid level or the protein level or both. For example, after incubation of cells from an appropriate cell line with the antisense oligonucleotide or siRNA, the expression of the DNA DSB repair mRNA or protein can be determined using standard techniques known in the art. Numerous such techniques are available to the skilled worker, including DNA arrays, microarrays, protein arrays, proteomics, Northern blots, RT-PCR analysis, Western blot, and the like.

In the context of this invention, an oligonucleotide (OLIGO) can be an oligomer or polymer of ribonucleic acid (RNA), deoxyribonucleic acid (DNA), or modified RNA or DNA, or combinations thereof. This term, therefore, includes oligonucleotides composed of naturally-occurring nucleobases, sugars and covalent internucleoside (backbone) linkages as well as oligonucleotides having non-naturally-occurring portions, which function similarly. Such modified oligonucleotides are often preferred over native forms because of desirable properties such as, for example, enhanced cellular uptake, enhanced affinity for nucleic acid target and increased stability in the presence of nucleases. In one embodiment of the present invention, the antisense oligonucleotides comprise DNA and/or modified DNA. In another embodiment, the antisense oligonucleotides comprise RNA and/or modified RNA. In another embodiment, the antisense oligonucleotides comprise both DNA and RNA, and/or modified versions thereof.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific non-limiting examples of modified oligonucleotides useful in the present invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary antisense oligonucleotides or siRNA having modified oligonucleotide backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

In one embodiment of the present invention, the antisense oligonucleotide is a phosphorothioated oligonucleotide that comprises one or more phosphorothioate internucleotide linkages. In another embodiment, the antisense oligonucleotide comprises phosphorothioate internucleotide linkages that link the four, five or six 3'-terminal nucleotides of the oligonucleotide. In a further embodiment, the antisense oligonucleotide comprises phosphorothioate internucleotide linkages that link all the nucleotides of the oligonucleotide.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene-containing backbones; sulphamate backbones; methyleneimino and methylenehydrazino backbones; sulphonate and sulfonamide backbones; amide backbones; and others having mixed N, O, S and $CH_2$ component parts.

The present invention also contemplates modified oligonucleotides or siRNA in which both the sugar and the internucleoside linkage of the nucleotide units are replaced with novel groups. The base units are maintained for hybridization with an appropriate nucleic acid target compound. An example of such a modified oligonucleotide, which has been shown to have excellent hybridization properties, is a peptide nucleic acid (PNA) [Nielsen et al., Science, 254: 1497-1500 (1991)]. In PNA compounds, the sugar-backbone of an oligonucleotide is replaced with an amide-containing backbone, in particular an aminoethylglycine backbone. The nucleobases are retained and are bound directly or indirectly to aza-nitrogen atoms of the amide portion of the backbone.

The present invention also contemplates oligonucleotides or siRNA comprising "locked nucleic acids" (LNAs), which are conformationally restricted oligonucleotide analogues containing a methylene bridge that connects the 2'-O of ribose with the 4'-C (see, Singh et al., *Chem. Commun.*, 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., *Tetrahedron*, 1998, 54:3607-3630). Studies of mis-matched sequences show that LNA obey the Watson-Crick base pairing rules with generally improved selectivity compared to the corresponding unmodified reference strands.

Antisense oligonucleotides containing LNAs have been demonstrated to be efficacious and non-toxic (Wahlestedt et al., *Proc. Natl. Acad. Sci. U.S.A*, 2000, 97:5633-5638). In addition, the LNA/DNA copolymers were not degraded readily in blood serum and cell extracts.

LNAs form duplexes with complementary DNA or RNA or with complementary LNA, with high thermal affinities. The universality of LNA-mediated hybridization has been emphasized by the formation of exceedingly stable LNA:

LNA duplexes (Koshkin et al., *J. Am. Chem. Soc.,* 1998, 120:13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA (Singh et al., J. Org. Chem., 1998, 63, 10035-10039) and 2'-methylamino-LNA has been described and thermal stability of their duplexes with complementary RNA and DNA strands reported. Preparation of phosphorothioate-LNA and 2'-thio-LNA have also been described (Kumar et al., *Bioorg. Med. Chem. Lett.,* 1998, 8:2219-2222).

Modified oligonucleotides may also contain one or more substituted sugar moieties. For example, oligonucleotides may comprise sugars with one of the following substituents at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy (2'-O—$CH_2$$CH_2$ $OCH_3$, also known as 2'-O-(2-methoxyethyl) or 2'-MOE) [Martin et al., *Helv. Chim. Acta,* 78:486-504 (1995)], 2'-dimethylaminooxyethoxy ($O(CH_2)_2ON(CH_3)_2$ group, also known as 2'-DMAOE), 2'-methoxy (2'-O—$CH_3$), 2'-aminopropoxy (2'-$OCH_2CH_2CH_2NH_2$) and 2'-fluoro (2'-F).

In one embodiment of the present invention, the antisense oligonucleotide comprises at least one nucleotide comprising a substituted sugar moiety. In another embodiment, the antisense oligonucleotide comprises at least one 2'-O-(2-methoxyethyl) or 2'-MOE modified nucleotide. In another embodiment, the antisense oligonucleotide comprises at least one 2'-O-methyl or 2'-MOE ribonucleotide.

Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include modifications to the nucleobase. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., *Angewandte Chemie, Int. Ed.,* 30:613 (1991); and Sanghvi, Y. S., (1993) *Antisense Research and Applications,* pp 289-302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) *Antisense Research and Applications,* pp 276-278, Crooke, S. T. and Lebleu, B., ed., CRC Press, Boca Raton].

Another oligonucleotide modification included in the present invention is the chemical linkage to the oligonucleotide of one or more moieties or conjugates which enhance the activity, cellular distribution or cellular uptake of the oligonucleotide. Such moieties include, but are not limited to, lipid moieties such as a cholesterol moiety [Letsinger et al., *Proc. Natl. Acad. Sci. USA,* 86:6553-6556 (1989)], cholic acid [Manoharan et al., *Bioorg. Med. Chem. Let.,* 4:1053-1060 (1994)], a thioether, e.g. hexyl-S-tritylthiol [Manoharan et al., *Ann. N.Y. Acad. Sci.,* 660:306-309 (1992); Manoharan et al., *Bioorg. Med. Chem. Lett.,* 3:2765-2770 (1993)], a thiocholesterol [Oberhauser et al., *Nucl. Acids Res.,* 20:533-538 (1992)], an aliphatic chain, e.g. dodecandiol or undecyl residues [Saison-Behmoaras et al., *EMBO J.,* 10:1111-1118 (1991); Kabanov et al., *FEBS Lett.,* 259:327-330 (1990); Svinarchuk et al., *Biochimie,* 75:49-54 (1993)], a phospholipid, e.g. di-hexadecyl-rac-glycerol or triethylammonium 1,2-di-O-hexadecyl-rac-glycero-3-H-phosphonate [Manoharan et al., *Tetrahedron Lett.,* 36:3651-3654 (1995); Shea et al., *Nucl. Acids Res.,* 18:3777-3783 (1990)], a polyamine or a polyethylene glycol chain [Manoharan et al., *Nucleosides & Nucleotides,* 14:969-973 (1995)], or adamantane acetic acid [Manoharan et al., *Tetrahedron Lett.,* 36:3651-3654 (1995)], a palmityl moiety [Mishra et al., *Biochim. Biophys. Acta,* 1264:229-237 (1995)], or an octadecylamine or hexylamino-carbonyl-oxycholesterol moiety [Crooke et al., *J. Pharmacol. Exp. Ther.,* 277:923-937 (1996)].

One skilled in the art will recognise that it is not necessary for all positions in a given oligonucleotide to be uniformly modified. The present invention, therefore, contemplates the incorporation of more than one of the aforementioned modifications into a single oligonucleotide or even at a single nucleoside within the oligonucleotide.

In one embodiment of the present invention, the antisense oligonucleotides are gapmers. As used herein, the term "gapmer" refers to an antisense oligonucleotide comprising a central region (a "gap") and a region on either side of the central region (the "wings"), wherein the gap comprises at least one modification difference compared to each wing. Such modifications include nucleotide, internucleoside linkage, and sugar modifications as well as the absence of modification (unmodified RNA or DNA). Thus, in certain embodiments, the nucleotide linkages in each of the wings are different from the nucleotide linkages in the gap. In certain embodiments, each wing comprises modified nucleotides and the gap comprises nucleotides that do not comprise that modification. In certain embodiments the nucleotides in the gap and the nucleotides in the wings all comprise modified nucleotides, but the modifications in the gap are different from the modifications in each of the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) within each wing are the same. In certain embodiments, the modification(s) in one wing are different from the modification(s) in the other wing. In certain embodiments, the nucleotide linkages are the same in the gap and in the wings, but the wings comprise modified nucleotides whereas the gap does not. In one embodiment, the nucleotides in the wings comprise 2'-MOE modifications and the nucleotides in the gap do not.

In the context of the present invention, an antisense oligonucleotide or siRNA may be "nuclease resistant" when it has either been modified such that it is not susceptible to degradation by nucleases or alternatively has been placed in a delivery vehicle which in itself protects the oligonucleotide or siRNA from nucleases. Nuclease-resistant oligonucleotides include, for example, methyl phosphonates, phosphorothioates, phosphorodithioates, phosphotriesters, and morpholino oligomers. Suitable delivery vehicles for conferring nuclease resistance include, for example, liposomes. In one embodiment of the present invention, the antisense oligonucleotides are nuclease-resistant.

In some embodiments of the present invention, the antisense sequences may be provided in the context of RNAi constructs comprising sequences specific for proteins involved in the repair of double-stranded DNA breaks (DSBs), such as BRCA2, BRCA1, RAD51, PALB2 and DNA-PK.

In some embodiments, siRNA include chemical modifications at the 5' or 3'-terminus, backbone, sugar or nucleobase of siRNA. Appropriate modifications include the 2' position of the ribose ring, which has been proven to enhance siRNA stability by preventing degradation by endonucleases. Optionally the modifications include 2'-O-methyl and 2'-deoxy-2'-fluoro. Other modifications include replacement of the phosphodiester ($PO_4$) group with phosphothioate (PS) at the 3'-end of RNA backbone, or the combination of 4'-thiolation with 2'-O-alkyl modificatio In one embodiment of the present invention, the RNAi construct comprises a single-stranded polynucleotide that forms a hairpin structure which includes a double-stranded stem and a single-stranded loop, wherein the double-stranded stem can be cleaved by Dicer to produce an siRNA.

In one embodiment, the RNAi construct comprises a double-stranded (dsRNA) construct. The RNAi constructs may be modified to increase stability or increase cellular uptake.

The present invention further contemplates antisense oligonucleotides that contain groups for improving the pharmacokinetic properties of the oligonucleotide, or groups for improving the pharmacodynamic properties of the oligonucleotide.

In embodiments of the present invention where antisense oligonucleotides directed to nucleic acids encoding two or more target proteins are used, each oligonucleotide may be independently modified.

Preparation of the Antisense Oligonucleotides or siRNA

The antisense oligonucleotides or siRNAs in accordance with the present invention can be prepared by conventional techniques well-known to those skilled in the art. For example, the oligonucleotides can be prepared using solid-phase synthesis using commercially available equipment, such as the equipment available from Applied Biosystems Canada Inc., Mississauga, Canada. As is well-known in the art, modified oligonucleotides, such as phosphorothioates and alkylated derivatives, can also be readily prepared by similar methods.

Alternatively, the antisense oligonucleotides can be prepared by enzymatic digestion of the naturally occurring DNA DSB repair protein gene by methods known in the art.

Antisense oligonucleotides can also be prepared through the use of recombinant methods in which expression vectors comprising nucleic acid sequences that encode the antisense oligonucleotides are expressed in a suitable host cell. Such expression vectors can be readily constructed using procedures known in the art. Examples of suitable vectors include, but are not limited to, plasmids, phagemids, cosmids, bacteriophages, baculoviruses and retroviruses, and DNA viruses. One skilled in the art will understand that selection of the appropriate host cell for expression of the antisense oligonucleotide will be dependent upon the vector chosen. Examples of host cells include, but are not limited to, bacterial, yeast, insect, plant and mammalian cells.

One skilled in the art will also understand that the expression vector may further include one or more regulatory elements, such as transcriptional elements, required for efficient transcription of the antisense oligonucleotide sequences. Examples of regulatory elements that can be incorporated into the vector include, but are not limited to, promoters, enhancers, terminators, and polyadenylation signals. One skilled in the art will appreciate that selection of suitable regulatory elements is dependent on the host cell chosen for expression of the antisense oligonucleotide and that such regulatory elements may be derived from a variety of sources, including bacterial, fungal, viral, mammalian or insect genes.

The expression vectors can be introduced into a suitable host cell or tissue by one of a variety of methods known in the art. Such methods can be found generally described in Sambrook et al., 1992; Ausubel et al., 1989; Chang et al., 1995; Vega et al., 1995; and Vectors: A Survey of Molecular Cloning Vectors and Their Uses (1988) and include, for example, stable or transient transfection, lipofection, electroporation, and infection with recombinant viral vectors.

Efficacy of the Antisense Therapies

The antisense therapies in accordance with the present invention can be tested for their ability to inhibit the growth and/or proliferation of cancer cells in vitro and/or in vivo using standard techniques. The antisense oligonucleotides or siRNAs can be tested individually, or two or more antisense oligonucleotides or siRNA can be tested in combination. The antisense oligonucleotides or siRNA can also be tested in combination with other cancer therapies. Exemplary testing methods are described below and in the Examples provided herein.

1. In Vitro Testing

Initial determinations of the ability of the antisense oligonucleotides or siRNA to attenuate the growth or proliferation of neoplastic cells may be made using in vitro techniques if required.

For example, the cytotoxicity of the antisense oligonucleotides or siRNA can be assayed in vitro using a suitable cancer cell line. In general, cells of the selected test cell line are grown to an appropriate density and the test compound(s) are added. After an appropriate incubation time (for example, about 48 to 96 hours), cell survival is assessed. Methods of determining cell survival are well known in the art and include, but are not limited to, the resazurin reduction test (see Fields & Lancaster (1993) *Am. Biotechnol. Lab.* 11:48-50; O'Brien et al., (2000) *Eur. J. Biochem.* 267:5421-5426 and U.S. Pat. No. 5,501,959), the sulforhodamine assay (Rubinstein et al., (1990) *J. Natl. Cancer Inst.* 82:113-118) or the neutral red dye test (Kitano et al., (1991) *Euro. J. Clin. Investg.* 21:53-58; West et al., (1992) *J. Investigative Derm.* 99:95-100). Cytotoxicity is determined by comparison of cell survival in the treated culture with cell survival in one or more control cultures, for example, untreated cultures, cultures pre-treated with a control compound (typically a known therapeutic) and/or cultures treated individually with the components of the antisense oligonucleotide.

Alternatively, the ability of the antisense oligonucleotides or siRNA to inhibit proliferation of neoplastic cells can be assessed by culturing cells of a cancer cell line of interest in a suitable medium. After an appropriate incubation time, the cells can be treated with the antisense oligonucleotide or siRNA and incubated for a further period of time. Cells are then counted using a technique known in the art, such as an electronic particle counter or a haemocytometer, and compared to an appropriate control, as described above.

The antisense oligonucleotides or siRNAs can also be tested in vitro by determining their ability to inhibit anchorage-independent growth of tumour cells. Anchorage-independent growth is known in the art to be a good indicator of tumourigenicity. In general, anchorage-independent growth is assessed by plating cells from an appropriate cancer cell line onto soft agar and determining the number of colonies formed after an appropriate incubation period. Growth of cells treated with the antisense oligonucleotides or siRNAs can then be compared with that of cells treated with an appropriate control (as described above) and with that of untreated cells.

A variety of cancer cell lines suitable for testing the antisense oligonucleotides or siRNAs are known in the art and many are commercially available (for example, from the American Type Culture Collection, Manassas, Va.). In one embodiment of the present invention, in vitro testing of the antisense oligonucleotides or siRNAs is conducted in a human cancer cell line. Examples of suitable cancer cell lines for in vitro testing include, but are not limited to, breast cancer cell lines MDA-MB-231 and MCF-7, renal carcinoma cell line A-498, mesothelial cell lines MSTO-211H, NCI-H2052 and NCI-H28, ovarian cancer cell lines OV90 and SK-OV-3, colon cancer cell lines CaCo, HCT116 and HT29, cervical cancer cell line HeLa, non-small cell lung carcinoma cell lines A549, A549b, and H1299, pancreatic cancer cell lines MIA-PaCa-2 and AsPC-1, prostatic cancer-cell line PC-3, bladder cancer cell line T24, liver cancer cell line HepG2, brain cancer cell line U-87 MG, melanoma cell line A2058, and lung cancer cell line NCI-H460. Other examples of suitable cell lines are known in the art.

If necessary, the toxicity of the antisense oligonucleotides or siRNAs can also be initially assessed in vitro using standard techniques. For example, human primary fibroblasts can be treated in vitro with the oligonucleotide or siRNAs in the presence of a commercial lipid carrier such as Lipofectamine 2000 (LFA2K) (available from Life Technologies, Burlington, Ontario, Canada). Cells are then tested at different time points following treatment for their viability using a standard viability assay, such as the trypan-blue exclusion assay. Cells are also assayed for their ability to synthesize DNA, for example, using a thymidine incorporation assay, and for changes in cell cycle dynamics, for example, using a standard fluorescence-dependent flow cytometric assay.

2. In Vivo Testing

The ability of the antisense oligonucleotides or siRNAs to inhibit tumour growth or proliferation in vivo can be determined in an appropriate animal model using standard techniques known in the art (see, for example, Enna, et al., *Current Protocols in Pharmacology*, J. Wiley & Sons, Inc., New York, N.Y.).

In general, current animal models for screening anti-tumour compounds are xenograft models, in which a human or mammalian tumour has been implanted into an animal. Examples of xenograft models of human cancer include, but are not limited to, human solid tumour xenografts in mice, implanted by sub-cutaneous injection and used in tumour growth assays; human solid tumour isografts in mice, implanted by fat pad injection and used in tumour growth assays; human solid tumour orthotopic xenografts, implanted directly into the relevant tissue and used in tumour growth assays; experimental models of lymphoma and leukaemia in mice, used in survival assays, and experimental models of metastasis in mice.

For example, the antisense oligonucleotides or siRNA can be tested in vivo on solid tumours using mice that are subcutaneously grafted bilaterally with a pre-determined amount of a tumour fragment on day 0. The animals bearing tumours are mixed before being subjected to the various treatments and controls. In the case of treatment of advanced tumours, tumours are allowed to develop to the desired size, animals having insufficiently developed tumours being eliminated. The selected animals are distributed at random into groups that will undergo the treatments or act as controls. Animals not bearing tumours may also be subjected to the same treatments as the tumour-bearing animals in order to be able to dissociate the toxic effect from the specific effect on the tumour. Treatment generally begins from 3 to 22 days after grafting, depending on the type of tumour, and the animals are observed every day. The antisense oligonucleotides of the present invention can be administered to the animals, for example, by bolus infusion or intraperitoneal injection (Ferguson et al., 2007, *Eur J Cancer Supplements*, Abstract B153, p. 211-212). The different animal groups are weighed about 3 or 4 times a week until the maximum weight loss is attained, after which the groups are weighed less frequently, for example, at least once a week until the end of the trial.

The tumours are measured about 2 or 3 times a week until the tumour reaches a pre-determined size and/or weight, or until the animal dies if this occurs before the tumour reaches the pre-determined size/weight. The animals are then sacrificed and the tissue histology, size and/or proliferation of the tumour assessed.

For the study of the effect of the compositions on leukaemias, the animals are grafted with a particular number of cells, and the anti-tumour activity is determined by the increase in the survival time of the treated mice relative to the controls.

To study the effect of the antisense oligonucleotides or siRNAs of the present invention on tumour metastasis, tumour cells are typically treated with the composition ex vivo and then injected into a suitable test animal. The spread of the tumour cells from the site of injection is then monitored over a suitable period of time by standard techniques. In another technique, test animals in which a primary tumour has been established can be used. The primary tumour is removed when it reaches a certain size and/or after it has been treated with a certain protocol, and the appearance of metastases is monitored. Alternatively, after removal of the primary tumour, the animal can be treated to determine whether growth of metastases can be inhibited in comparison to no-treatment control animals.

In vivo toxic effects of the oligonucleotides can be evaluated by measuring their effect on animal body weight during treatment and by performing haematological profiles and liver enzyme analysis after the animal has been sacrificed.

TABLE 2

Examples of Xenograft Models of Human Cancer

| Cancer Model | Cell Type |
|---|---|
| Tumour Growth Assay Human solid tumour xenografts in mice (sub-cutaneous injection) | Prostate (PC-3, DU145) Breast (MDA-MB-231, MVB-9) Colon (HT-29) Lung (NCI-H460, NCI-H209, A549) Pancreatic (ASPC-1, SU86.86) Pancreatic: drug resistant (BxPC-3) Skin (A2058, C8161) Cervical (SIHA, HeLa-S3) Cervical: drug resistant (HeLa S3-HU-resistance) Liver (HepG2) Brain (U87-MG) Renal (Caki-1, A498) Ovary (SK-OV-3) |
| Tumour Growth Assay Human solid tumour isografts in mice (fat pad injection) | Breast: drug resistant (MDA-CDDP-S4, MDA-MB435-To.1) |
| Survival Assay | Human: Burkitts lymphoma (Non-Hodgkin's) (Raji) |
| Experimental model of lymphoma and leukaemia in mice | Murine: erythroleukemia (CB7 Friend retrovirus-induced), L1210, P388, S49 |
| Experimental model of lung metastasis in mice | Human: melanoma (C8161) Murine: fibrosarcoma (R3) |

3. Combination Therapies

As noted above, the antisense oligonucleotides or siRNA can be tested in combination with another cancer therapy. Combinations comprising two or more antisense oligonucleotides or siRNAs, or comprising the antisense oligonucleotide or siRNA(s) together with another cancer therapy may be more effective than each of the components when used alone. Improved efficacy can be manifested, for example, as a less-than-additive effect, wherein the effect of the combination is greater than the effect of each component alone, but less than the sum of the effects of the components, or it may be an additive effect, wherein the effect of the combination is equivalent to the sum of the effects of the components when used individually, or it may be a greater-than-additive effect, wherein the effect of the combination is greater than the sum of the effects of each component used alone. Greater-than-additive effects may also be described as synergistic. The improved efficacy of the combinations can be determined by a number of methods known in the art.

For example, such improved efficacy can result in one or more of: (i) an increase in the ability of the combination to inhibit the growth or proliferation of neoplastic cells when compared to the effect of each component alone; (ii) a decrease in the dose of one or more of the components being required to bring about a certain effect (i.e. a decrease in the median effective dose or $ED_{50}$); (iii) decreased toxicity phenomena associated with one or more of the components (i.e. an increase in the median lethal dose or $LD_{50}$), and (iv) an improved therapeutic index or clinical therapeutic index of the combination when compared to the therapeutic index/clinical therapeutic index of each component alone.

As used herein, the term "therapeutic index" is defined as $LD_{50}/ED_{50}$, where "$ED_{50}$" is the amount of a compound that produces 50% of the maximum response or effect associated with the compound, or the amount that produces a predetermined response or effect in 50% of a test population, and "$LD_{50}$" is the amount of a compound that has a lethal effect in 50% of a test population. Thus, a compound with a high therapeutic index can typically be administered with greater safety than one with a low therapeutic index. The $LD_{50}$ is determined in preclinical trials, whereas the $ED_{50}$ can be determined in preclinical or clinical trials. Preclinical trials are conducted using an appropriate animal model, such as those described herein. The therapeutic index can also be determined based on doses that produce a therapeutic effect and doses that produce a toxic effect (for example, the $ED_{90}$ and $LD_{10}$, respectively).

"Clinical therapeutic index" differs from therapeutic index in that some indices of relative safety or relative effectiveness in patients in a clinical setting cannot be defined explicitly and uniquely. A combination is considered to demonstrate an improved Clinical Therapeutic Index, therefore, when it meets one of the following criteria as defined by the Food and Drug Administration: demonstrates increased safety (or patient acceptance) at an accepted level of efficacy within the recommended dosage range, or demonstrates increased efficacy at equivalent levels of safety (or patient acceptance) within the recommended dosage range, as compared to each of the components in the combination. Alternatively, during clinical studies, the dose or the concentration (for example, in solution, blood, serum, plasma) of a drug required to produce toxic effects can be compared to the concentration required to achieve the desired therapeutic effects in the population in order to evaluate the clinical therapeutic index. Methods of clinical studies to evaluate the clinical therapeutic index are well known to workers skilled in the art.

Combinations may also exhibit therapeutic synergy, wherein "therapeutic synergy" is demonstrated when a combination is therapeutically superior to one of the components of the combination when used at that component's optimum dose [as defined in T. H. Corbett et al., (1982) *Cancer Treatment Reports,* 66:1187]. To demonstrate the efficacy of a combination, it may be necessary to compare the maximum tolerated dose of the combination with the maximum tolerated dose of each of the separate components in the study in question. This efficacy may be quantified using techniques and equations commonly known to workers skilled in the art [see, for example, T. H. Corbett et al., (1977) *Cancer,* 40, 2660.2680; F. M. Schabel et al., (1979) *Cancer* Drug Development, Part B, *Methods in Cancer Research,* 17:3-51, New York, Academic Press Inc.].

One embodiment of the present invention provides for the use of a combination of two or more antisense oligonucleotides or siRNAs targeted to a nucleic acid encoding a DNA DSB repair protein, wherein the effect of the combination is greater-than-additive or synergistic. Another embodiment of the present invention provides for the use of a combination of an antisense oligonucleotide or siRNA targeted to a nucleic acid encoding a DNA DSB repair protein and a cancer therapy that damages DNA, inhibits a DNA repair pathway or impacts DNA synthesis, wherein the effect of the combination is greater-than-additive or synergistic. Another embodiment provides for the use of a combination of one or more antisense oligonucleotides or siRNA targeted to a specific DNA DSB repair protein mRNA with another cancer therapy, such as radiation or a chemotherapeutic drug, wherein the effect of the combination is greater-than-additive or synergistic.

Pharmaceutical Compositions

The antisense oligonucleotide(s) or siRNAs may be administered as a pharmaceutical composition in which the antisense oligonucleotide(s) or siRNA are admixed with an appropriate pharmaceutically acceptable carrier, diluent, excipient, vehicle or carriers.

The siRNAs may be in the form of dynamic polyconjugates, LODER polymer, lipid nanoparticles or nanoparticles including cyclodextrin. Other appropriate delivery systems include polymers, lipids, peptides, antibodies, aptamers, receptors and small molecules.

The pharmaceutical compositions of the present invention may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The present invention also provides for pharmaceutical compositions comprising an antisense oligonucleotide or siRNA associated with a liposomal-type vehicle, such as an artificial membrane vesicle (including a liposome, lipid micelle and the like), microparticle or microcapsule.

The pharmaceutical compositions may be in a form suitable for oral use, for example, as tablets, troches, lozenges, aqueous or oily suspensions, dispersible powders or granules, emulsion hard or soft capsules, or syrups or elixirs. Compositions intended for oral use may be prepared according to methods known to the art for the manufacture of pharmaceutical compositions and may contain one or more agents selected from the group of sweetening agents, flavouring agents, colouring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatine or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monosterate or glyceryl distearate may be employed.

Pharmaceutical compositions for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium such as peanut oil, liquid paraffin or olive oil.

Aqueous suspensions contain the active compound in admixture with suitable excipients including, for example, suspending agents, such as sodium carboxymethylcellulose, methyl cellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxybenzoate, one or more colouring agents, one or more flavouring agents or one or more sweetening agents, such as sucrose or saccharin.

Oily suspensions may be formulated by suspending the active ingredients in a vegetable oil, for example, *arachis* oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavouring agents may be added to provide palatable oral preparations. These compositions can be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example, olive oil or *arachis* oil, or a mineral oil, for example, liquid paraffin, or it may be a mixture of these oils. Suitable emulsifying agents may be naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative, and/or flavouring and colouring agents.

The pharmaceutical compositions may be in the form of a sterile injectable aqueous or oleaginous suspension. This suspension may be formulated according to known art using suitable dispersing or wetting agents and suspending agents such as those mentioned above. The sterile injectable preparation may also be sterile injectable solution or suspension in a non-toxic parentally acceptable diluent or solvent, for example, as a solution in 1,3-butanediol. Acceptable vehicles and solvents that may be employed include, but are not limited to, water, Ringer's solution, lactated Ringer's solution and isotonic sodium chloride solution. Other examples are, sterile, fixed oils which are conventionally employed as a solvent or suspending medium, and a variety of bland fixed oils including, for example, synthetic mono- or diglycerides. In addition, fatty acids such as oleic acid find use in the preparation of injectables.

In one embodiment of the present invention, the pharmaceutical composition comprising the antisense oligonucleotide or siRNA is formulated for injection or infusion.

Other pharmaceutical compositions and methods of preparing pharmaceutical compositions are known in the art and are described, for example, in "*Remington: The Science and Practice of Pharmacy*," Gennaro, A., Lippincott, Williams & Wilkins, Philadelphia, Pa. (2000) (formerly "*Remingtons Pharmaceutical Sciences*").

Use of the Antisense Based Therapies

The present invention provides for the use of the antisense based therapies including antisense oligonucleotides or siRNAs in the treatment of cancer. The antisense oligonucleotides or siRNA may be used alone as single agents or may be used in combination with another cancer therapy. When used as a single agent, the antisense oligonucleotides or siRNA may be used singly or in tandem (i.e. two antisense oligonucleotides or siRNAs targeting the same DNA DSB repair protein gene or mRNA), or the antisense oligonucleotides or siRNA may be combined in various other ways (for example, three or more antisense oligonucleotides and/or siRNAs targeting the same DNA DSB repair protein gene or mRNA, or two or more two antisense oligonucleotides and/or siRNAs each targeting a different DNA DSB repair protein gene or mRNA).

One embodiment of the present invention provides for the use of one or more antisense oligonucleotides or siRNAs targeting a specific DNA DSB repair protein mRNA in the treatment of cancer. Another embodiment provides for the use of a combination of one or more antisense oligonucleotides or siRNAs targeting a specific DNA DSB repair protein mRNA and one or more antisense oligonucleotides or siRNAs targeting a different specific DNA DSB repair protein mRNA in order to treat cancer. Another embodiment provides for the use of a combination of one or more antisense oligonucleotides or siRNAs targeting a specific DNA DSB repair protein mRNA with another cancer therapy, such as radiation or a chemotherapeutic drug.

One embodiment of the invention provides for the use of a combination of one or more antisense oligonucleotides or siRNAs targeted to the mRNA of a DNA DSB repair protein mRNA in the HR-DD pathway with one or more antisense oligonucleotides targeted to the mRNA of a DNA DSB repair protein mRNA in the NHEJ pathway. The use in accordance with this embodiment includes the use of the antisense oligonucleotides or siRNAs alone or in conjunction with one or more other cancer therapies, such as radiation or a chemotherapeutic drug.

The present invention contemplates the use of the antisense oligonucleotides or siRNAs in the treatment of a variety of cancers. Treatment of cancer encompasses the use of the antisense oligonucleotides or siRNAs to treat, stabilize or prevent cancer. In this context, treatment with the antisense oligonucleotides or siRNAs may result in, for example, a reduction in the size of a tumour, the slowing or prevention of an increase in the size of a tumour, an increase in the disease-free survival time between the disappearance or removal of a tumour and its reappearance, prevention of an initial or subsequent occurrence of a tumour (e.g. metastasis), an increase in the time to progression, reduction of one or more adverse symptom associated with a tumour, a slowing of tumour regression, or an increase in the overall survival time of a subject having cancer.

Examples of cancers which may be may be treated or stabilized in accordance with the present invention include, but are not limited to haematologic neoplasms, including leukaemias and lymphomas; carcinomas, including adenocarcinomas; melanomas and sarcomas. Carcinomas, adenocarcinomas and sarcomas are also frequently referred to as "solid tumours." Examples of commonly occurring solid tumours include, but are not limited to, cancer of the brain, breast, cervix, colon, rectum, head and neck, kidney, lung including both small cell and non-small cell lung cancer, ovary, pancreas, prostate, stomach and uterus. Various forms of lymphoma also may result in the formation of a solid tumour and, therefore, in certain contexts may also be considered to be solid tumours.

The term "leukaemia" refers broadly to progressive, malignant diseases of the blood-forming organs. Leukaemia is typically characterized by a distorted proliferation and development of leukocytes and their precursors in the blood and bone marrow but can also refer to malignant diseases of other blood cells such as erythroleukaemia, which affects immature red blood cells. Leukaemia is generally clinically classified on the basis of (1) the duration and character of the disease—acute or chronic; (2) the type of cell involved—myeloid (myelogenous), lymphoid (lymphogenous) or monocytic, and (3) the increase or non-increase in the number of abnormal cells in the blood—leukaemic or aleukaemic (subleukaemic). Leukaemia includes, for example, acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, aleukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "lymphoma" generally refers to a malignant neoplasm of the lymphatic system, including cancer of the lymphatic system. The two main types of lymphoma are Hodgkin's disease (HD or HL) and non-Hodgkin's lymphoma (NHL). Abnormal cells appear as congregations which enlarge the lymph nodes, form solid tumours in the body, or more rarely, like leukemia, circulate in the blood. Hodgkins' disease lymphomas include: nodular lymphocyte predominance Hodgkin's lymphoma; classical Hodgkin's lymphoma; nodular sclerosis Hodgkin's lymphoma; lymphocyte-rich classical Hodgkin's lymphoma; mixed cellularity Hodgkin's lymphoma; lymphocyte depletion Hodgkin's lymphoma. Non-Hodgkin's lymphomas include small lymphocytic NHL; follicular NHL; mantle cell NHL; mucosa-associated lymphoid tissue (MALT) NHL; diffuse large cell B-cell NHL; mediastinal large B-cell NHL; precursor T lymphoblastic NHL; cutaneous T-cell NHL; T-cell and natural killer cell NHL; mature (peripheral) T-cell NHL; Burkitt's lymphoma; mycosis fungoides; Sézary Syndrome; precursor B-lymphoblastic lymphoma; B-cell small lymphocytic lymphoma; lymphoplasmacytic lymphoma; splenic marginal zone B-cell lymphoma; nodal marginal zone lymphoma; plasma cell myeloma/plasmacytoma; intravascular large B-cell NHL; primary effusion lymphoma; blastic natural killer cell lymphoma; enteropathy-type T-cell lymphoma; hepatosplenic gamma-delta T-cell lymphoma; subcutaneous panniculitis-like T-cell lymphoma; angioimmunoblastic T-cell lymphoma; and primary systemic anaplastic large T/null cell lymphoma.

The term "sarcoma" generally refers to a tumour which originates in connective tissue, such as muscle, bone, cartilage or fat, and is made up of a substance like embryonic connective tissue and is generally composed of closely packed cells embedded in a fibrillar or homogeneous substance. Sarcomas include soft tissue sarcomas, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, choriocarcinoma, embryonal sarcoma, Wilms tumour sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented haemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumour arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, sublingual melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colorectal carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epidermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, haematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, lipomatous carcinoma, lymphoepithelial carcinoma, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, non-small cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous cell carcinoma, string carcinoma, carcinoma telangiectaticum, carcinoma telangiectodes, transitional cell carcinoma, carcinoma *tuberosum*, tuberous carcinoma, verrucous carcinoma, and carcinoma *villosum*.

The term "carcinoma" also encompasses adenocarcinomas. Adenocarcinomas are carcinomas that originate in cells that make organs which have glandular (secretory) properties or that originate in cells that line hollow viscera, such as the gastrointestinal tract or bronchial epithelia. Examples include, but are not limited to, adenocarcinomas of the breast, lung, pancreas and prostate.

Additional cancers encompassed by the present invention include, for example, multiple myeloma, neuroblastoma, rhabdomyosarcoma, primary thrombocytosis, primary macroglobulinemia, small-cell lung tumours, primary brain tumours, malignant pancreatic insulinoma, malignant carcinoid, urinary bladder cancer, premalignant skin lesions, gliomas, testicular cancer, thyroid cancer, esophageal cancer, genitourinary tract cancer, malignant hypercalcemia, endometrial cancer, adrenal cortical cancer, mesothelioma and medulloblastoma.

In one embodiment, the antisense oligonucleotides are used in the treatment of a solid tumour. In another embodiment, the antisense oligonucleotides are used to treat lung cancer, breast cancer, ovarian cancer, head and neck cancer or prostate cancer. In another embodiment, the antisense oligonucleotides or siRNAs are used to treat non-small cell lung cancer, breast cancer, ovarian cancer, head and neck cancer or prostate cancer. In another embodiment, the antisense oligonucleotides are used to treat breast cancer, ovarian cancer, prostate cancer, or non-small cell lung cancer. In another embodiment, the antisense oligonucleotides are used to treat colorectal cancer.

In accordance with one embodiment of the present invention, the antisense oligonucleotides or siRNA are used to inhibit expression of one or more DNA repair pathway protein(s) in a patient thereby allowing the patient to obtain greater benefit from treatment with a DNA damaging agent and/or an inhibitor of DNA repair or synthesis.

In accordance with one embodiment of the present invention, one or more antisense oligonucleotides are used in combination with one or more siRNAs. Optionally, the antisense oligonucleotides have the same target mRNA as the siRNAs. Alternatively, the target is a different mRNA.

In accordance with one embodiment of the present invention, the antisense oligonucleotides or siRNAs are used to inhibit expression of two or more DNA repair pathway protein(s) in a patient thereby mimicking a "synthetic lethal" situation.

In another embodiment, the antisense oligonucleotides or siRNA are used in a patient that already has a known defect in a DNA repair pathway in order to inhibit expression of a compensatory DNA repair protein thereby mimicking or creating a "synthetic lethal" situation.

In another embodiment, the antisense oligonucleotides or siRNA are used in a patient who had a reversion of a defect in a DNA repair pathway in order to restore sensitivity to DNA damaging chemotherapeutics.

In another embodiment, the antisense oligonucleotides or siRNA are used to inhibit a DNA repair pathway and thereby lower the efficiency of ds-DNA repair.

As noted above, the methods provided by the present invention are broadly applicable to cancer and are not limited to the treatment of cancers having a defect in a DNA repair mechanism. In one embodiment, however, the invention provides for the use of the antisense oligonucleotides or siRNAs in the treatment of cancers with one or more defective DNA repair mechanisms, for example, the antisense oligonucleotides or siRNAs can be used in the treatment of cancers with a defective base excision repair mechanism, with a defective nucleotide excision repair mechanism or with a defective mismatch repair mechanism. In another embodiment, the invention provides for the use of the antisense oligonucleotides or siRNAs in the treatment of cancers with one or more defective DNA repair mechanisms wherein the defect is either not well defined or understood.

The antisense oligonucleotides or siRNAs are administered to a subject in an amount effective to achieve the intended purpose. The exact dosage to be administered can be readily determined by the medical practitioner, in light of factors related to the patient requiring treatment. Factors which may be taken into account when determining an appropriate dosage include the severity of the disease state, general health of the subject, age, weight, and gender of the subject, diet, time and frequency of administration, the particular components of the combination, reaction sensitivities, and tolerance/response to therapy.

Antisense oligonucleotides or siRNAs are typically administered parenterally, for example, by intravenous infusion. Other methods of administering antisense oligonucleotides or siRNAs are known in the art.

Combination Therapies

In one embodiment, the present invention provides for the use of the antisense oligonucleotides in the treatment of cancer in combination with other cancer therapies, such as radiation therapy or chemotherapy. One embodiment of the present invention provides for the use of the antisense oligonucleotides or siRNAs in combination with a cancer therapy that damages DNA and/or inhibits DNA repair or synthesis. Suitable cancer therapies include established cancer therapies, as well as novel agents that are in clinical trials.

Such combinations may be more effective than either therapy when used alone. Another embodiment of the invention, therefore, provides for the use of the antisense oligonucleotides or siRNAs in combination with a cancer therapy that damages DNA and/or inhibits DNA repair or synthesis, wherein the effect of the combination is more than additive or synergistic.

One embodiment of the invention provides for the use of one or more of the antisense oligonucleotides or siRNAs together with a cancer therapy that damages DNA and/or inhibits DNA repair or synthesis, wherein the cancer therapy is a platinum drug, inhibitor of PARP, alkylating agent, radiation therapy, or inhibitor of thymidylate synthase. The present invention also contemplates the use of the antisense oligonucleotides with other potential DNA-damaging agents, including, but not limited to, inhibitors of topoisomerases, polymerases, telomerases, helicases, aurora kinase, DNA-dependent kinases, cyclin-dependent kinases, and ligases.

In one embodiment, the antisense oligonucleotides or siRNAs are used in the treatment of cancer in combination with one or more platinum drugs. Non-limiting examples of suitable platinum drugs include cisplatin, carboplatin, oxaliplatin, nedaplatin, satraplatin, triplatin, picoplatin and tetranitrate.

In one embodiment, the antisense oligonucleotides or siRNAs are used in the treatment of cancer in combination with one or more PARP inhibitors. Suitable non-limiting examples of PARP inhibitors include olaparib (AstraZeneca, (4-[(3-{[4-cyclopropylcarbonyl)piperazin-1-yl]carbonyl}-4-fluorophenyl)methyl]phthalazin-1(2H)-one; also known as AZD2281)) or BSI-201 (BiPAR-Sanofi). Other suitable examples of PARP inhibitors include those described in U.S. Patent Publication Nos. 2005/0227919 or 2009/0098084.

In one embodiment, the antisense oligonucleotides or siRNAs are used in the treatment of cancer in combination with one or more alkylating agents. Suitable alkylating agents include, for example, melphalan, cyclophosphamide, mechlorethamine or mustine (HN2), uramustine or uracil mustard, chlorambucil, ifosfamide, carmustine, lomustine, streptozocin, busulfan, and temozolamide.

In one embodiment, the antisense oligonucleotides or siRNAs are used in the treatment of cancer in combination with radiation therapy. Suitable examples of radiation therapy include external beam radiotherapy (EBRT or XRT) or teletherapy, brachytherapy or sealed source radiotherapy, or systemic radioisotope therapy or unsealed source radiotherapy.

In one embodiment, the antisense oligonucleotides or siRNAs are used in the treatment of cancer in combination with one or more inhibitors of thymidylate synthase (TS). Suitable inhibitors include, but are not limited to, the fluoropyrimidine drugs 5-FU, 5-FUdR, capecitabine (an oral form of a pro-drug of 5-FU) and a topical 5-FU cream (Effudex®), as well as the non-fluoropyrimidine drugs raltitrexed, methotrexate, pemetrexed (Alimta®) and antisense oligonucleotides targeted to the TS gene or mRNA. In a specific embodiment, the antisense oligonucleotides or siRNAs are used in the treatment of cancer in combination with an antisense oligonucleotide targeted to the TS gene or mRNA. Suitable anti-TS oligonucleotides include those described in U.S. Patent Application Publication No. 2008/0255066. In one embodiment, the antisense oligonucleotides are used in the treatment of cancer in combination with an antisense oligonucleotides targeted to the TS mRNA, wherein the anti-TS antisense oligonucleotide comprises the sequence:

5'-GCCAGTGGCAACATCCTTAA-3' (SEQ ID NO: 16)

In one embodiment, an anti-TS antisense and an anti-BRCA2 antisense or siRNA are used in combination with a platinum-based chemotherapeutic and an inhibitor of thymidylate synthase including a fluoropyrimidine such as 5FU. In specific embodiments, the thymidylate synthase inhibitor is pemetrexed.

In specific embodiments, the anti-BRCA2 antisense is BR1 antisense. In other specific embodiments, the anti-BRCA2 antisense is BR2 antisense or BR3 antisense.

In specific embodiments, the anti-BRCA2 siRNA is one or more of the siRNAs shown in Table 1.

Clinical Trials in Cancer Patients

One skilled in the art will appreciate that, following the demonstrated effectiveness of the antisense oligonucleotides or siRNA in vitro and in animal models, they should be tested in Clinical Trials in order to further evaluate their efficacy in the treatment of cancer and to obtain regulatory approval for therapeutic use. As is known in the art, clinical trials progress through phases of testing, which are identified as Phases I, II, III, and IV. Representative examples of Phase I/II Clinical Trials are provided in the Examples herein.

Initially the antisense oligonucleotides or siRNAs will be evaluated in a Phase I trial. Typically Phase I trials are used to determine the best mode of administration (for example, by pill or by injection), the frequency of administration, and the toxicity for the compounds. Phase I studies frequently include laboratory tests, such as blood tests and biopsies, to evaluate the effects of a compound in the body of the patient. For a Phase I trial, a small group of cancer patients is treated with a specific dose of the antisense oligonucleotide or siRNA. During the trial, the dose is typically increased group by group in order to determine the maximum tolerated dose (MTD) and the dose-limiting toxicities (DLT) associated with the antisense oligonucleotide. This process determines an appropriate dose to use in a subsequent Phase II trial.

A Phase II trial can be conducted to evaluate further the effectiveness and safety of the antisense oligonucleotides. In Phase II trials, the antisense oligonucleotide is administered to groups of patients with either one specific type of cancer or with related cancers, using the maximum dosage found to be safe and effective in Phase I trials.

Phase III trials focus on determining how a compound compares to the standard, or most widely accepted, treatment. In Phase III trials, patients are randomly assigned to one of two or more "arms". In a trial with two arms, for example, one arm will receive the standard treatment (control group) and the other arm will receive treatment with the antisense oligonucleotide (investigational group).

Phase IV trials are used to further evaluate the long-term safety and effectiveness of an antisense oligonucleotide or siRNA. Phase IV trials are less common than Phase I, II and III trials and will take place after the antisense oligonucleotide or siRNA has been approved for standard use.

Eligibility of Patients for Clinical Trials

Participant eligibility criteria can range from general (for example, age, sex, type of cancer) to specific (for example, type and number of prior treatments, tumour characteristics, blood cell counts, organ function). Eligibility criteria may also vary with trial phase. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I cancer trials usually comprise 15 to 30 participants for whom other treatment options have not been effective. Phase II trials typically comprise up to 100 participants who have already received chemotherapy, surgery, or radiation treatment, but for whom the treatment has not been effective. Participation in Phase II trials is often restricted based on the previous treatment received. For trials that are investigating the use of the antisense oligonucleotides of the invention as a first line therapy, for example, the patients selected for participation should not have undergone any prior systemic therapy. Phase III trials usually comprise hundreds to thousands of participants. This large number of participants is necessary in order to determine whether there are true differences between the effectiveness of the antisense oligonucleotide of the present invention and the standard treatment. Phase III may comprise patients ranging from those newly diagnosed with cancer to those with extensive disease in order to cover the disease continuum.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

Assessment of Patients Prior to Treatment

Prior to commencement of the study, several measures known in the art can be used to first classify the patients. Patients can first be assessed, for example, using the Eastern Cooperative Oncology Group (ECOG) Performance Status (PS) scale. ECOG PS is a widely accepted standard for the assessment of the progression of a patient's disease as measured by functional impairment in the patient, with ECOG PS 0 indicating no functional impairment, ECOG PS 1 and 2 indicating that the patients have progressively greater functional impairment but are still ambulatory and ECOG PS 3 and 4 indicating progressive disablement and lack of mobility.

Patients' overall quality of life can be assessed, for example, using the McGill Quality of Life Questionnaire (MQOL) (Cohen et al (1995) *Palliative Medicine* 9: 207-219). The MQOL measures physical symptoms; physical, psychological and existential well-being; support; and overall quality of life. To assess symptoms such as nausea, mood, appetite, insomnia, mobility and fatigue the Symptom Distress Scale (SDS) developed by McCorkle and Young ((1978) *Cancer Nursing* 1: 373-378) can be used.

Patients can also be classified according to the type and/or stage of their disease and/or by tumour size.

Administration of the Antisense Oligonucleotides or siRNA in Clinical Trials

The antisense oligonucleotide or siRNA is typically administered to the trial participants parenterally. In one embodiment, the antisense oligonucleotide or siRNA is administered by intravenous infusion. Methods of administering drugs by intravenous infusion are known in the art. Usually intravenous infusion takes place over a certain time period, for example, over the course of 60 minutes.

Monitoring of Patient Outcome

The endpoint of a clinical trial is a measurable outcome that indicates the effectiveness of a treatment under evaluation. The endpoint is established prior to the commencement of the trial and will vary depending on the type and phase of the clinical trial. Examples of endpoints include, for example, tumour response rate—the proportion of trial participants whose tumour was reduced in size by a specific amount, usually described as a percentage; disease-free survival—the amount of time a participant survives without cancer occurring or recurring, usually measured in months; overall survival—the amount of time a participant lives, typically measured from the beginning of the clinical trial until the time of death. For advanced and/or metastatic cancers, disease stabilization—the proportion of trial participants whose disease has stabilised, for example, whose tumour(s) has ceased to grow and/or metastasize ("progress"), can be used as an endpoint. Other endpoints include toxicity and quality of life.

Tumour response rate is a typical endpoint in Phase II trials. However, even if a treatment reduces the size of a participant's tumour and lengthens the period of disease-free survival, it may not lengthen overall survival. In such a case, side effects and failure to extend overall survival might outweigh the benefit of longer disease-free survival. Alternatively, the participant's improved quality of life during the tumour-free interval might outweigh other factors. Thus, because tumour response rates are often temporary and may not translate into long-term survival benefits for the participant, response rate is a reasonable measure of a treatment's effectiveness in a Phase II trial, whereas participant survival and quality of life are typically used as endpoints in a Phase III trial.

Pharmaceutical Kits

The present invention additionally provides for therapeutic kits containing the antisense oligonucleotide(s) or siRNAs for use in the treatment of cancer. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. In this case the container means may itself be an inhalant, syringe, pipette, eye dropper, or other such like apparatus, from which the composition may be administered to a patient.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, syringe, pipette, forceps, measured spoon, eye dropper or any such medically approved delivery vehicle.

To gain a better understanding of the invention described herein, the following examples are set forth. It will be understood that these examples are intended to describe illustrative embodiments of the invention and are not intended to limit the scope of the invention in any way.

EXAMPLES

Example 1: Design of Antisense Oligonucleotides to BRCA2

Three antisense oligonucleotides (OLIGOs) to BRCA2 were designed. The first OLIGO, named BR1, was based on the sequence of a siRNA (siRNA J-003462-08-0005) commercially available from Dharmacon Inc. (Lafayette, Colo.). BR1 has the following sequence:

[SEQ ID NO: 17]
5'-guaucuCTTGACGTuccuua-3' (40% GC content)

Wherein the lower case letters represent 2'O-methyl RNA and the upper case letters represent DNA. The OLIGO was fully phosphorothioated. The BR1 OLIGO targets the coding region, bases 7241-7259 of the BRCA2 mRNA, specifically, the following BRCA2 mRNA sequence:

[SEQ ID NO: 18]
5'-UAAGGAACGUCAAGAGAUAC-3'

Two other OLIGOs, BR2 and BR3, were designed using the NCI web-based BLAST program. The program was asked to design sequence-specific PCR primers. Pairs of primers were obtained for the coding region and the 3'-UTR of the BRCA mRNA. Based on these sequences, antisense sequences were designed and their specificity to BRCA2 mRNA was confirmed using the BLAST program.

OLIGO BR2 targets the coding region, bases 8574-8593 of the BRCA2 mRNA sequence, specifically:

[SEQ ID NO: 19]
5'-ACUCGGCCUGCUCGCUGGUA-3'

OLIGO BR2 has the following sequence:

[SEQ ID NO: 20]
5'-uaccagCGAGCAGGccgagu -3'

Wherein the lower case letters represent 2'O-methyl RNA and the upper case letters represent DNA. The OLIGO was fully phosphorothioated.

OLIGO BR3 targets the 3'-UTR, bases 10615-10634 (131 bases downstream of the translation stop site), of the BRCA2 mRNA sequence, specifically:

[SEQ ID NO: 21]
5'-CAGCGUUUGUGUAUCGGGCA-3'

OLIGO BR3 has the following sequence:

[SEQ ID NO: 22]
5'-ugcccgATACACAAacgcug -3'

Wherein the lower case letters represent 2'O-methyl RNA and the upper case letters represent DNA. The OLIGO was fully phosphorothioated.

Example 2: Inhibition of Proliferation of A549B Cells by an Antisense Oligonucleotide to BRCA2

The effect of an antisense oligonucleotide against BRCA2 on proliferation of non-small cell lung cancer (NSCLC) cells was tested. The BRCA2 antisense oligonucleotide tested in this experiment was BR1, described below. The experiment was carried out as follows.

Cell Culture Techniques.

Cell culture medium was purchased from Wisent, Inc. (St-Bruno, Quebec, Canada). Fetal bovine serum and Lipofectamine 2000 were purchased from Invitrogen, Inc. Cell culture plasticware was obtained from Invitrogen (Life technologies, Burlington, Ontario, Canada), Fisher Scientific (Unionville, Ontario), and VWR Canlab (Mississauga, Ontario).

Cultured cell lines were maintained in minimum essential medium a with nucleosides plus 10% fetal bovine serum and penicillin (50 units/mL)/streptomycin (50 mg/L) (growth medium). Cultures were incubated in a humidified atmosphere of 5% $CO_2$ at 37° C. Cultured cell lines were maintained and cytotoxicity assays conducted as described previously (3). Rapidly proliferating cells were utilized for establishing cultures of experimental cells, which were allowed to plate overnight in 25-$cm^2$ flasks prior to manipulation. An established cell line of non-small-cell lung carcinoma (NSCLC), A549b, which was propagated by serial dilution from a single cell of an A549 parent cell line, was used for the establishment of antisense activity of oligonucleotides. This cell line proliferates with a mean generation time of approximately 20 hours, and is capable of forming tumours in immunodeficient mice with a take rate of greater than 90%. Therefore, this cell line is a good model system that can be used in both in vitro and in vivo experiments to test the activity of OLIGOs.

Oligonucleotide Design and Sequences.

Oligonucleotides (OLIGOs) were ordered from Eurogentec (AnaSpec, Inc., Fremont, Calif., USA), for which the sequences are synthesized in Belgium. The chemistry of the OLIGOs is such that every phosphodiester bond in the nucleic acid backbone is a phosphorothioate. Nucleosides on the outer 6 positions of the sequence contain a methoxy moiety in the 2'-position of the ribose. This adds stability to the molecule against nucleolytic degradation, enhances binding to complementary sequences (decreases $\Delta G$ of binding) and enhances cellular accumulation. The middle 8 nucleosides do not contain the methoxy moiety, so as to minimize steric inhibition of access of ribonuclease H to the double-stranded nucleic acid (OLIGO-mRNA hybrid), leading to mRNA degradation.

Cells were treated with either BR1 or control antisense oligonucleotide OLIGO 32. The sequence of OLIGO 32 has no complementary matches with any known mRNA sequences. This sequence acts as a control for non-specific toxicity of the transfection procedure.

[SEQ ID NO: 23]
5'-atgcgcCAACGGTTcctaaa-3' (50% GC content)

The lowercase letters represent 2'-O-methyl RNA and uppercase letters represent DNA.

Transfection of OLIGOs

OLIGOs were introduced into cells with the use of Lipofectamine 2000 (LFA2K) (Invitrogen, Burlington, Ontario, Canada). OLIGOs were mixed with LFA2K at a ratio of 0.2 μg/ml per 10 nM OLIGO. The mixture was prepared at 11× the final concentration to which cells were exposed, so that 200 μL was added to 2 mL of medium in which cells were plated. As controls, cells were exposed to medium alone (no treatment), LFA2K alone at concentrations equivalent to those used in combination with OLIGOs (in some experiments only the maximum LFA2K concentration was used as a control), or OLIGO having no complementarity with any human mRNA. The OLIGO/LFA2K mixtures were then incubated at room temperature for 20 minutes, according to instructions supplied with the LFA2K, followed by addition of the OLIGOs to the cell medium. The OLIGO/LFA2K mix was then incubated (37° C.) on the cells for 4 hours, after which a second volume of medium was added. Cells were then incubated for 20 hours. Following this incubation, the OLIGO-containing medium was replaced with drug-free medium (i.e. medium without OLIGOs) and the cells were incubated for an additional 4 days. Following the 4-day incubation, the proliferation of the treated cells (fold-increase in cell number) was calculated as a percentage of that of control cells. Cell numbers were enumerated on an electronic particle counter (Beckman Coulter, Mississauga, ON). For the purpose of determining the anti-proliferative effect of antisense OLIGOs, the proliferation of cells treated with antisense OLIGOs was calculated as a percent of that of cells treated with an equivalent concentration of non-complementary control OLIGO (in this case OLIGO 32) mixed with an equivalent amount of LFA2K.

Figure 1:
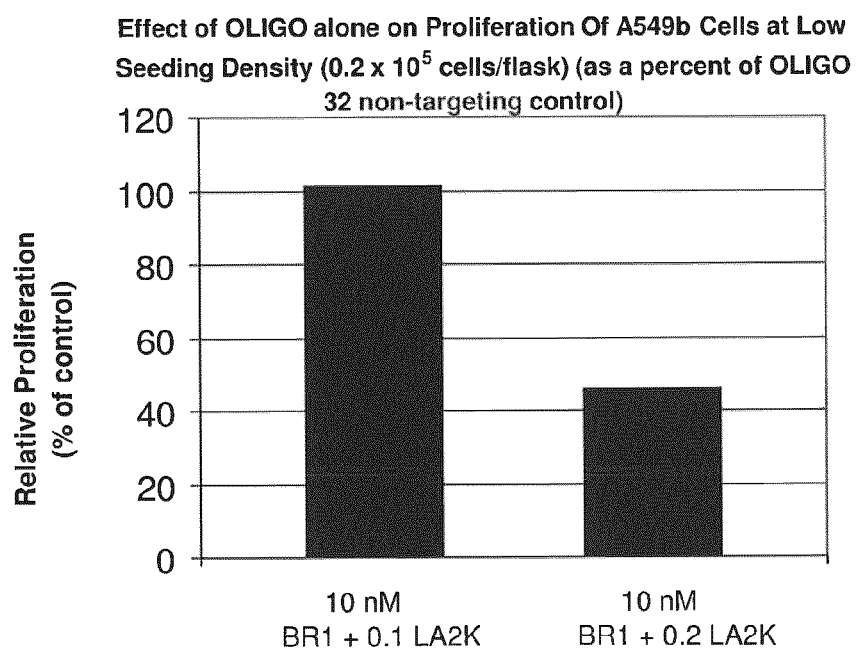
FIG. 1 depicts the inhibitory effect of the anti-BRCA2 antisense OLIGO BR1 on the proliferation of A549b cells.

Initial experiments were performed to optimize the ratio of LFA2K to the antisense oligonucleotide, and to determine what concentration of OLIGO was capable of inhibiting cell proliferation. The results of this experiment are shown in FIG. 1. As a single agent, OLIGO BR1, mixed with 0.2 μg/mL LFA2K, was able to inhibit proliferation of A549b cells by over 50%, compared with the control OLIGO 32 mixed with 0.2 □g/mL LFA2K.

Example 3: Inhibition of Proliferation of A549B Cells Pretreated with an Antisense Oligonucleotide to BRCA2 by Olaparib This experiment examined the effect of pre-treating A549b cells with the BRCA2 antisense oligonucleotide BR1 on the ability of the PARP (poly(ADP ribose) polymerase) inhibitor olaparib to inhibit proliferation of these cells. These experiments were carried out as follows.

Cells were cultured and maintained as described in Example 2. The antisense oligonucleotide sequences used were also as described in Example 2.

Cells were treated with OLIGOs and/or olaparib as follows.

OLIGOs were introduced into cells with the use of Lipofectamine 2000 (LFA2K) (Invitrogen, Burlington, Ontario, Canada). OLIGOs were mixed with LFA2K at a ratio of 0.2 μg/ml per 10 nM OLIGO. The mixture was prepared at 11× the final concentration to which cells were exposed, so that 200 μL was added to 2 mL of medium in which cells were plated. After incubating at room temperature for 20 minutes, according to manufacturer's instructions, the OLIGOs were added to the cell medium. The OLIGO/LFA2K mix was then incubated (37° C.) on the cells for 4 hours, after which a second volume of medium was added. Cells were then incubated for 20 hours. Following this incubation, the OLIGO-containing medium was replaced with OLIGO-free medium.

For cells treated with the drug olaparib, for the purposes of determining whether inhibitory activity was enhanced by the OLIGO pretreatment, olaparib was added at this time, in concentrations of from 0.01 μM to 3 μM. At this point, replicate flasks from the OLIGO-treatment were used to enumerate cell content, as this varied among treatments over the initial 24-hour exposure. This was done so that the effect of treatment with olaparib could be ascertained based on the cell population that was present at the time of initiation of exposure to olaparib. Exposure to the olaparib was initiated by addition of 0.2-volume of a preparation of the drug, at 6× final concentration in growth medium, to the fresh drug-free medium on the cells (1 ml of drug into 5 ml of medium). Following a further 4-day incubation, the proliferation of the treated cells (fold-increase in cell number) was calculated as a percentage of that of control cells. Cell numbers were enumerated on an electronic particle counter (Beckman Coulter, Mississauga, ON). As indicated in Example 1, for the purpose of determining the anti-proliferative effect of antisense OLIGOs alone, the proliferation of cells treated with antisense OLIGOs was calculated as a percent of that of cells treated with an equivalent concentration of non-complementary control OLIGO (in this case OLIGO 32). However, for the purpose of determining the anti-proliferative effect of olaparib against antisense or non-complementary (control) OLIGO-treated cells, the proliferation was calculated as a percent of cells treated with the respective OLIGO.

Figure 2:
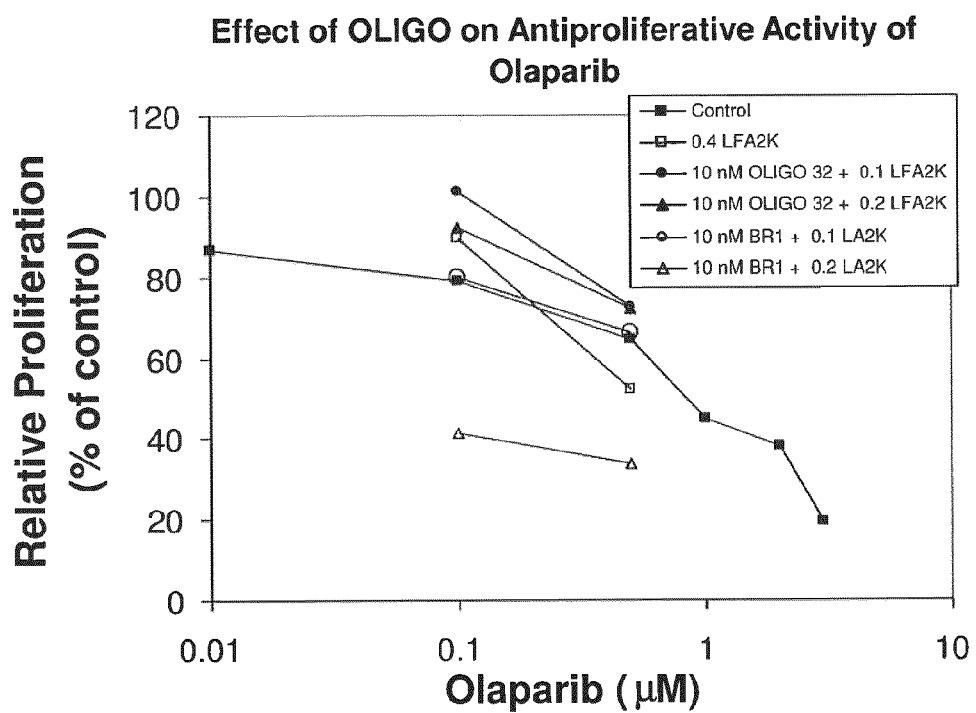
FIG. 2 depicts the effect of pretreatment with the anti-BRCA2 antisense OLIGO BR1 on the anti-proliferative activity of olaparib in A549b cells.

The results of this experiment are shown in FIG. 2, which shows that pretreatment of A549b cells with BR1 enhanced the anti-proliferative effect of olaparib by over 40% at a given concentration of olaparib. Interpreted in a different manner, if these curves are conservatively extrapolated, the concentration of olaparib required to inhibit proliferation of A549b cells by 50% (IC50) appears to be several orders of magnitude greater in the absence of BR1 than in its presence (approximate IC50 values of 5 and 0.05, respectively). This indicates the importance of PARP to the survival of drug-treated cells and demonstrates that in spite of the redundancies evolved into the DNA-repair system, PARP is essential to the maintenance of DNA integrity in the absence of BRCA2. It also suggests that BRCA1 does not function as a back-up system in the absence of BRCA2.

Example 4: Effect of an Antisense Oligonucleotide to BRCA2 Alone and in Combination with Olaparib on Proliferation of NSCLC Cells The experiments described in Examples 2 and 3 were repeated. The experimental steps were the same. However, the amount of LFA2K used differed in some cases, and additional concentrations of olaparib were tested with cells pretreated with BR1 or control oligonucleotides. The results are shown in FIGS. 3 to 6. Modifications with respect to the amount of BR1, LFA2K and the concentrations of olaparib used are shown on the Figures themselves.

Figure 3:
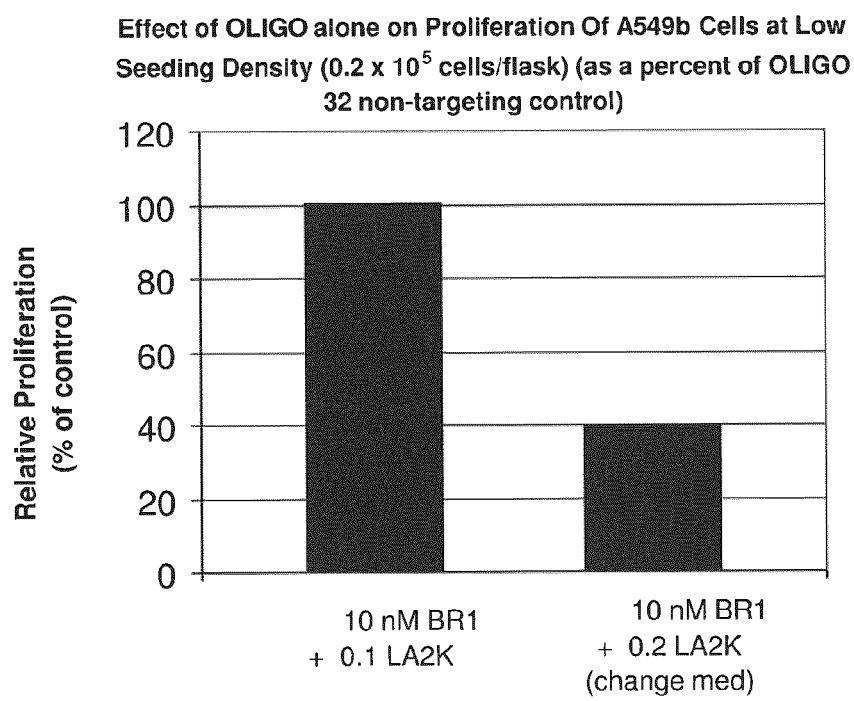
FIG. 3 depicts the result of another experiment demonstrating the effect of the anti-BRCA2 antisense OLIGO BR1 on the proliferation of A549b cells.
Figure 4:
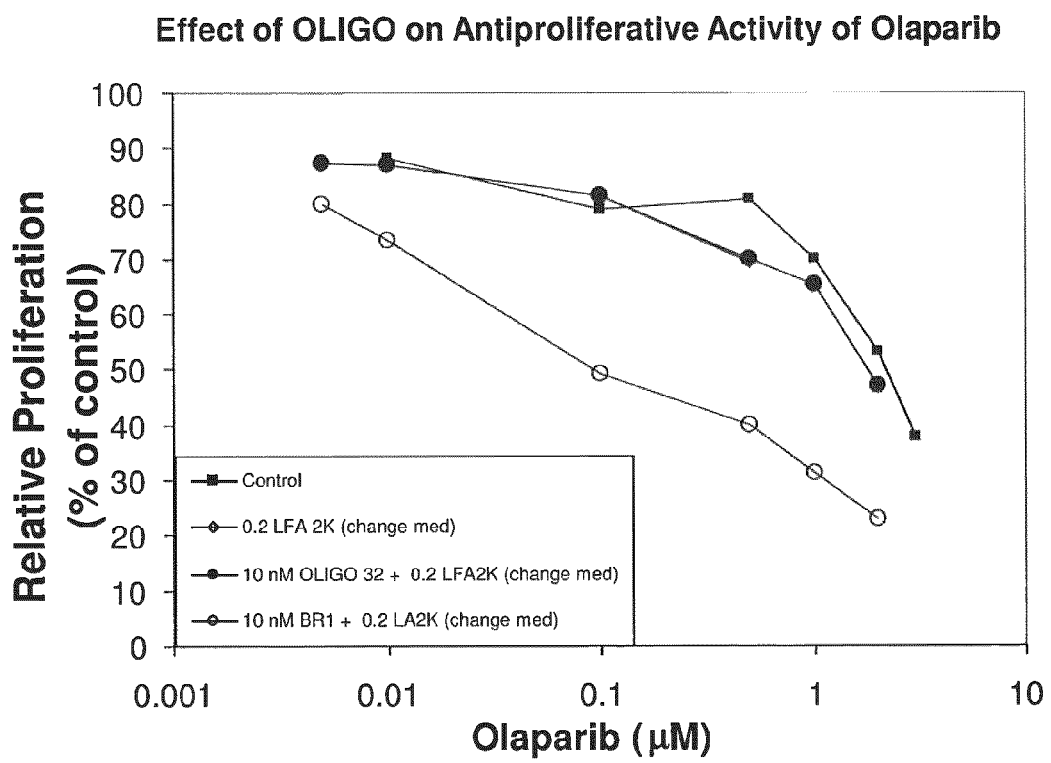
FIG. 4 depicts the result of another experiment demonstrating the effect of pretreatment with the anti-BRCA2 antisense OLIGO BR1 on the anti-proliferative activity of olaparib in A549b cells.
Figure 5:
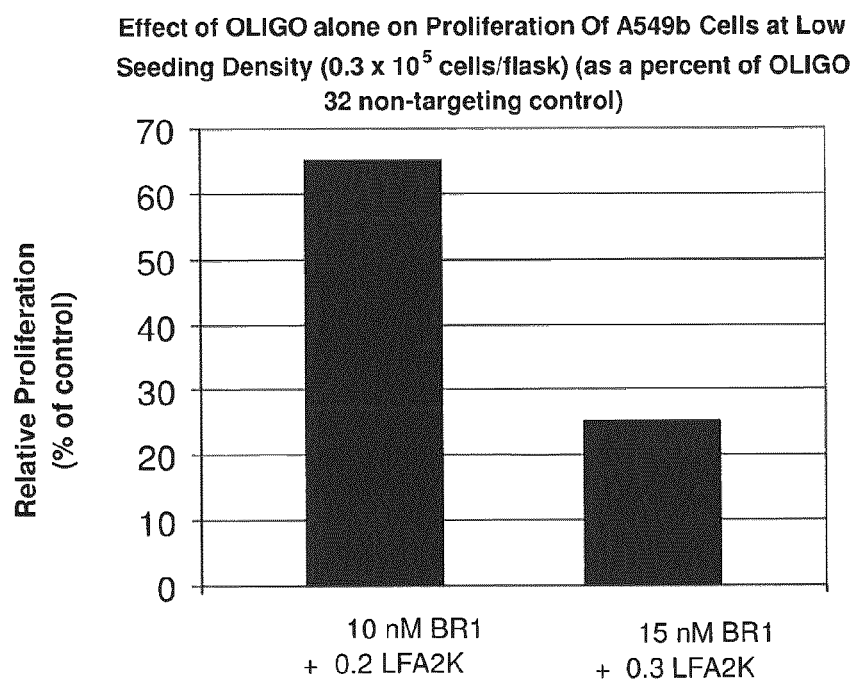
FIG. 5 depicts the result of a third experiment demonstrating the effect of the anti-BRCA2 antisense OLIGO BR1 on the proliferation of A549b cells.
Figure 6:
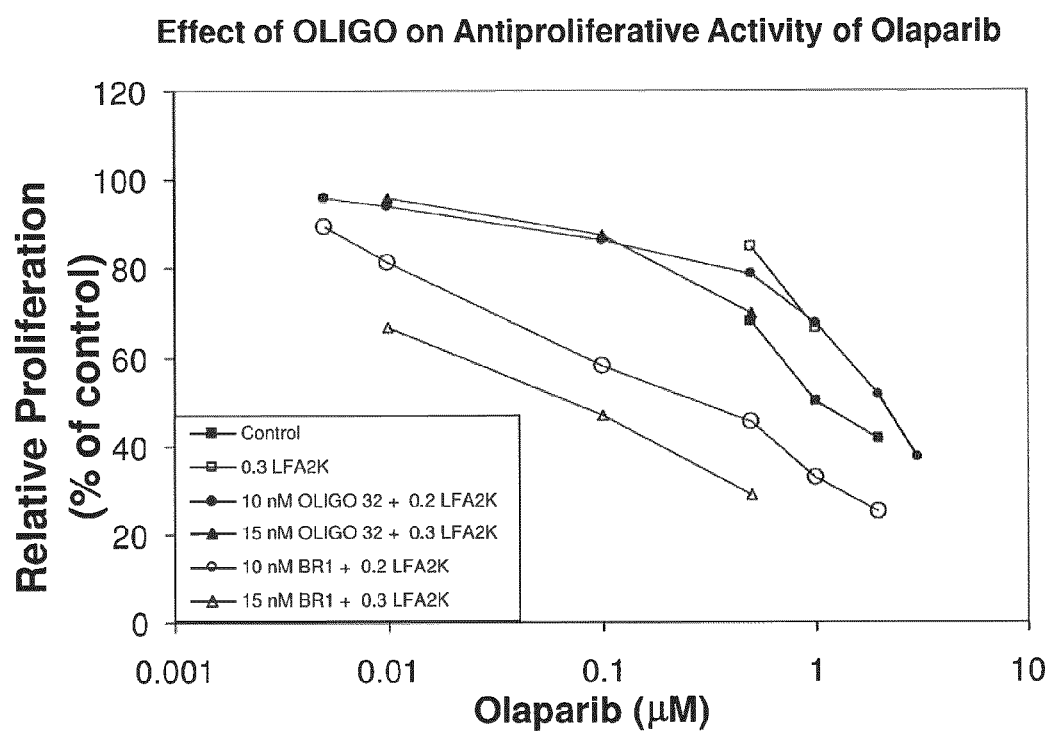
FIG. 6 depicts the result of a third experiment demonstrating the effect of pretreatment with the anti-BRCA2 antisense OLIGO BR1 on the anti-proliferative activity of olaparib in A549b cells.

The results showed that OLIGO BR1, when combined with an optimal concentration of transfection reagent, again inhibited proliferation on its own as shown in FIG. 3, and enhanced the antiproliferative activity of olaparib, as shown in FIG. 4. As shown in FIGS. 5 and 6, a higher concentration of BR1 had greater inhibition as a single agent, and slightly greater enhancement of olaparib toxicity compared to the previously used 10 nM.

Example 5: Effect of Pretreatment of A549B Cells with Antisense Oligonucleotides to BRCA2 on the Ability of Cisplatin to Inhibit Proliferation The ability of anti-BRCA2 OLIGOs to enhance the antiproliferative activity of a PARP inhibitor as shown in Examples 3 and 4 suggested that DNA damage occurs spontaneously in proliferating tumour cells, or that these enzymes are also involved in the normal replication of DNA. As such, it suggested that if DNA were damaged by addition of a chemotherapy drug, inhibition of BRCA2 might also enhance the cytotoxicity of the drug. In order to determine if this was the case, therefore, cells were treated with the DNA cross-linking agent cisplatin following transfection with OLIGO BR1 or with an antisense OLIGO that targets the 3'-UTR of the BRCA2 mRNA, OLIGO BR3.

These experiments were carried out essentially as described in Example 3, with the following changes. The drug tested was cisplatin instead of olaparib, and cisplatin was tested in concentrations ranging from 0.5 µM to 2 µM.

The BRCA2 antisense oligonucleotides used were BR1 and BR3. In these experiments, the control oligonucleotide was OLIGO 491S (also referred to as OLIGO 91S). OLIGO 491S is a control sequence that, like OLIGO 32, has no matching complementary mRNA sequences. The sequence of the OLIGO 491S oligonucleotide is:

[SEQ ID NO: 24]
5'-ggagtgCGTGAGTCgatgta-3' (55% GC content)

Figure 7A:
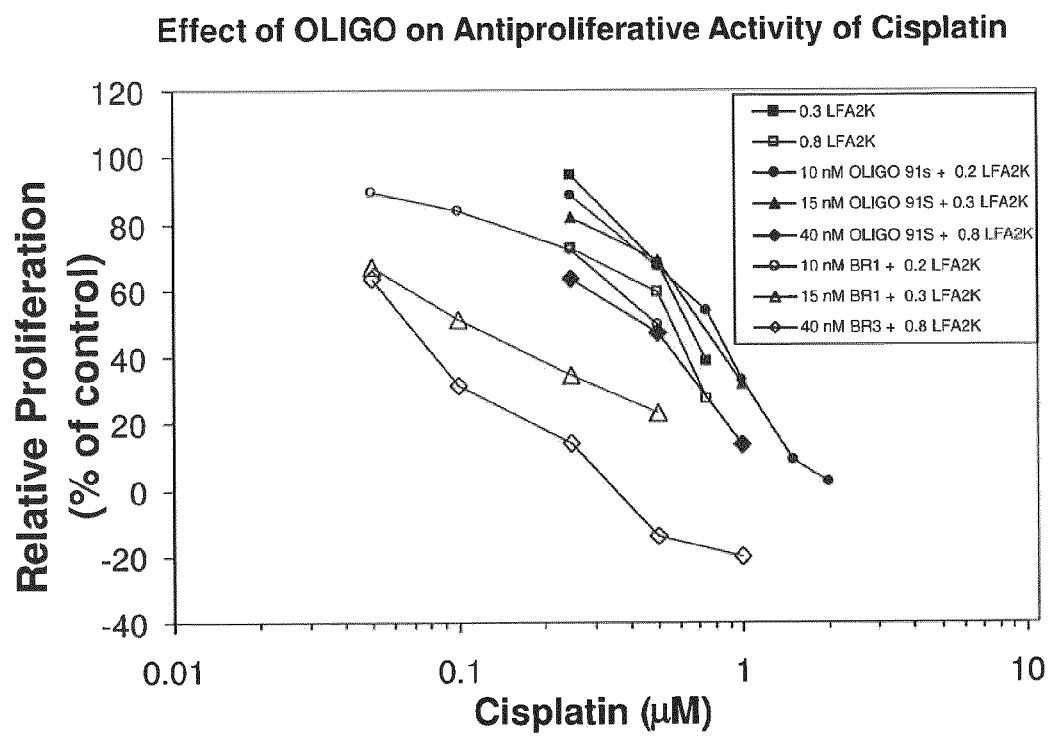
FIGS. 7A and 7B depict the effect of pretreatment with the anti-BRCA2 antisense OLIGO BR1 or the anti-BRCA2 antisense OLIGO BR3 on the anti-proliferative activity of cisplatin in A549b cells.
Figure 7B:
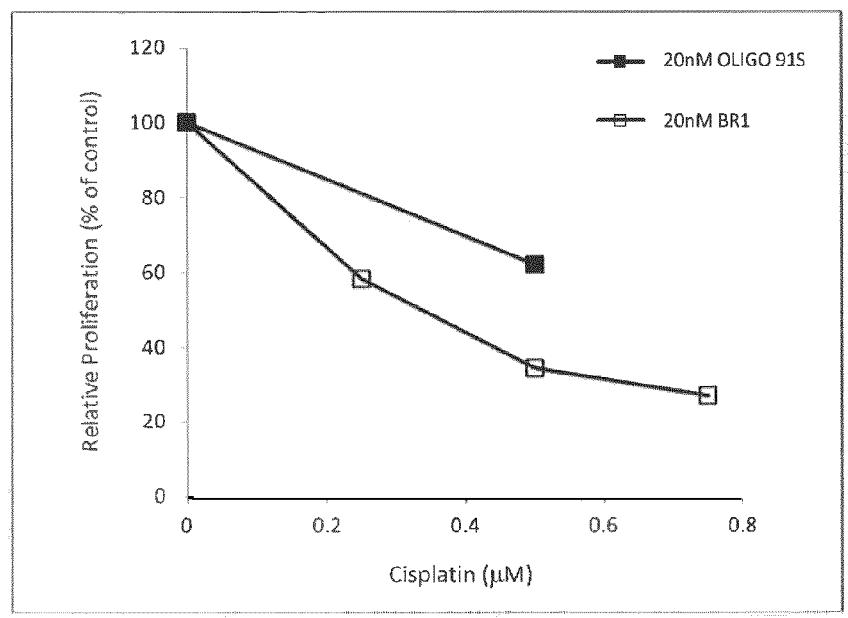
Figure 8:
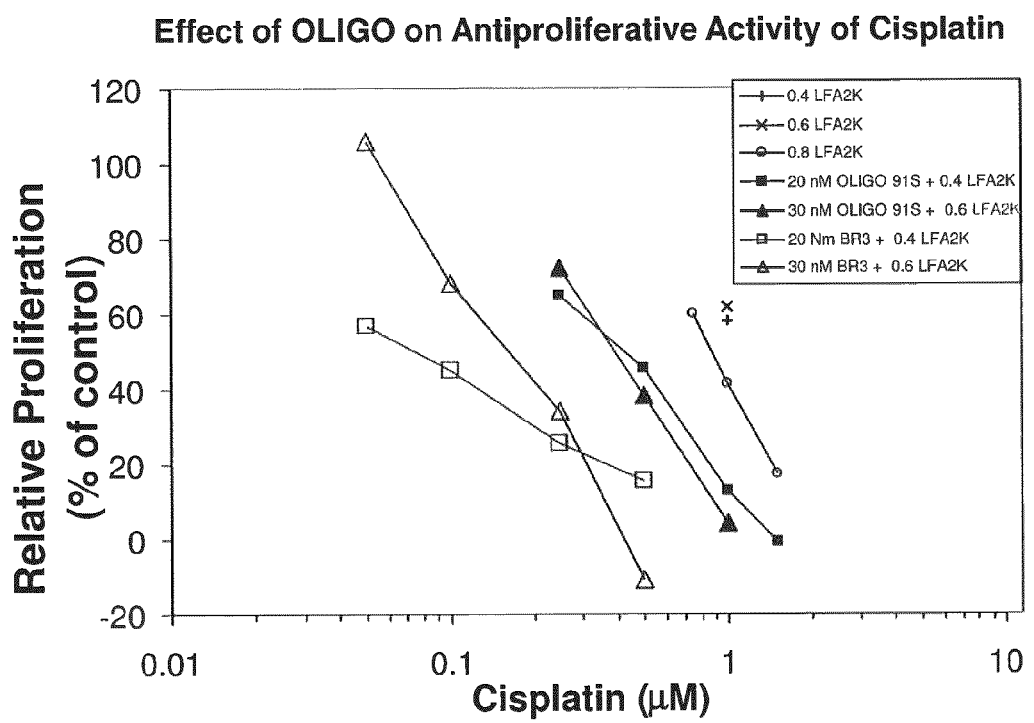
FIG. 8 depicts the results of a second experiment showing the effect of pretreatment with the anti-BRCA2 antisense OLIGO BR3 on the anti-proliferative activity of cisplatin in A549b cells.

The results of these experiments are shown in FIGS. 7 and 8. Compared to the non-complementary control, in this case OLIGO 491S, both BR1 and BR3 were able to enhance the cytotoxicity of cisplatin by approximately 5- to 10-fold. To put these results in perspective, if such enhancement of antitumour activity could be achieved in patients, it would significantly decrease toxicities related to hearing loss, kidney damage, nausea and vomiting, and bone marrow depression.

Example 6: Ability of a Combination of Antisense Oligonucleotides to BRCA2 to Inhibit Proliferation of A549B Cells The following experiment was carried out to test the effect of combining the anti-BRCA2 OLIGOs, BR1 and BR3, at concentrations that had very little inhibitory activity as single agents, on the proliferation of A549b cells.

Figure 9:
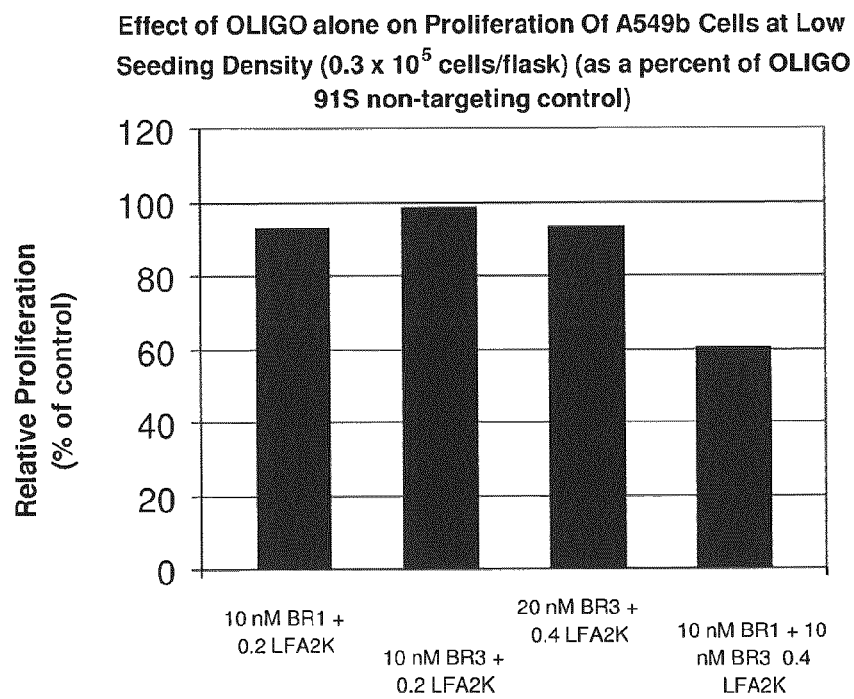
FIG. 9 depicts the effect of treating A549b cells with two different antisense oligonucleotides against BRCA2 (BR1 and BR3) on the proliferation of A549b cells.

The experiments were carried out as described in Example 2, with the exception that the control OLIGO used was OLIGO 491S. The results are shown in FIG. 9 and demonstrate that, at concentrations of BR1 and BR3 that had very little inhibitory activity as single agents, these two OLIGOs inhibited A549b proliferation greater than would be predicted by an additive effect.

Example 7: Effect of Pretreatment with Antisense Oligonucleotides to BRCA2 on the Ability of Cisplatin to Inhibit Proliferation of A549B Cells The following experiment was carried out in order to determine whether the combination of BR1 and BR3 tested in Example 6 could also enhance the effect of cisplatin on the proliferation of A549b cells. The experiment was carried out as described in Example 3, except that the concentration of BR1 and BR3 antisense oligonucleotides were as described in Example 6, the control oligonucleotide used was OLIGO 491S, and the drug used was cisplatin.

Figure 10:
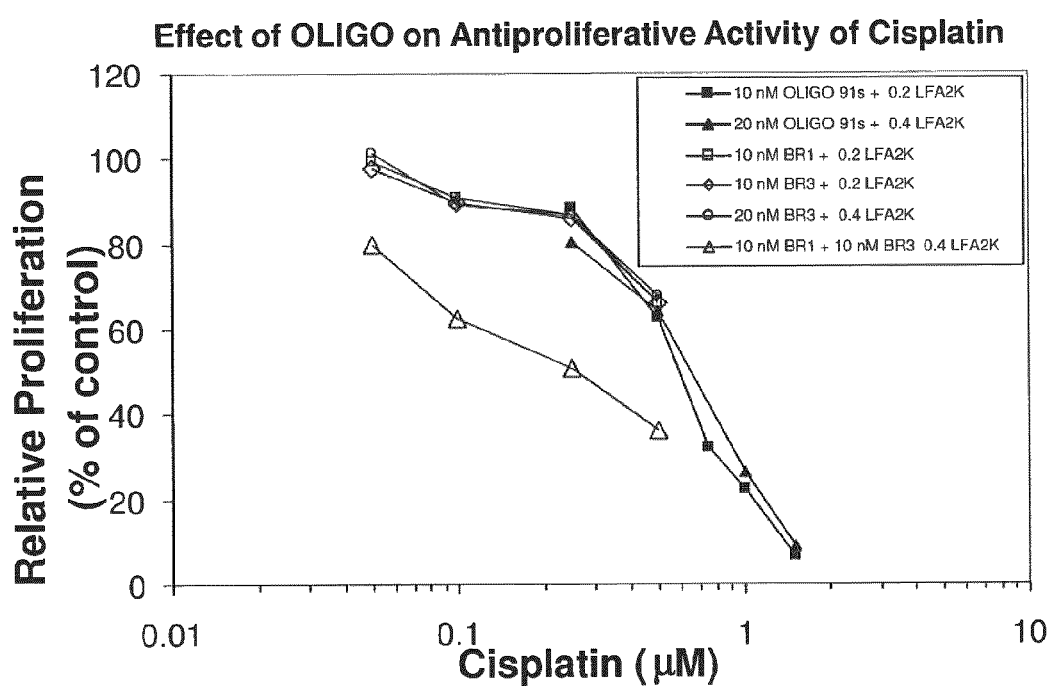
FIG. 10 depicts the effect of pretreatment with the anti-BRCA2 antisense OLIGOs BR1 and BR3 on the anti-proliferative activity of cisplatin in A549b cells.
Figure 11:
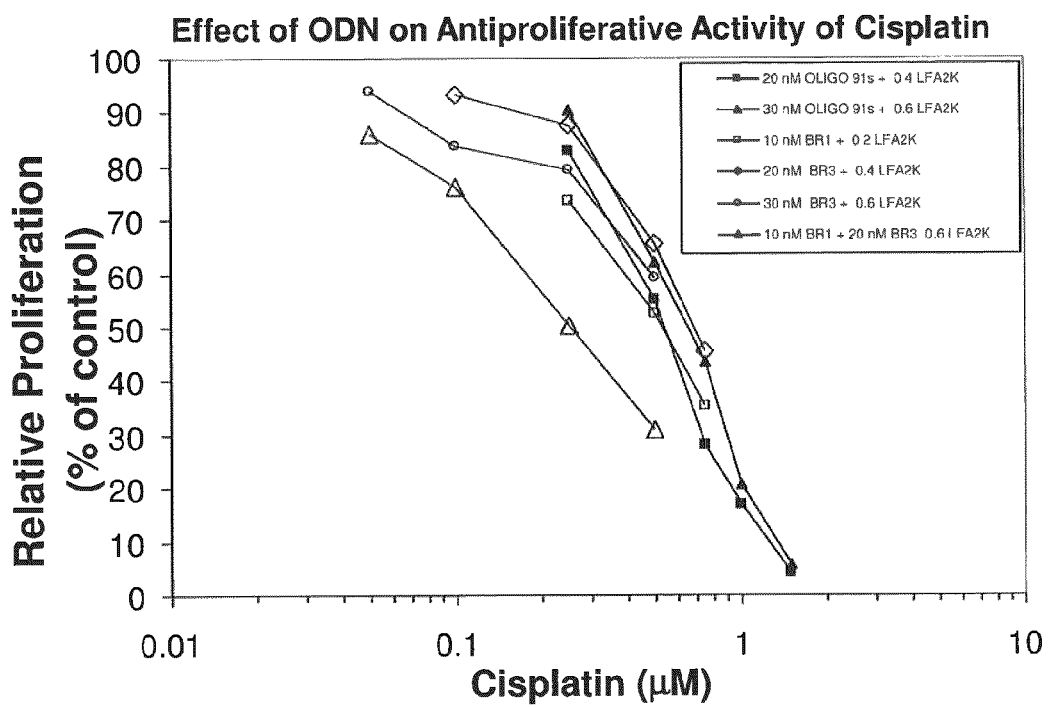
FIG. 11 depicts the results of a second experiment demonstrating the effect of pretreatment with the anti-BRCA2 antisense OLIGOs BR1 and BR3 on the anti-proliferative activity of cisplatin in A549b cells.

The results of this experiment are shown in FIGS. 10 and 11. When pretreatment of A549 cells with a combination of OLIGOs BR1 and BR3 was followed by exposure to cisplatin, the anti-proliferative activity of cisplatin was enhanced approximately 5-fold by concentrations of OLIGO that had negligible effect on proliferation on their own or even at concentrations equivalent to that of the combination.

Example 8: Effect of a Combination of an Antisense Oligonucleotide to BRCA2 and an Antisense Oligonucleotide to Thymidylate Synthase on the Proliferation of A549B Cells OLIGO 83 is an antisense oligonucleotide targeted to the 3'-untranslated region of mRNA of thymidylate synthase (TS) and down-regulates TS mRNA and protein, inhibits proliferation of cancer cells, and enhances cytotoxicity of TS-inhibitory drugs such as 5-fluorodeoxyuridine and pemetrexed (4, 5). Given that TS-inhibitors are often used in combination with platinum drugs against some tumour types, such as carcinomas of the breast, lung, colon, and head and neck, the combination of OLIGOs targeting both TS and BRCA2 was tested to determine whether they could be used to enhance the antitumour activity of such drug combinations. Initially, the combination of OLIGO 83 and BR3 was tested in A549b cells to determine the effect of this combination on cell proliferation.

The experiment was carried out as described in Example 2, except that the oligonucleotides tested were BR3 and OLIGO 83. The control oligonucleotide was OLIGO 491S. The sequence of OLIGO 83 is:

[SEQ ID NO: 25]
5'-gccaguGGCAACATccuuaa-3' (50% GC content).

The lowercase letters represent 2'-O-methyl RNA and uppercase letters represent DNA. OLIGO 83 is fully phosphorothioated.

Figure 12:
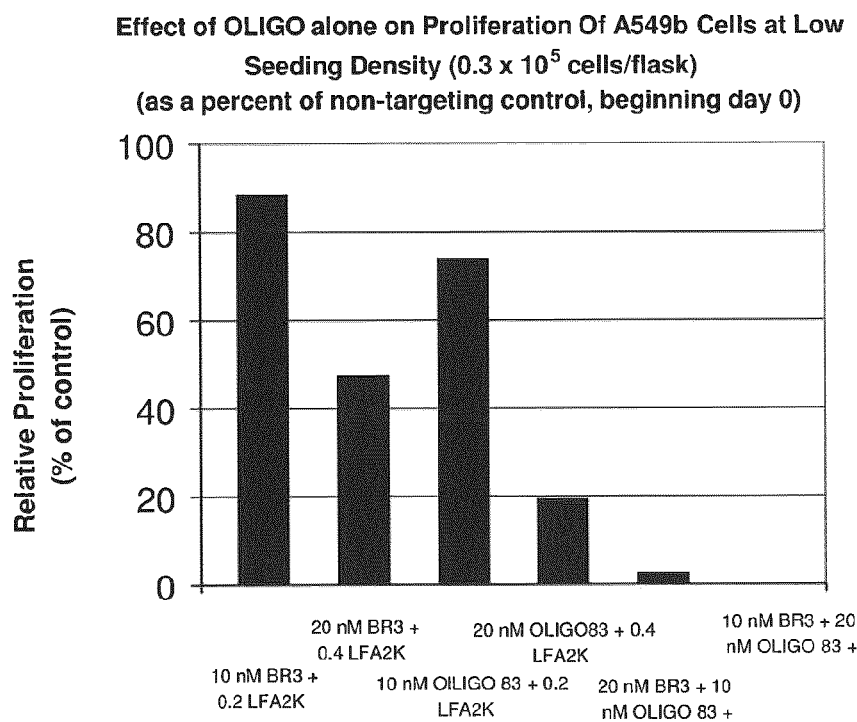
FIG. 12 depicts the effect of treatment with the anti-BRCA2 antisense OLIGO BR3 and the anti-thymidylate synthase (TS) oligonucleotide OLIGO 83 on the proliferation of A549b cells.

The results of this experiment are shown in FIG. 12. In this preliminary assay, compared to an equivalent concentration of non-targeting OLIGO (491S), the combination of BR3 and OLIGO 83 caused greater inhibition of proliferation than would be predicted based on the inhibition caused by each OLIGO alone, at the respective concentrations. For example, relative proliferation following treatment with 10 nM of BR3 was approximately 85% and following treatment with 20 nM OLIGO 83 was approximately 20%. The relative proliferation following combined treatment was approximately 0%. This result suggests that there may be a greater than additive or synergistic anti-tumour effect of this OLIGO combination, and that this combination could potentially synergistically enhance the effect of drugs such as 5-fluorouracil and cisplatin when administered together.

Example 9: Effect of Pretreatment of A549B Cells with Anti-BRCA2 Oligo BR1 on Cytotoxicity of Melphalan Against Medium Density A549B Cells This experiment examined the effect of pretreating A549b cells with the BRCA2 antisense oligonucleotide BR1 on the cyotoxicity of melphalan.

These experiments were carried out essentially as described in Example 3, with the following changes. The drug tested was melphalan in concentrations ranging from 2 µM to 10 µM.

The BRCA2 antisense oligonucleotide used was BR1. In these experiments, the control oligonucleotide was OLIGO 32.

Figure 13:
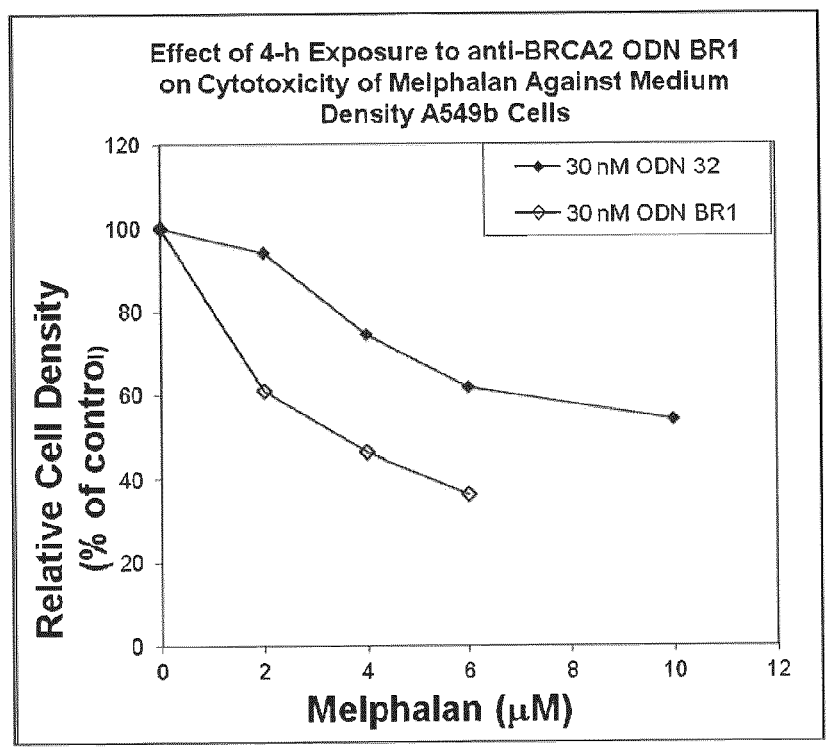
FIG. 13 depicts the effect of pretreatment of A549b cells with anti-BRCA2 OLIGO BR1 on the cytotoxicity of melphalan against medium density A549b cells. In this figure and FIGS. 14 to 18, "ODN" was used in place of "OLIGO" as an abbreviation for oligonucleotide.

The results of these experiments are shown in FIG. 13. Compared to the non-complementary control, in this case OLIGO 32, BR1 was able to enhance the cytotoxicity of melphalan.

Example 10: Effect of Pretreatment of A549B Cells with Anti-BRCA2 Oligo BR1 on Cytotoxicity of Carboplatin Against Medium Density A549B Cells This experiment examined the effect of pretreating A549b cells with the BRCA2 antisense oligonucleotide BR1 on the cyotoxicity of carboplatin against A549b cells.

These experiments were carried out essentially as described in Example 3, with the following changes. The drug tested was carboplatin at concentrations ranging from 5 µM to 40 µM.

The BRCA2 antisense oligonucleotides used were BR1. In these experiments, the control oligonucleotide was OLIGO 32.

Figure 14:
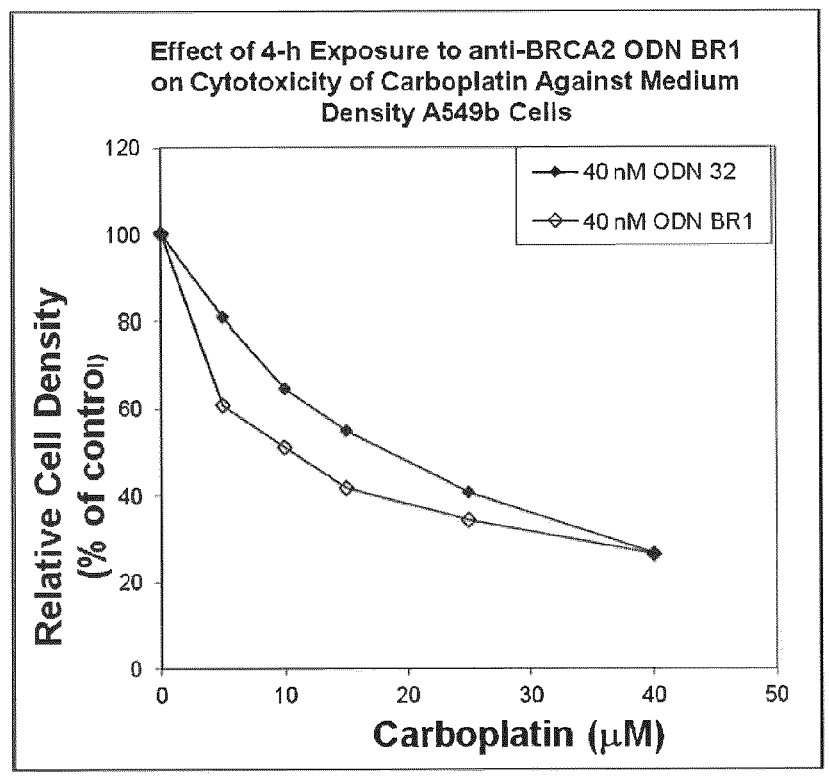
FIG. 14 depicts the effect of pretreatment of A549b cells with anti-BRCA2 OLIGO BR1 on the cytotoxicity of carboplatin against medium density A549b cells.

The results of these experiments are shown in FIG. 14. Compared to the non-complementary control, in this case OLIGO 32, BR1 was able to enhance the cytotoxicity of carboplatin.

Example 11: Effect of Pretreatment of A549B Cells with Anti-BRCA2 Oligo BR1 on Cytotoxicity of Oxaliplatin Against Low Density A549B Cells This experiment examined the effect of pretreating A549b cells with the BRCA2 antisense oligonucleotide BR1 on the cyotoxicity of oxaliplatin.

These experiments were carried out essentially as described in Example 3, with the following changes. The drug tested was oxaliplatin was tested in concentrations ranging from 0.2 µM to 2.5 µM.

The BRCA2 antisense oligonucleotide used was BR1. In these experiments, the control oligonucleotide was OLIGO 32.

Figure 15:
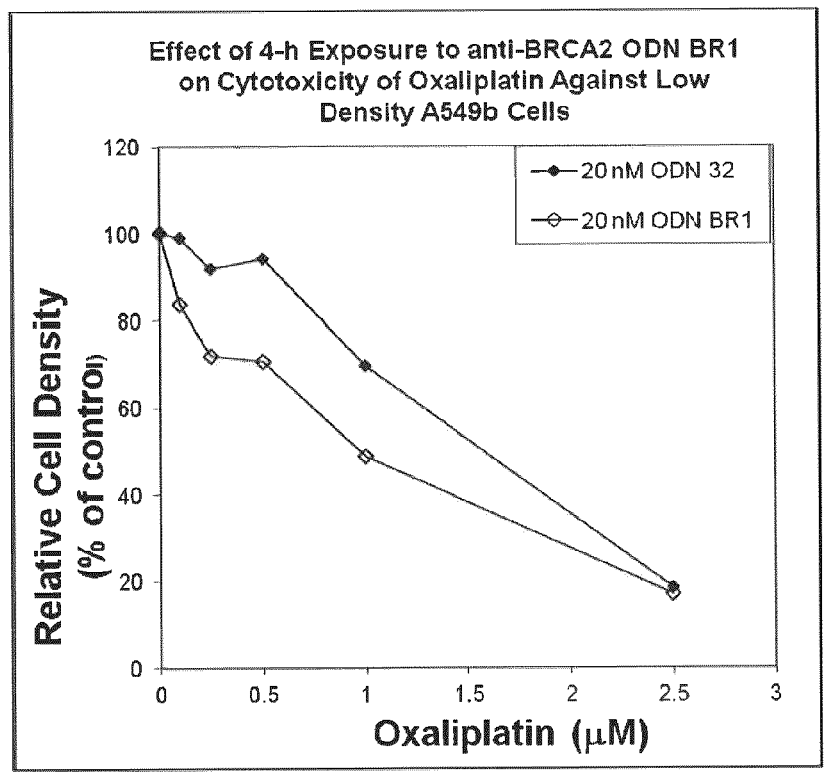
FIG. 15 depicts the effect of pretreatment of A549b cells with anti-BRCA2 OLIGO BR1 on the cytotoxicity of oxaliplatin against low density A549b cells.

The results of these experiments are shown in FIG. 15. Compared to the non-complementary control, in this case OLIGO 32, BR1 was able to enhance the cytotoxicity of oxaliplatin at lower doses.

Example 12: Antisense Ts Oligo 83 and Antisense BRCA2 Oligo BR1 Act Independently to Reduce Thymidylate Synthase and BRCA2 mRNA Levels This experiment tested the effect of treatment of antisense OLIGOs 83 and BR1 on both TS and BRCA2 mRNA levels.

Briefly, A549 cells seeded at a density of $2.0 \times 10^5$ per flask were transfected with 20 nM of OLIGO specific for each target or control OLIGO using Lipofectamine 2000 as the transfection reagent. Twenty four hours post-transfection mRNA was extracted and reverse transcribed into cDNA. RT-qPCR was performed for target mRNA levels using TaqMan reagents according to established protocols.

Figure 16:
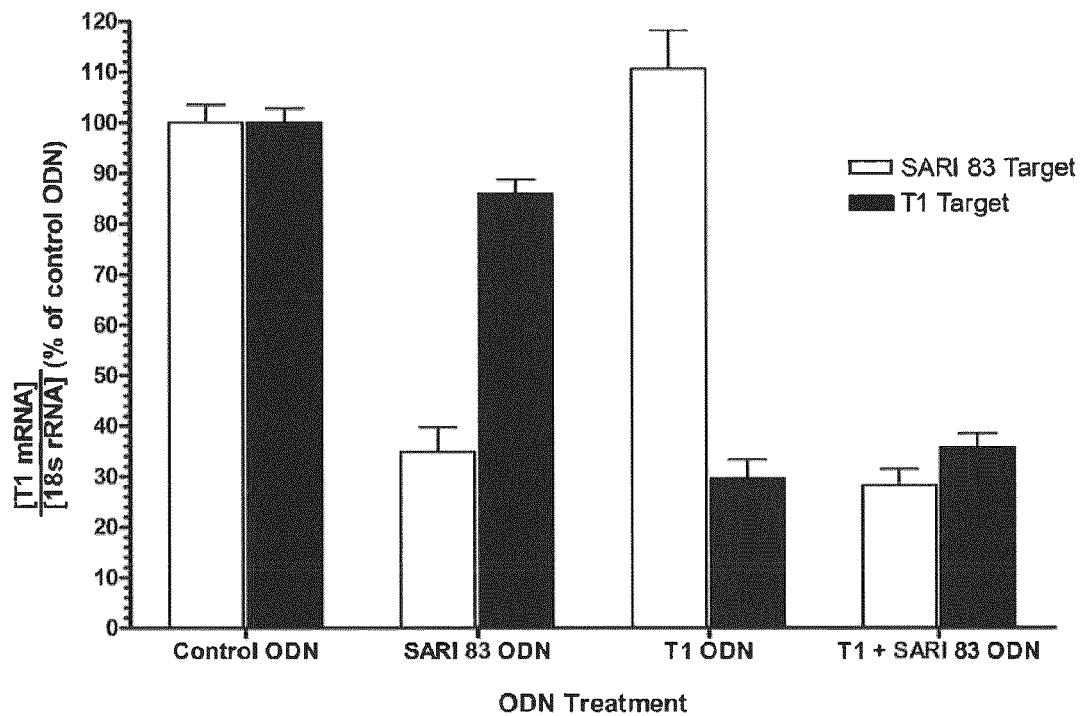
FIG. 16 illustrates that antisense TS OLIGO and antisense BR1 OLIGO act independently to reduce thymidylate synthase and BRCA2 mRNA levels.
Figure 17A:
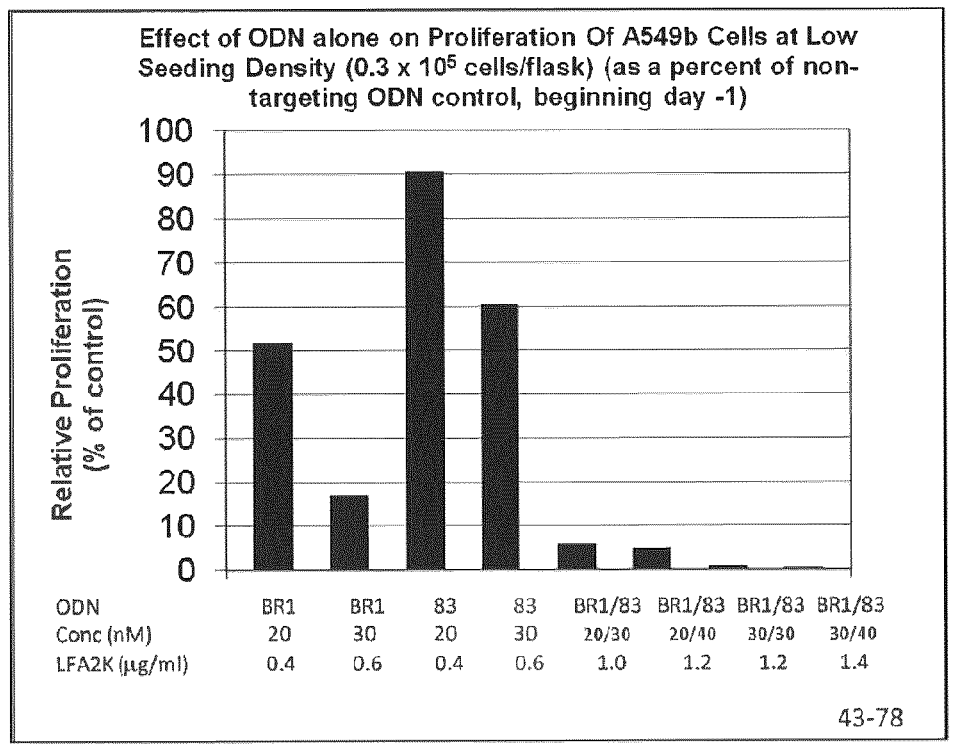
FIGS. 17A to 17E illustrate synergistic anti-proliferative effect of Antisense TS OLIGO and antisense BR1 on A549b cells using concentrations of oligonucleotides as detailed in the Figure.
Figure 17B:
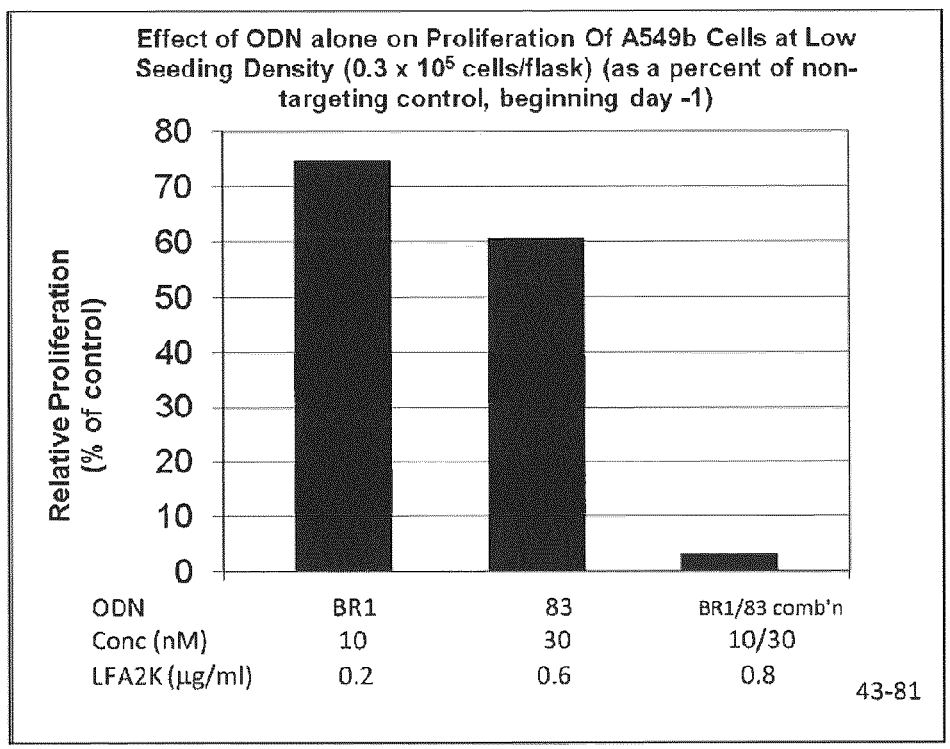
Figure 17C:
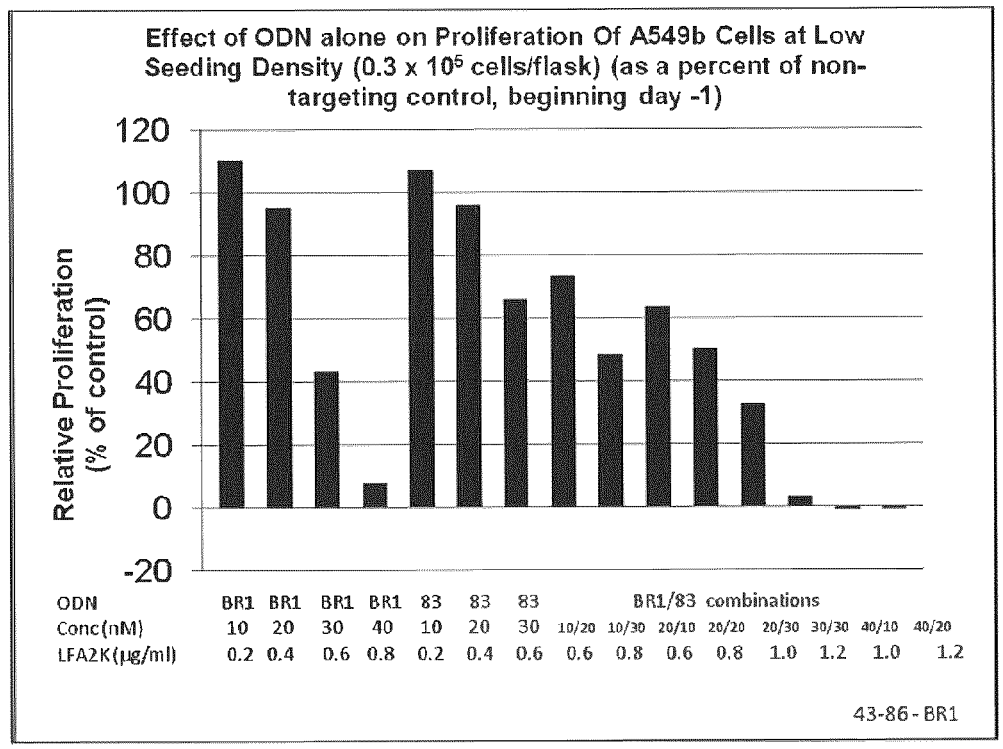
Figure 17D:
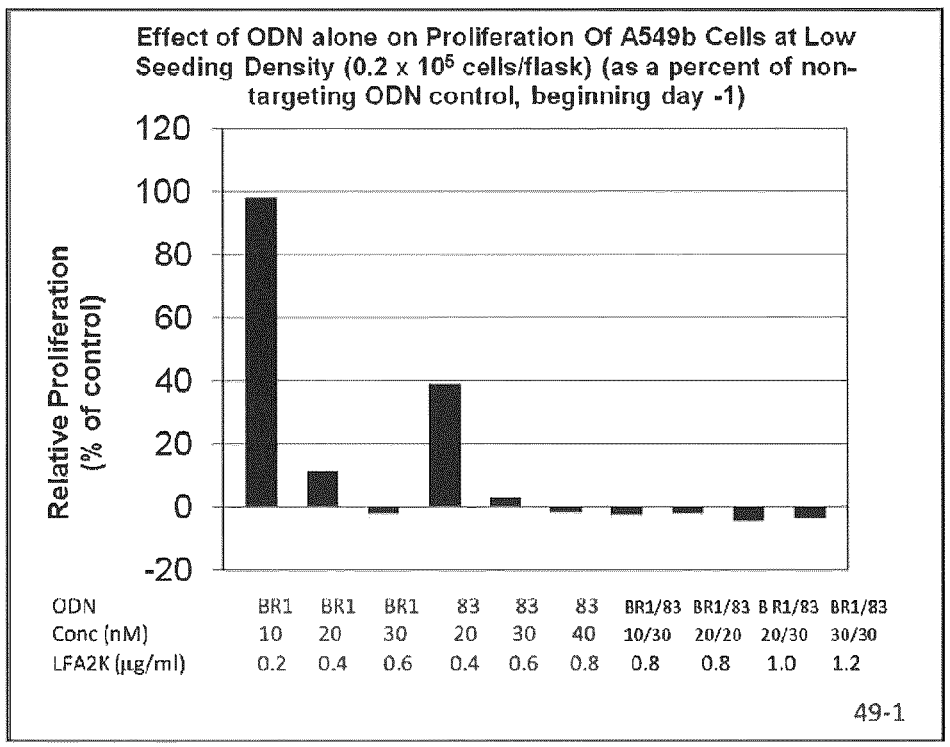
Figure 17E:
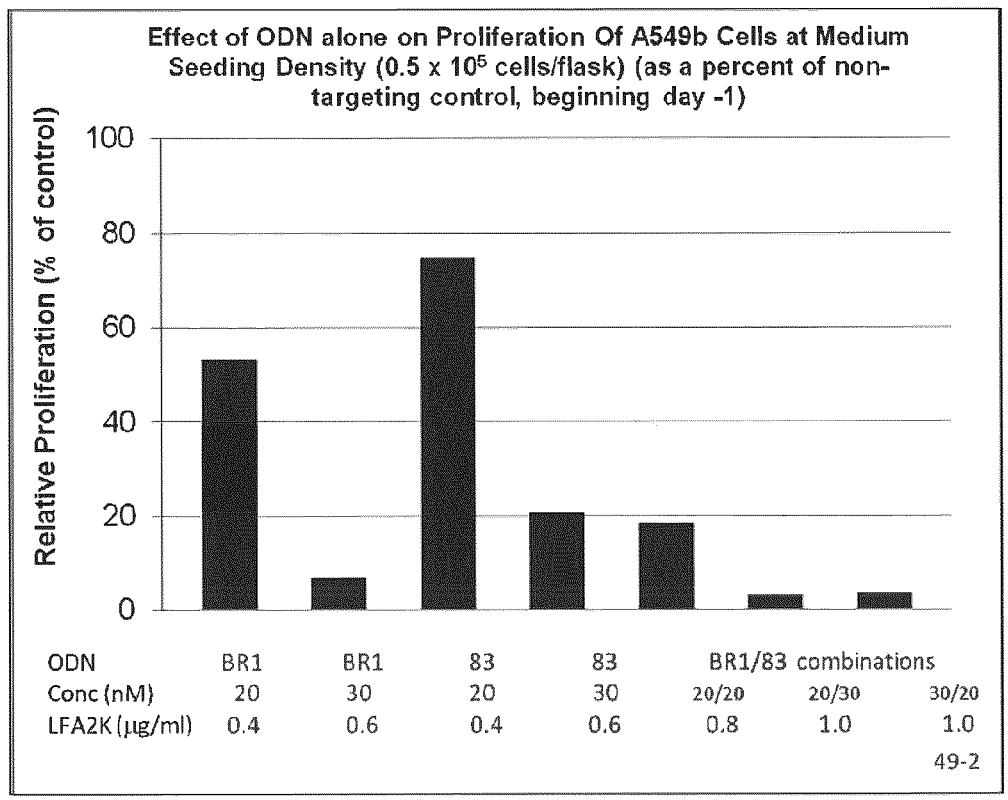

As shown in FIG. 16, antisense TS (labeled SARI 83) and antisense BR1 (labeled T1) OLIGO act independently to reduce TS and T1 mRNA. In particular, antisense OLIGO-mediated reduction in TS mRNA has no significant effect on BRCA2 mRNA, and antisense OLIGO-mediated reduction in BRCA2 mRNA has no significant effect on TS mRNA. In addition, simultaneous treatment with antisense TS OLIGO and antisense BR1 OLIGO reduces TS and BRCA2 mRNAs to the same degree as independent, non-concomitant treatment. Therefore, additive or greater-than-additive effects of antisense TS and BR2 OLIGOs on tumour cell proliferation cannot be attributed to additive/greater-than-additive capacity to reduce mRNA.

Example 13: Synergistic Effect of Antisense TS Oligo and Antisense BR1

This experiment examined the combined effect of BRCA2 antisense oligonucleotide BR1 and antisense TS oligonucleotide OLIGO 83 on proliferation of A549b cells.

These experiments were carried out essentially as described in Example 2, after which one volume of medium was added, and cells were further incubated for 20 hours. OLIGO-containing medium was removed and replaced with fresh medium. Cells were incubated for 4 days, at which time cell number was counted. Proliferation was calculated as a percent of non-targeting OLIGO-treated controls.

The experimental steps were the same for the experiments detailed in FIGS. 17A-17E. However, the amount of LFA2K used differed in some cases, and concentrations of OLIGO BR1 and OLIGO 83 were varied. Modifications with respect to the amount of BR1, OLIGO83 and LFA2K are shown on the Figures themselves.

As is shown in FIGS. 17A-17E, the combination of OLIGO BR1 and OLIGO 83 caused greater inhibition of proliferation than what would be expected by an additive effect of each OLIGO alone.

Example 14: Synergistic Effect of Antisense TS Oligo and Antisense BR3

This experiment examined the combined effect of BRCA2 antisense oligonucleotide BR3 and antisense TS oligonucleotide OLIGO 83 on proliferation of A549b cells.

These experiments were carried out essentially as described in Example 2, after which one volume of medium was added, and cells were further incubated for 20 hours. OLIGO-containing medium was removed and replaced with fresh medium. Cells were incubated for 4 days, at which time cell number was counted. Proliferation was calculated as a percent of non-targeting OLIGO-treated controls.

Figure 18A:
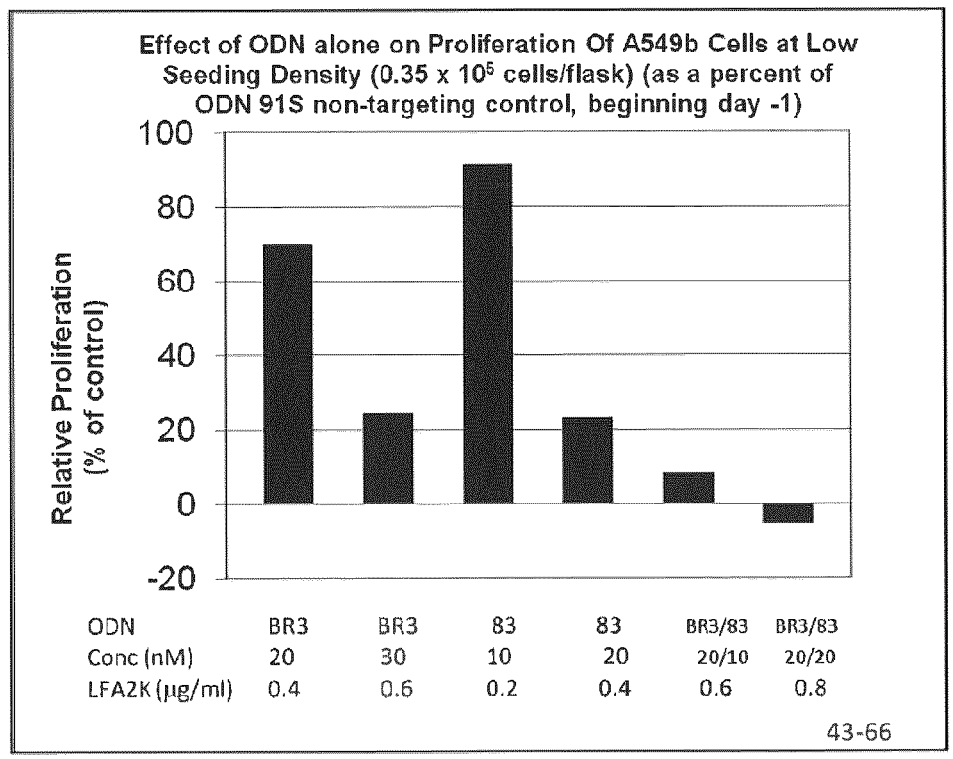
FIGS. 18A and 18B illustrate synergistic anti-proliferative effect of Antisense TS OLIGO and antisense BR3 using concentrations of oligonucleotides as detailed in the Figure.
Figure 18B:
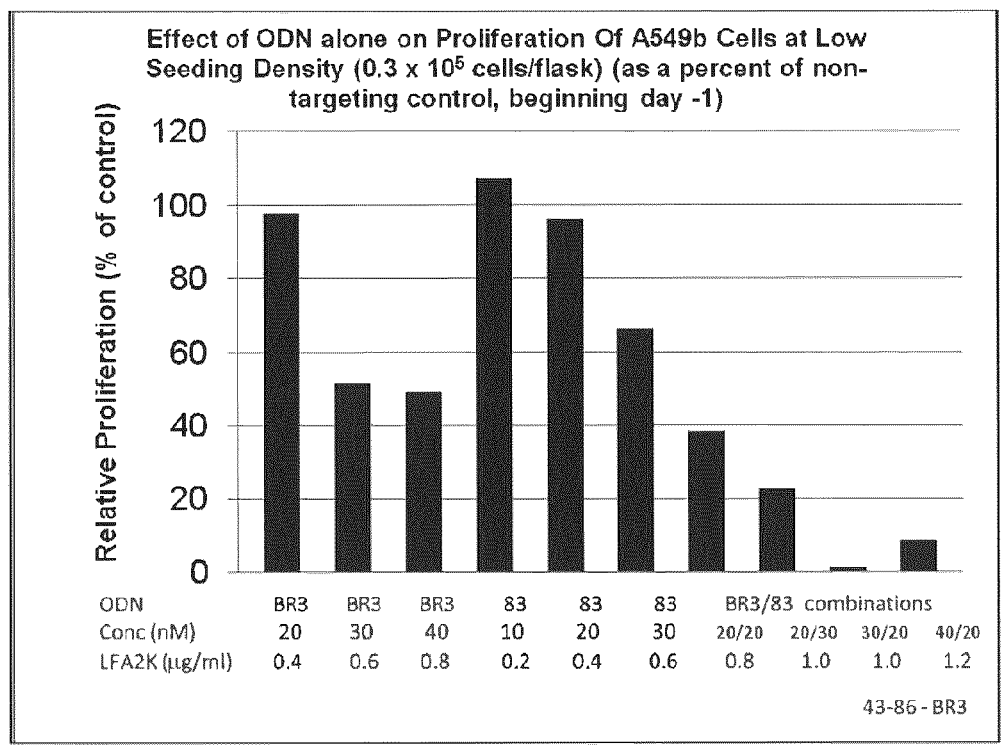

The experimental steps were the same for the experiments detailed in FIGS. 18A and 18B. However, the amount of LFA2K used differed in some cases, and concentrations of OLIGO BR3 and OLIGO 83 were varied. Modifications with respect to the amount of BR3, OLIGO83 and LFA2K are shown on the Figures themselves.

As is shown in FIGS. 18A and 18B, the combination of OLIGO BR3 and OLIGO83 caused greater inhibition of proliferation than what would be expected by an additive effect of each OLIGO alone.

Example 15: Effect of Combination of Four Anti-BRCA2 siRNAs on Cytotoxicity of Cisplatin in A549B Cells This experiment examined the effect of four anti-BRAC2 siRNA, total 5 nM, on the cytotoxity of cisplatin in A549b cells.

These experiments were carried out essentially as described in Example 2, after which one volume of medium was added, and cells were further incubated for 20 hours. siRNA-containing medium was removed and replaced with fresh medium. Cisplatin was added to the final concentration indicated, and as described in Example 3. Cells were incubated for 4 days, at which time cell number was counted. Proliferation was calculated as a percent of siRNA-treated, non-cisplatin-treated controls.

Figure 19:
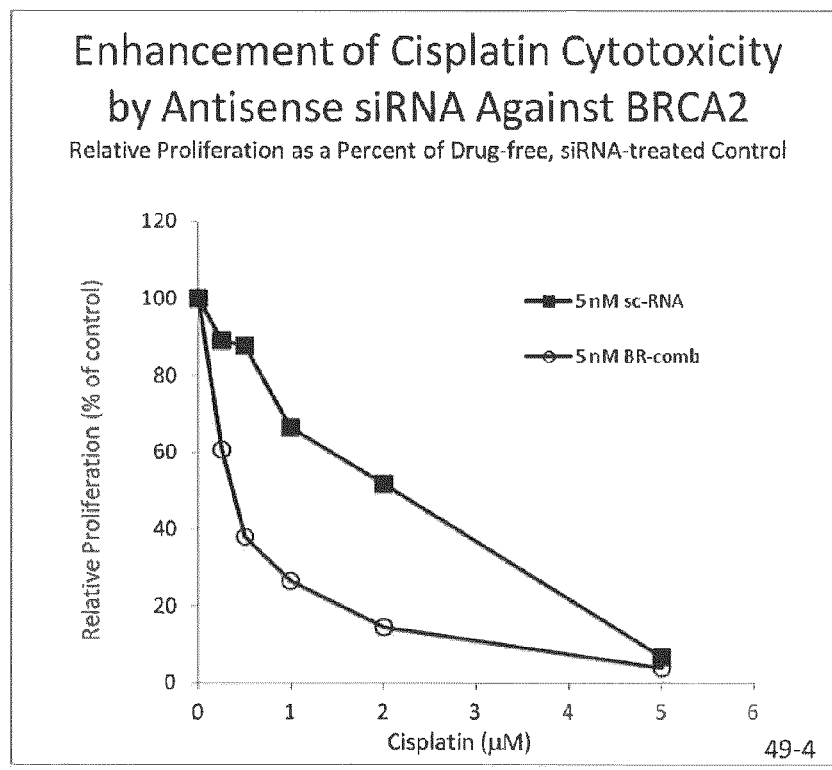
FIG. 19 illustrates enhancement of cisplatin cytotoxicity by antisense siRNA against BRCA2.

The results of this experiment are shown in FIG. 19, which shows that pretreatment of A549b cells with four anti-BRCA2 siRNAs enhanced the anti-proliferative effect of cisplatin.

Example 16: Effect of Anti-RAD51 siRNA on Proliferation of PANC-1 Pancreatic Carcinoma Cells This experiment examined the effect of four different siRNA molecules against RAD51 on proliferation of PANC-1 pancreatic carcinoma cells.

These experiments were carried out essentially as described in Example 2, after which one volume of medium was added, and cells were further incubated for 20 hours. siRNA-containing medium was removed and replaced with fresh medium. Cells were incubated for 4 days, at which time cell number was counted. Proliferation was calculated as a percent of controls.

Figure 20:
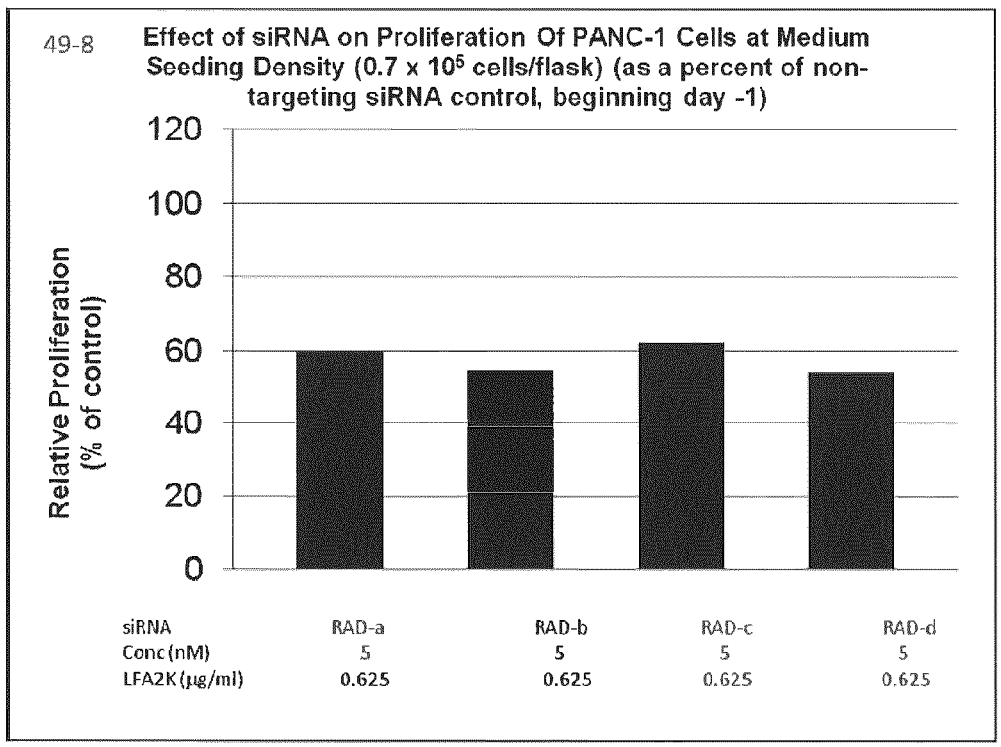
FIG. 20 illustrates that four different siRNA molecules against RAD51 inhibited proliferation of PANG-1 pancreatic carcinoma cells.

The results of this experiment are shown in FIG. 20, which shows that four different siRNA molecules against RAD51 inhibited proliferation of PANC-1 pancreatic carcinoma cells by 40 to 50% at 5 nM.

Example 17: Effect of Anti-RAD51 siRNA on Proliferation of A549B Cells

This experiment examined the effect of siRNA RADb molecules against RAD51 on proliferation of A549b cells.

These experiments were carried out essentially as described in Example 2, after which one volume of medium was added, and cells were further incubated for 20 hours. siRNA-containing medium was removed and replaced with fresh medium. Cells were incubated for 4 days, at which time cell number was counted. Proliferation was calculated as a percent of controls.

Figure 21:
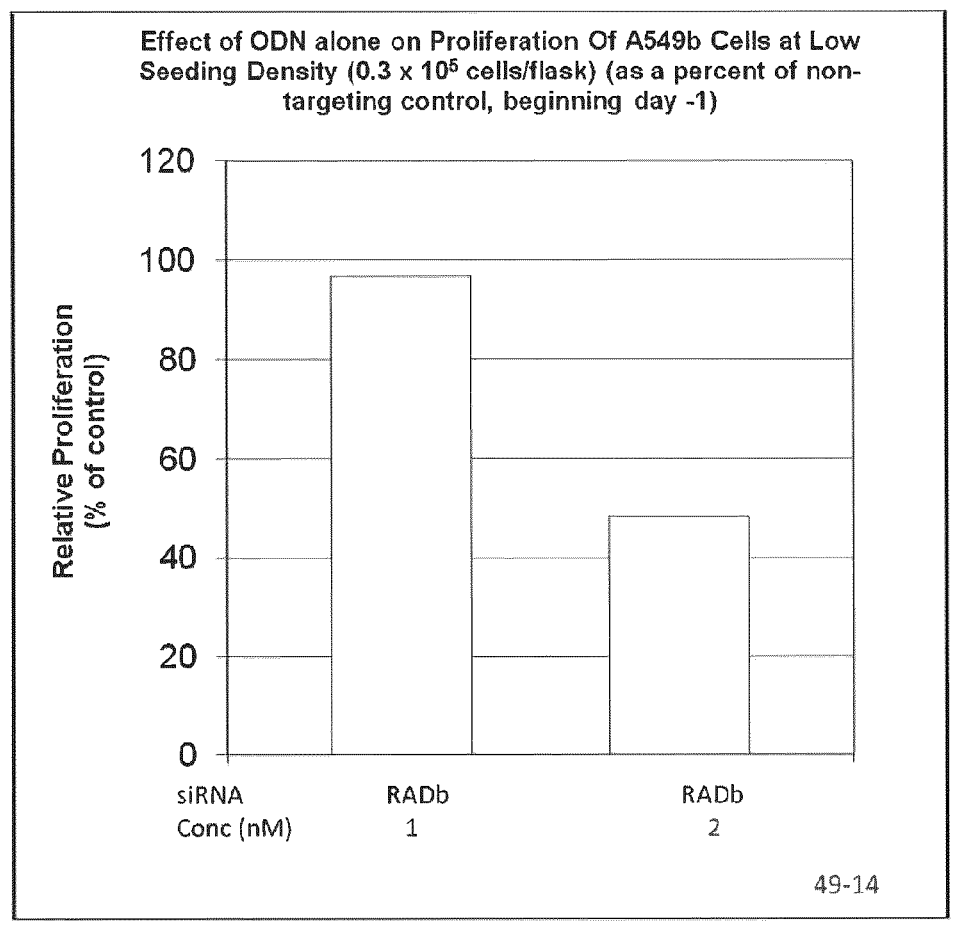
FIG. 21 illustrates that siRNA RADb against RAD51 inhibited proliferation of A549b cells by over 50% at 2 nM.

The results of this experiment are shown in FIG. 21, which shows that siRNA RADb against RAD51 inhibited proliferation of A549b cells by over 50% at 2 nM.

Example 18: Effect of Combined TS siRNA and BRCA2 siRNA on A549B Cell Sensitivity to Treatment with Cisplatin and 5FUdR This experiment examined the effect of combined TS siRNA and BRCA2 siRNA on A549b sensitivity to cisplatin and 5FUdR.

Figure 22:
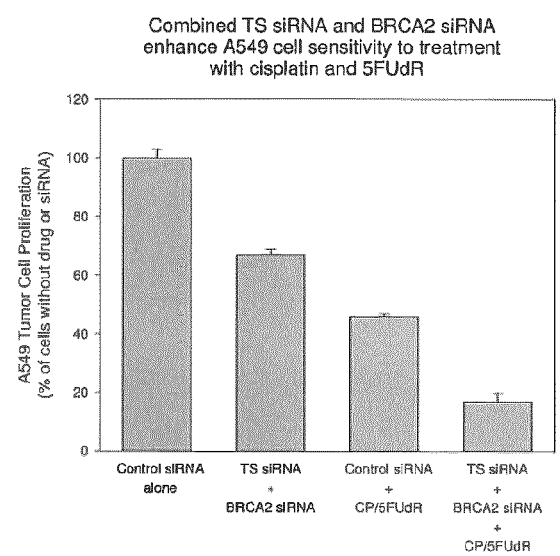
FIG. 22 illustrates combined TS siRNA and BRCA2 siRNA enhance A549b cell sensitivity to treatment with cisplatin and 5FUdR. All cell numbers are shown as a % of the number of cells treated with control siRNA alone±SD.

A549 cells were transfected with control non-targeting siRNA (20 nM) or TS siRNA (10 nM) and BRCA2 siRNA (10 nM). Cisplatin (4 µM) and 5FUdR (10 nM) or vehicle control was added 24 hours later. Cells were allowed to proliferate for 96 hours and then counted (Coulter counter). Cisplatin and 5FUdR treatment, or TS siRNA plus BRCA2 siRNA treatment, reduced proliferation. As shown in FIG. 22 combined treatment with both siRNAs and both drugs reduced proliferation further than treatment with siRNAs or drugs alone.

Example 19: Reciprocal Positive Selection for Weakness—Overcoming Olaparib Resistance Abstract:

Background:

Intra-tumor heterogeneity in human cancers makes resistance to therapy a mathematical certainty. The PARP-1 inhibitor olaparib is selectively lethal to cells deficient in homologous recombination repair (HRR), but cells with intact HRR that survive treatment contribute to eventual therapy failure. We hypothesized that combining BRCA2 and PARP-1 inhibition ("reciprocal positive selection for weakness") would avoid this drawback. HRR-proficient cells are preferentially sensitive to BRCA2 inhibition, while HRR-deficient cells are killed by olaparib. Combined inhibition of BRCA2 and PARP1 prevents selection based on HRR function in heterogeneous cancer cell populations and forestalls resistance.

Methods:

BRCA2 was inhibited with antisense oligonucleotides. Sensitization to olaparib was tested using counting-based proliferation assays. A co-culture model of cells with varying HRR-proficiency was used to evaluate acquired resistance. SKOV3-IP1 cells were injected into nude mice which were then treated with control or BRCA2 siRNA and/or olaparib.

Results:

BRCA2 downregulation overcame innate olaparib resistance in lung, ovarian and breast cancer cells but did not sensitize non-cancer cells to treatment. BRCA2 inhibition and olaparib treatment increased aneuploidy and the incidence of chromosomal translocations. In a mixed cell population heterogeneous for HRR-proficiency, olaparib monotherapy rapidly selected for HRR-proficient cells. Combined BRCA2 and olaparib treatment prevented selection based on HRR proficiency and inhibited the proliferation of the entire population. Treatment of tumor-bearing mice with BRCA2 siRNA and olaparib decreased the weight and number of tumors relative to either treatment alone.

Conclusion:

Combined BRCA2 and PARP-1 inhibition overcomes treatment resistance via reciprocal positive selection for weakness.

Introduction:

Tumor heterogeneity is common among human cancers and promotes therapeutic resistance [1, 2] by ensuring the presence of resistant cells at the start of treatment. This phenomenon has been observed in vitro [3] and modelled in silico using human clinical data [3, 4]. Single-nucleus genome sequencing of breast cancer samples has shown that no two cancer cells in a tumor are identical [5], highlighting the challenge to effective and long-term anti-cancer therapy.

Cytotoxic and targeted-therapies impose selective pressure on the diverse tumor ecosystem, promoting survival of cells with highest fitness. This is consistent with classical evolutionary theory [6] and leads to eventual therapeutic failure. It is necessary to design treatment regimens that select for treatment sensitivity (weakness), rather than positively selecting for resistant tumor cells. We propose that this can be achieved using an orchestrated combination therapy to simultaneously inhibit BRCA2 and PARP1.

PARP-1 inhibitors such as olaparib are selectively effective in tumors with homologous recombination repair (HRR) deficiency [7]. This occurs primarily due to the inability of HRR-deficient tumor cells to repair double-strand DNA breaks (DSBs) that result when PARP1 inhibition prevents resolution of single-strand breaks (SSBs) [8]. However, the selective killing of tumor cells with HRR defects, an attractive therapeutic goal for PARP inhibitors, ultimately contributes to reduced effectiveness. First, HRR-deficient tumors, against which PARP1 inhibitors are most useful, are present in only a subset of cancer patients [9]. Second, selective killing in a heterogeneous tumor population leads to outgrowth of resistant clones and therapy failure, a phenomenon already described for PARP-1 inhibitors [10].

Combining PARP1 inhibition with BRCA2 inhibition may be an avenue to prevent resistance via a mechanism we termed "reciprocal positive selection for weakness". In a heterogeneous tumor population, BRCA2 inhibition will select for cells with deficient HRR and render the population sensitive to PARP-1 inhibition. The reciprocal is also true: PARP-1 inhibition will select for HRR-proficient cells susceptible to BRCA2 inhibition (FIG. 31). We hypothesize that simultaneous inhibition of both BRCA2 and PARP-1 will prevent the outgrowth of resistant cells based on HRR proficiency and promote tumor responsiveness to treatment.

In this study, we show that BRCA2 inhibition overcame innate olaparib resistance in several tumor cell lines, but did not sensitize non-cancerous lines to PARP-1 inhibition. Application of reciprocal positive selection for weakness by combining BRCA2 inhibition and olaparib treatment in a tumor cell population heterogeneous for HRR-proficiency prevented the outgrowth of resistant clones. Combined inhibition of BRCA2 and PARP1 delayed the growth of ovarian cancer tumors in vivo. This work provides rationale for combining BRCA2 inhibition and olaparib treatment to achieve reciprocal positive selection for weakness to prevent therapy resistance. It also reveals a strategy to extend clinical application of olaparib (currently used primarily in BRCA1/2-mutated ovarian cancers [11]) to BRCA-positive tumors.

Selected Methods:

Cell Proliferation Assay

Four hours post-transfection, cells were seeded into 6 well dishes in appropriate experimental groups. Twenty-four hours post transfection, cells were treated with olaparib (Selleckchem) at three concentrations. Ninety-six hours post transfection, cells were collected and counted (Coulter Particle Counter). Proliferation was determined based on initial cell density and calculated as a percentage of ASO+vehicle treated cells.

In Vivo Tumor Model

Eight to twelve week old female athymic nude mice were purchased from the National Cancer Institute (Frederick, Md.). All mouse studies were approved by the MD Anderson Cancer Center Institutional Animal Care and Use Committee. SKOV3ip1 ovarian cancer cells ($1.0 \times 10^6$) were trypsinized, suspended in 200 µl of Hanks balanced salt solution (HBSS; Gibco, Carlsbad, Calif.) and injected into the intraperitoneal cavity (i.p.). Seven days after cell injection, mice were randomly divided into 4 groups: 1) Control siRNA/DOPC 2) BRCA2 siRNA/DOPC 3) Control siRNA/DOPC+olaparib 4) BRCA2 siRNA/DOPC+olaparib (n=10 mice per group). siRNA/DOPC nanoparticles were injected twice weekly (150 µg/kg body weight) and olaparib (5 mg/kg body weight; 5 days a week) (i.p.). Mice were monitored daily for adverse effects of therapy and were sacrificed when they became moribund (6-7 weeks after cell injection). At the time of sacrifice, mouse and tumor weight was recorded. Tumor tissue was harvested and either fixed in formalin for paraffin embedding, or frozen in optimum cutting temperature medium (OCT; Miles, Inc., Elkhart, Ind.) to prepare frozen slides, or snap-frozen in liquid nitrogen for lysate preparation. The individuals who performed the necropsies, tumor collections, and tissue processing were blinded to the treatment group assignments.

Results

BRCA2 Inhibition Overcomes Innate Olaparib Resistance in Three Lung Cancer Cell Lines Olaparib has limited efficacy in cancer cells with intact HRR [12]. The majority of lung tumors do not exhibit mutations in BRCA1/2 genes (BRCA1/2 is mutated in 1.8%-11.2% of cases depending on the data set and tumor type) [13]. Thus, olaparib may have little utility in lung cancer treatment on its own. To determine whether BRCA2 inhibition could overcome innate olaparib resistance, we tested control or BRCA2 ASO treatment with olaparib in A549 lung adenocarcinoma and H2052 and 211H mesothelioma cell lines, all BRCA2-proficient.

Figure 23:
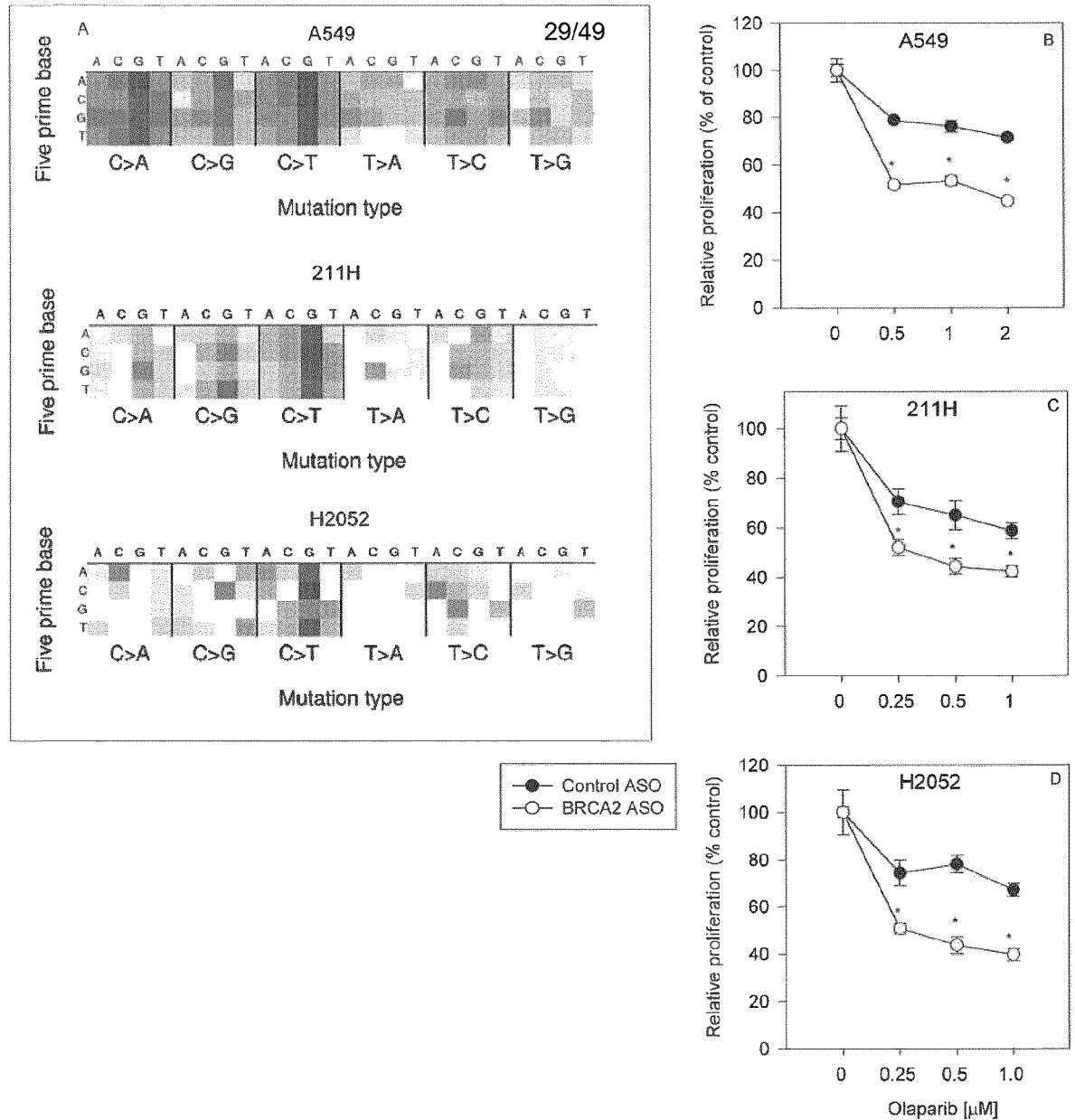
FIG. 23 illustrates that BRCA2 inhibition overcomes innate olaparib resistance in three cancer cell lines. A mutation heat map for each cell line was generated using the COSMIC CCLE database interface (A). A549 (lung cancer) (B), 211H (mesothelioma) (C), and H2052 (mesothelioma) (D) cells were transfected with control ASO (•) or BRCA2 ASO (○) and then treated with three different concentrations of olaparib as described in *Supplemental Materials and Methods*. Proliferation was determined by cell counting 96 hours post-transfection (*p<0.05). Means±SD from representative experiments are shown. All experiments were repeated at least once.

All three cell lines harbor mutations (513 coding+616 non-coding mutations in A549 cells; 402 coding+509 non-coding mutations in 211H cells; and 80 coding+76 non-coding mutations in H2052 cells)(FIG. 23A), suggesting heterogeneity in each population. BRCA2 downregulation increased olaparib sensitivity by as much as 34.5%±2.8%, 31.9%±8.5%, and 44.1%±7.8% ($p<0.05$) in A549, 211H, and H2052 cells, respectively (FIG. 23B-D). BRCA2 ASO treatment sensitized all three lung cancer cell lines to olaparib across the entire range of drug concentrations regardless of mutational signature and load, suggesting that BRCA2 inhibition may render lung tumors with disparate backgrounds sensitive to PARP inhibition.

BRCA2 Inhibition Sensitizes Ovarian and Breast Cancer Cells to Olaparib Treatment Olaparib is approved by the FDA for treatment of BRCA1/2-mutated ovarian cancers [11]. However, only a fraction of ovarian tumors exhibit BRCA1/2 mutations [13] and most ovarian cancer patients are not eligible for olaparib treatment. Overcoming innate olaparib resistance in ovarian cancer cells with WT BRCA1/2 is potentially valuable clinically.

Figure 24:
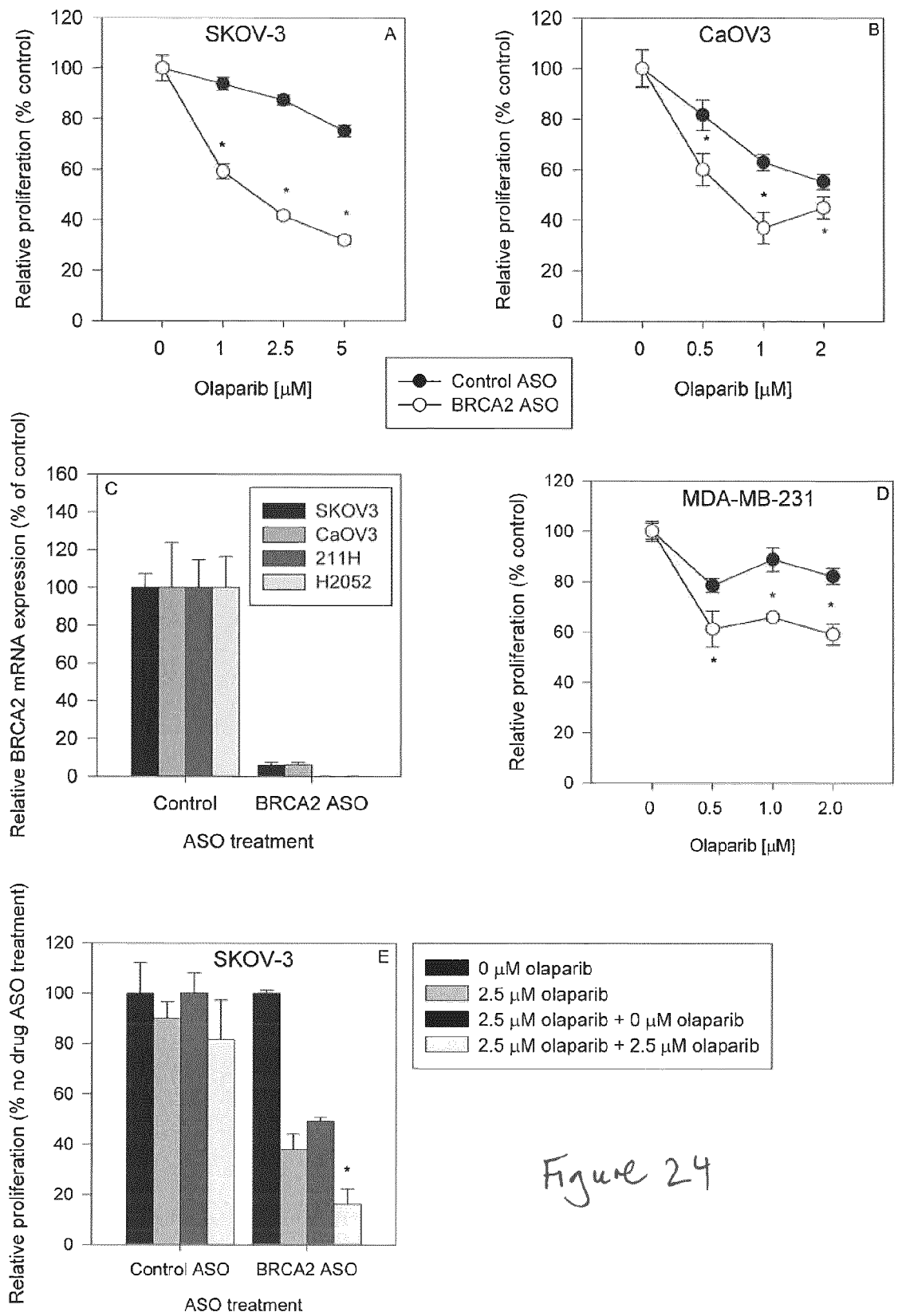
FIG. 24 illustrates that BRCA2 inhibition sensitizes ovarian cancer and breast cancer cell lines to olaparib treatment. SKOV-3 (A) and CaOV3 (B) cells were transfected with control ASO (•) or BRCA2 ASO (○) and then treated with three different concentrations of olaparib. Proliferation was determined by cell counting 96 hours post-transfection (*p<0.05). C: BRCA2 mRNA levels were measured by qPCR 24 hours following BRCA2 ASO transfection in SKOV-3, CaOV3, 211 H and H2052 cell lines.

We tested whether BRCA2 downregulation could sensitize two different ovarian cancer cell lines to olaparib treatment. BRCA2 ASO treatment sensitized SKOV-3 cells to PARP1 inhibition by as much as 52.3%±2.7% (p<0.05) (FIG. 24A) and CaOv3 cells by 41.3%±9.9% (p<0.05)(FIG. 2B). The amount of antisense-mediated BRCA2 mRNA knockdown was greater than 90% in both cell lines, similar to the amount of BRCA2 reduction in H2052 and 211H mesothelioma cells (FIG. 24C).

Triple-negative (estrogen receptor (ER), progesterone receptor (PR), and Her2/neu [5]) MDA-MB-231 cells were rendered as much as 28.0%±5.1% (p<0.05) more sensitive to olaparib compared to cell treated with control ASO (FIG. 42D). Therapy options for triple-negative breast cancer are limited [14] and decreasing innate olaparib resistance by BRCA2 downregulation could reveal a new path to more effective treatment.

To determine whether cells that survived the initial BRCA2 ASO and olaparib treatment remain sensitive to subsequent treatment, we treated the same cells with BRCA2 ASO and olaparib a second time. Single BRCA2 ASO+olaparib treatment hindered the proliferation of cells which were re-seeded without any additional olaparib treatment. In addition, a second round of BRCA2 ASO+olaparib treatment decreased SKOV-3 cell proliferation by 67.0%±12.4% (p<0.05) compared to cells which did not receive this second olaparib treatment (FIG. 24E). This suggests that cells which survive the first round of BRCA2 ASO+olaparib treatment are still sensitive to a second treatment that decreases their proliferation.

BRCA2 Inhibition does not Sensitize Non-Cancerous Cells to Olaparib Treatment

An important question when inhibiting BRCA2 in the context of olaparib treatment is whether non-cancer cells are affected to the same degree as tumor cells. Non-cancer, BRCA2-positive HK-2 kidney proximal tubule epithelial cells were treated with either control ASO or BRCA2 ASO followed by olaparib. BRCA2 inhibition did not sensitize HK-2 cells to olaparib at the tested concentrations (FIG. 25A). BRCA2 mRNA downregulation was confirmed by qPCR to ensure that lack of sensitization was not due to inadequate transfection (FIG. 25B). The experiment was repeated using non-cancer CCD-841 colon epithelial cells and BRCA2 ASO treatment did not increase the potency of olaparib at any tested concentration (FIG. 25C).

BRCA2 ASO and Olaparib Treatment Induces Chromosome Aberrations in Ovarian Cancer Cells Failure of the spindle assembly checkpoint (SAC) results in abnormal chromosomal segregation and can lead to fatal chromosome gain or loss in daughter cells [15]. Both BRCA2 and PARP1 support SAC in mitotic cells [16] and we hypothesized that the decreased proliferation following inhibition of both targets may be due to perturbation of SAC.

We investigated the effect of BRCA2 ASO and olaparib treatment on bulk chromosome number using metaphase spreads of SKOV-3 and MDA-MB-231 cells. Twenty-four hours following olaparib or vehicle treatment, we identified a significant increase in the variance of the chromosome number in cells treated with BRCA2 ASO+olaparib (FIGS. 26A&B). This is consistent with the hypothesis that combined BRCA2 and PARP1 inhibition negatively affects the SAC and allows for the mis-segregation of chromosomes, leading to altered aneuploidy in daughter cells.

To determine whether BRCA2 ASO and olaparib treatment had an effect on genome stability we used whole chromosome FISH probes to label chromosomes X, 3, and 16, and quantify the incidence of random translocations following treatment. Combined BRCA2 ASO+olaparib treatment led to 1.18 mean translocations per metaphase, compared to 0.1, 0.25 and 0.14 for other treatments (*p<0.05) (FIG. 26C).

Combined BRCA2 ASO and Olaparib Treatment can Prevent Resistance in a Mixed Cell Line Model with Varying Degrees of HRR Human tumors exhibit a high degree of heterogeneity [1, 4, 17] which can lead to olaparib resistance [10]. Resistance can occur through a variety of mechanisms [18] including reversion to HRR-proficiency in tumors that were predominantly HRR-deficient prior to treatment [10, 19]. Due to the functional linkage between BRCA2 and PARP-1, we hypothesized that combined BRCA2 ASO and PARP inhibition would prevent reversion to HRR proficiency and the appearance of olaparib resistance.

To test this hypothesis, we used three human tumor cell lines with varying degrees of HRR proficiency: SKOV-3 (BRCA2 WT [20]), MCF-7 (HRR deficient [21]), and CAPAN-1 (BRCA2 mutant [20]).

When these three cell lines were treated with BRCA2 ASO (20 nM) simultaneously, the proliferation of HRR-proficient SKOV-3 cells was decreased by 35%±10% (p<0.05) (FIG. 27A). Thus, BRCA2 knockdown alone effectively reduced growth of HRR-proficient tumor cells. BRCA2 knockdown in HRR-deficient MCF-7 and CAPAN-1 cells, in contrast, had no negative effect on proliferation. These data support the hypothesis that BRCA2 downregulation in a mixed population of HRR-proficient and HRR-deficient cells would lead to an increased fraction of HRR-deficient, BRCA2 ASO-resistant cells (FIG. 27A). When the cell fraction of a theoretical mixed population was calculated on the basis of relative proliferation after treatment with BRCA2 ASO, HRR-deficient MCF-7 and CAPAN-1 cells increased in proportion from a total of 66% to 77% relative to SKOV-3 cells (FIG. 27B). Thus, BRCA2 downregulation can select for HRR-deficient cells.

In contrast, a single treatment of each of the 3 cell lines with olaparib treatment decreased the proliferation of HRR-deficient MCF-7 and CAPAN-1 cells by 39%±6.8% and 94%±4.6% (p<0.05), respectively, but had no effect on SKOV-3 proliferation (FIG. 27C). Therefore, the fraction of HRR-proficient SKOV-3 cells in a theoretical mixed population after olaparib treatment increased from 33% to 61%. Thus, a single olaparib treatment can select for HRR-proficient cells, which is the reciprocal of the effect of BRCA2 ASO.

HRR-proficient SKOV-3 cells are resistant to olaparib relative to HRR-deficient MCF-7 cells (FIG. 28A). Combined treatment with BRCA2 ASO and olaparib abolished that relative resistance and led to a decrease in proliferation in both cell lines of 40% (p<0.05) (FIG. 6B). This suggests that simultaneous inhibition of BRCA2 and PARP-1 in heterogeneous tumor populations can prevent selection events and forestall emergence of treatment-resistant clones.

Combined BRCA2 ASO and Olaparib Treatment can Prevent the Outgrowth of Resistant Clones in a Co-Culture Model of BRCA2 Heterogeneity To evaluate the effects of BRCA2 ASO and olaparib on population dynamics and resistance to treatment over time, we devised a co-culture model of SKOV-3 ovarian cancer cells stably expressing either shRNA targeting BRCA2 or control shRNA. This emulated a tumor population with different proportions of cells of varying HRR-proficiency.

To mimic a heterogeneous tumor cell population that is predominantly HRR-deficient, we co-cultured SKOV-$3^{shBRCA2}$ (low BRCA2) and SKOV-$3^{shcontrol}$ (high BRCA2) in a 3:1 ratio. The mixed cell population, along with unmixed SKOV-3$^{shBRCA2}$ and SKOV-3$^{shcontrol}$ populations, was treated with olaparib (1° Olaparib), then counted, re-seeded and treated with olaparib a second time (2° Olaparib) (FIG. 32). The mixed cell population, though sensitive to initial treatment with olaparib (Bar 9 vs 10), was completely unresponsive to a second treatment (Bar 11 vs 12) (FIG. 29A). The unmixed SKOV-3$^{shBRCA2}$ population remained sensitive to olaparib even after two treatments (Bar 7 vs 8)(FIG. 29A). This suggests that 1° olaparib treatment of the mixed cell population selected for HRR-proficient cells and allowed them to outgrow HRR-deficient cells.

To determine if combined BRCA2 ASO and olaparib treatment could prevent the development of resistance among mixed SKOV-3$^{shBRCA2}$ and SKOV-3$^{shControl}$ cells, the mixed and unmixed cells were treated with either control ASO or BRCA2 ASO, in the presence or absence of drug treatment. BRCA2 ASO treatment sensitized the mixed cell population to olaparib (Bar 11 and 12), and the proliferation level of the mixed population following BRCA2 ASO and olaparib treatment was similar to that of the SKOV3$^{shBRCA2}$ cells treated similarly (Bar 7 and 8)(FIG. 29B).

When mixed and unmixed SKOV-3 populations treated with olaparib and either control ASO or BRCA2 ASO were re-seeded without any further treatment, the mixed cell population that had received BRCA2 ASO+olaparib was unable to proliferate (FIG. 29C). This suggests that simultaneous inhibition of both BRCA2 and PARP1 can prevent the outgrowth of resistant cells in a tumor population with HHR heterogeneity.

Combined Inhibition of BRCA2 and PARP1 Prevents Ovarian Tumor Growth In Vivo

We determined whether combined BRCA2 and PARP1 inhibition could prevent or delay growth of ovarian tumors in vivo. Female athymic nude mice were injected with SKOV3-IP1 cells i.p and treated 7 days later with control siRNA or BRCA2 siRNA in the presence or absence of olaparib. Following 7 weeks of treatment, mice were weighed (FIG. 8A), euthanized, and dissected to determine the number and combined weight of tumor nodules in the peritoneal cavity. BRCA2 siRNA+olaparib treatment decreased both the number (FIG. 8B) and weight (FIG. 8C) of tumors relative to BRCA2 siRNA or olaparib treatment alone (p<0.05), suggesting that combing BRCA2 reduction with PARP1 inhibition may be useful therapeutically to prevent tumor growth and metastasis.

DISCUSSION

The PARP1 inhibitor olaparib is approved for treatment of BRCA1/2-mutated ovarian tumors. However, this represents only a subset of cancer patients [11] and resistance can occur even in this population [19]. We tested a BRCA2 ASO in combination with olaparib to determine whether the combination could: 1) overcome innate resistance and increase the potential usefulness of olaparib by rendering HRR-proficient, BRCA2-positive tumors sensitive to the drug, and 2) prevent acquired resistance in cell populations with mixed HRR-proficiency.

We show, using human lung, ovarian, and breast cancer cell lines, that BRCA2 ASO treatment can overcome innate resistance to olaparib in these cell lines. None are reported to harbour BRCA2 or BRCA1 mutations (COSMIC CCLE database) and, with functional BRCA2 capable of mediating HRR, are relatively resistant to the therapeutic effects of PARP1/2 inhibition by olaparib. Therefore, BRCA2 ASO treatment has the potential to render a high proportion of tumor cells sensitive to olaparib treatment, which may extend the usefulness and applicability of this drug in the clinic.

The fact that olaparib primarily targets HRR-deficient tumors is also a potential problem due to positive selection for resistant clones in a heterogeneous tumor ecosystem. Most tumors exhibit complex polyclonal variability and data from single nucleus sequencing of breast tumors suggests that no two tumor cells are identical [5]. This renders resistance to targeted therapy and chemotherapy inevitable mathematically [3], and very common biologically [1, 2]. Several olaparib resistance mechanisms have already been described, including the outgrowth of tumors with re-activation mutations in BRCA2 which render olaparib ineffective [18]. In addition, BRCA1-mutated tumors cells with a concomitant mutation in 53BP1 are no longer HRR-deficient and also exhibit resistance to PARP1 inhibition [22]. It therefore appears that olaparib treatment will fail at high frequency without any corresponding positive selection pressure for cells with HRR-deficiency.

Combining BRCA2 inhibition with PARP1 inhibition can achieve a state where each individual treatment positively selects for cells with unique susceptibility to the other treatment, thus preventing or delaying resistance: this is the essence of the concept which we have termed reciprocal positive selection for weakness. The data from our mixed cell experiments suggests that simultaneous inhibition of BRCA2 and olaparib treatment has the ability to limit the proliferation of tumor cells heterogeneous for HRR-proficiency, thus preventing positive selection of resistant cells based on ability to repair DNA.

An important consideration is whether it is possible to develop resistance to simultaneous BRCA2 and PARP1 inhibition (either through a primary mechanism related to HRR, or a secondary mechanism unrelated to HRR proficiency). It may be possible to address this question using a barcoded shRNA library to downregulate an assortment of genes in the context of BRCA2 deficiency and olaparib treatment. The shRNA barcode could be used to determine which gene or genes were down-regulated in any surviving cells. This experiment would divulge whether resistance to combined BRCA2 and PARP1 inhibition is possible, and if so, identify a subset of targets for further study and development of strategies to prevent or overcome this potential resistance mechanism.

Our in vivo data suggest that it is possible to combine BRCA2 inhibition and olaparib treatment for therapeutic benefit. The mice which received combination treatment exhibited the fewest tumor nodules, and the lowest tumor weight relative to control and each of the single treatments. In particular, the i.p model recapitulates several hallmarks of later stage ovarian cancer, and is a model to explore the potential of therapy to prevent the establishment of metastatic lesions at secondary sites in the peritoneal cavity [23]. We propose, therefore, that combined BRCA2 downregulation and olaparib treatment can be used following surgical resection of primary tumor to prevent spread and growth at secondary sites.

REFERENCES

1. Burrell, R. A. and C. Swanton, *Tumour heterogeneity and the evolution of polyclonal drug resistance.* Mol Oncol, 2014. 8(6): p. 1095-111.
2. Kessler, D. A., R. H. Austin, and H. Levine, *Resistance to chemotherapy: patient variability and cellular heterogeneity.* Cancer Res, 2014. 74(17): p. 4663-70.

3. Bozic, I., et al., *Evolutionary dynamics of cancer in response to targeted combination therapy*. Elife, 2013. 2: p. e00747.
4. Bhang, H. E., et al., *Studying clonal dynamics in response to cancer therapy using high-complexity barcoding*. Nat Med, 2015. 21(5): p. 440-8.
5. Wang, Y., et al., *Clonal evolution in breast cancer revealed by single nucleus genome sequencing*. Nature, 2014. 512(7513): p. 155-60.
6. Gillies, R. J., D. Verduzco, and R. A. Gatenby, *Evolutionary dynamics of carcinogenesis and why targeted therapy does not work*. Nat Rev Cancer, 2012. 12(7): p. 487-93.
7. Evers, B., et al., *A high-throughput pharmaceutical screen identifies compounds with specific toxicity against BRCA2-deficient tumors*. Clin Cancer Res, 2010. 16(1): p. 99-108.
8. Bryant, H. E., et al., *Specific killing of BRCA2-deficient tumours with inhibitors of poly(ADP-ribose) polymerase*. Nature, 2005. 434(7035): p. 913-7.
9. Farmer, H., et al., *Targeting the DNA repair defect in BRCA mutant cells as a therapeutic strategy*. Nature, 2005. 434(7035): p. 917-21.
10. Lord, C. J. and A. Ashworth, *Mechanisms of resistance to therapies targeting BRCA-mutant cancers*. Nat Med, 2013. 19(11): p. 1381-8.
11. Kim, G., et al., *FDA Approval Summary: Olaparib Monotherapy in Patients with Deleterious Germline BRCA-Mutated Advanced Ovarian Cancer Treated with Three or More Lines of Chemotherapy*. Clin Cancer Res, 2015.
12. Villanueva, T., *Expanding the horizons of PARP inhibitors*. Nat Rev Cancer, 2010. 10(12): p. 814.
13. Gao, J., et al., *Integrative analysis of complex cancer genomics and clinical profiles using the cBioPortal*. Sci Signal, 2013. 6(269): p. pl1.
14. Lehmann, B. D. and J. A. Pietenpol, *Identification and use of biomarkers in treatment strategies for triple-negative breast cancer subtypes*. J Pathol, 2014. 232(2): p. 142-50.
15. Kops, G. J., D. R. Foltz, and D. W. Cleveland, *Lethality to human cancer cells through massive chromosome loss by inhibition of the mitotic checkpoint*. Proc Natl Acad Sci USA, 2004. 101(23): p. 8699-704.
16. Choi, E., et al., *BRCA2 fine-tunes the spindle assembly checkpoint through reinforcement of BubR1 acetylation*. Dev Cell, 2012. 22(2): p. 295-308.
17. Swanton, C., R. A. Burrell, and P. A. Futreal, *Breast cancer genome heterogeneity: a challenge to personalised medicine?* Breast Cancer Res, 2011. 13(1): p. 104.
18. Bouwman, P. and J. Jonkers, *Molecular pathways: how can BRCA-mutated tumors become resistant to PARP inhibitors?* Clin Cancer Res, 2014. 20(3): p. 540-7.
19. Ashworth, A., *Drug resistance caused by reversion mutation*. Cancer Res, 2008. 68(24): p. 10021-3.
20. Forbes, S. A., et al., *COSMIC: exploring the world's knowledge of somatic mutations in human cancer*. Nucleic Acids Res, 2015. 43(Database issue): p. D805-11.
21. Peng, G., et al., *Genome-wide transcriptome profiling of homologous recombination DNA repair*. Nat Commun, 2014. 5: p. 3361.
22. Jaspers, J. E., et al., *Loss of 53BP1 causes PARP inhibitor resistance in Brca1-mutated mouse mammary tumors*. Cancer Discov, 2013. 3(1): p. 68-81.
23. Shaw, T. J., et al., *Characterization of intraperitoneal, orthotopic, and metastatic xenograft models of human ovarian cancer*. Mol Ther, 2004. 10(6): p. 1032-42.
1. Abbott D W, Freeman M L, Holt J T. Double-strand break repair deficiency and radiation sensitivity in BRCA2 mutant cancer cells. J Natl Cancer Inst 90: 978-985, 1998.
2. Fong P C, Boss D S, Yap T A, Tutt A, Wu P, Mergui-Roelvink M, Mortimer P, Swaisland H, Lau A, O'Connor M J, Ashworth A, Carmichael J, Kaye S B, Schellens J H, de Bono J S. Inhibition of poly(ADP-ribose) polymerase in tumours from BRCA mutation carriers. N Engl J Med 361: 123-134, 2009.
3. Ferguson P J, Kurowska E, Freeman D J, Chambers A F, and Koropatnick D J: A flavonoid fraction from cranberry extract inhibits proliferation of human tumour cell lines. J Nutr 134, 1529-1535, 2004.
4. Ferguson P J, Collins O, Dean N M, DeMoor J, Chen S-L, Vincent M D, and Koropatnick J: Antisense down-regulation of thymidylate synthase to suppress growth and enhance cytotoxicity of 5-FUdR, 5-F U, and Tomudex in HeLa cells. Brit J Pharmacol, 127: 1777-1786, 1999.
5. Ferguson, P. J., DeMoor, J. M., Vincent, M. D., and Koropatnick, J. Antisense-induced down-regulation of thymidylate synthase and enhanced cytotoxicity of 5-FUdR in 5-FUdR-resistant HeLa cells. Br. J. Pharmacol., 134: 1437-1446, 2001.
6. Abbott D W, Freeman M L, Holt J T. Double-strand break repair deficiency and radiation sensitivity in BRCA2 mutant cancer cells. J Natl Cancer Inst 90: 978-985, 1998.
7. Turner N C, Lord C J, lorns E, Brough R, Swift S, Elliott R, Rayter S, Tutt A N, Ashworth A. A synthetic lethal siRNA screen identifying genes mediating sensitivity to a PARP inhibitor. EMBO J 27: 1368-1377, 2008.
8. Gudmundsdottir K, Ashworth A. The roles of BRCA1 and BRCA2 and associated proteins in themaintenance of genomic stability. Oncogene 25: 5864-5874, 2006.
9. Moynahan M E, Jasin M. Mitotic homologous recombination maintains genomic stability andsuppresses tumourigenesis. Nature Reviews Molec Cell Biol, 11: 196-207, 2010
10. Zhang F, Fan Q, Ren K, Andreassen P R. PALB2 functionally connects the breast cancer susceptibility proteins BRCA1 and BRCA2. Mol *Cancer* Res 7: 1110-1118, 2009.
11. Wang J, Bian C, Li J, Couch F J, Wu K, Zhao R C. Poly9ADP-ribose) polymerase-1 down-regulates BRCA2 expression through the BRCA2 promoter. J Biol Chem 283: 36249-36256, 2008.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

TABLE 3

Sequences

| SEQ ID NO: | SEQUENCES: | NOTES: |
|---|---|---|
| 1 | 5'-guaucuCTTGACGTuccuua-3' | BR1 gapmer - lowercase letters represent 2'-O-methyl RNA; phosphorothioate throughout the entire length of the OLIGO |
| 2 | 5'-uaccagCGAGCAGGccgagu -3' | BR2 gapmer - lowercase letters represent 2'-O-methyl RNA; phosphorothioate throughout the entire length of the OLIGO |
| 3 | 5'-ugcccgATACACAAacgcug -3' | BR3 gapmer - lowercase letters represent 2'-O-methyl RNA; phosphorothioate throughout the entire length of the OLIGO |
| 4 | 5'-CAGCGTTTGTGTATCGGGCA-3' | BRCA2 Antisense |
| 5 | 5'- TTGGATCCAATAGGCAT-3' | BRCA2 Antisense |
| 6 | 5'-TACGTACTCCAGAACATTTAA-3' | BRCA2 Antisense |
| 7 | 5'-TTGGAGGAATATCGTAGGTAA-3' | BRCA2 Antisense |
| 8 | 5'-CAGGACACAATTACAACTAAA-3' | BRCA2 Antisense |
| 9 | 5'-UAAAUAGCAAGUCCGUUUC-3' | BRCA2 siRNA "A" |
| 10 | 5'-UAAUGAAGCAUCUGAUACC-3' | BRCA2 siRNA "B" |
| 11 | 5'-UAUUAAACCUGCAUUCUUC-3' | BRCA2 siRNA "C" |
| 12 | 5'-GUAUCUCUUGACGUUCCUUA-3' | BRCA2 siRNA "D" |
| 13 | 5'-GTATCTCTTGACGTTCCTTA-3' | BR1 DNA |
| 14 | 5'-TACCAGCGAGCAGGCCGAGT -3' | BR2 DNA |
| 15 | 5'-TGCCCGATACACAAACGCTG -3' | BR3 DNA |
| 16 | 5'- GCCAGTGGCAACATCCTTAA-3' | OLIGO83 |
| 17 | 5'-guaucuCTTGACGTuccuua-3' | BR1 modified (lowercase letters represent 2'-O-methyl RNA) |
| 18 | 5'-UAAGGAACGUCAAGAGAUAC-3' | BR1 target |
| 19 | 5'-ACUCGGCCUGCUCGCUGGUA-3' | BR2 target |
| 20 | 5'-uaccagCGAGCAGGccgagu -3' | BR2 modified (lowercase letters represent 2'-O-methyl RNA) |
| 21 | 5'-CAGCGUUUGUGUAUCGGGCA-3' | BR3 target |
| 22 | 5'-ugcccgATACACAAacgcug -3' | BR3 modified (lowercase letters represent 2'-O-methyl RNA) |
| 23 | 5'-augcgcCAACGGTTccuaaa-3' | OLIGO32 (gapmer control) |
| 24 | 5'-ggagugCGTGAGTCgaugua-3' | OLIGO491S (gapmer control) |
| 25 | 5'-gccaguGGCAACATccuaaa-3' | OLIGO83 (lowercase letters represent 2'-O-methyl RNA) |
| 26 | 5'-CUGCAUCUGCAUUGCCAUUA-3' | prior art RAD51 target |
| 27 | 5'-GGCUUCACUAAUUCC-3' | prior art RAD51 target |
| 28 | 5'-GUAAUGGCAAUGCAGAUGC-3' | prior art RAD51 target |
| 29 | 5'-GAAUGGGUCUGCACAGAUUC-3' | RAD51 target |
| 30 | 5'-gaaucuGTGCAGACccauuc-3' | RAD51 antisense gapmer (lowercase letters represent 2'-O-methyl RNA) |
| 31 | 5'-GCAAGCCAGCTGAGGGCACA-3' | DNA-PK antisense |
| 32 | 5'-GGGCATTCCAAGGCTTCCCCA-3' | DNA-PK antisense |
| 33 | 5'-GGGCTCCCATCCTTCCCAGG-3' | DNA-PK antisense |
| 34 | 5'-AGGGGCCTTCTCATGACCCAGG-3' | DNA-PK antisense |
| 35 | 5'-ACTGCTGGATTGGCACCTGCT-3' | DNA-PK antisense |
| 36 | 5'-TGGGGTCTGTTGCCTGGTCC-3' | DNA-PK antisense |

TABLE 3-continued

Sequences

| SEQ ID NO: | SEQUENCES: | NOTES: |
|---|---|---|
| 37 | 5'-AAUUCUUCACAUCGUUGG-3' | siRNA against RAD51 "A" |
| 38 | 5'-UUAUCCAGGACAUCACUGC-3' | siRNA against RAD51 "B" |
| 39 | 5'-UGAGCUACCACCUGAUUAG-3' | siRNA against RAD51 "C" |
| 40 | 5'-UGAUGCAUGGGCGAUGAUA-3' | siRNA against RAD51 "D" |
| 41 | 5'-GUAUCUCUUGACGUUCCUUA-3' | BR1 RNA |
| 42 | 5'-UACCAGCGAGCAGGCCGAGU -3' | BR2 RNA |
| 43 | 5'-UGCCCGAUACACAAACGCUG -3' | BR3 RNA |
| 44 | 5'- GAATCTGTGCAGACCCATTC - 3' | RAD51 antisense |
| 45 | 5'- gaaucuGTGCAGACCcauuc - 3' | RAD51 gapmer - lowercase letters represent 2'-O-methyl RNA; phosphorothioate throughout the entire length of the OLIGO |
| 46 | 5' - CCGATTACCTGTGTACCCT -3' | Target for anti-BRCA2 siRNA |

We claim:

1. A method of treating cancer in a subject comprising administering to the subject an effective amount of an antisense based therapy comprising a sequence complementary to an mRNA encoding BRCA2 and a PARP-1 inhibitor; wherein the PARP-1 inhibitor is olaparib and the cancer has innate olaparib resistance.

2. The method of claim 1, wherein the antisense based therapy is an antisense oligonucleotide or a siRNA.

3. The method according to claim 1, wherein the antisense oligonucleotide has a length between about 7 and about 100 nucleotides, between about 12 and about 50 nucleotides, between about 12 and 35 nucleotides or between about 12 and 30 nucleotides.

4. The method according to claim 1, wherein the antisense based therapy comprises one or more phosphorothioate bonds.

5. The method according to claim 1, wherein the antisense based therapy comprises one or more 2'-O-methyl modified nucleotides.

6. The method according to claims 1, wherein the antisense based therapy comprises one or more 2'-O-methoxyethyl (2'-MOE) modified nucleotides.

7. The method according to claim 1, wherein the cancer is a solid tumour.

8. The method according to claim 7, wherein the cancer is lung cancer, colorectal cancer, gastric cancer, esophageal cancer, breast cancer, ovarian cancer, head and neck cancer, mesothelioma or prostate cancer.

9. A method of treating cancer in a subject, the method comprising administering to the subject an effective amount of an antisense based therapy comprising a sequence complementary to an mRNA encoding BRCA2 and a PARP-1 inhibitor; wherein the cancer has acquired resistance to the PARP1 inhibitor.

10. The method of claim 9, wherein the PARP1 inhibitor is olaparib.

11. The method of claim 9, wherein the antisense based therapy is an antisense oligonucleotide or a siRNA.

12. The method according to claim 9, wherein the antisense oligonucleotide has a length between about 7 and about 100 nucleotides, between about 12 and about 50 nucleotides, between about 12 and 35 nucleotides or between about 12 and 30 nucleotides.

13. The method according to claim 9, wherein the antisense based therapy comprises one or more phosphorothioate bonds.

14. The method according to claim 9, wherein the antisense based therapy comprises one or more 2'-O-methyl modified nucleotides.

15. The method according to claims 9, wherein the antisense based therapy comprises one or more 2'-O-methoxyethyl (2'-MOE) modified nucleotides.

16. The method according to claim 9, wherein the cancer is a solid tumour.

17. The method according to claim 9, wherein the cancer is lung cancer, colorectal cancer, gastric cancer, esophageal cancer, breast cancer, ovarian cancer, head and neck cancer, mesothelioma or prostate cancer.

* * * * *